(12) United States Patent
Beck et al.

(10) Patent No.: US 7,163,949 B1
(45) Date of Patent: Jan. 16, 2007

(54) 4-PHENYL SUBSTITUTED TETRAHYDROISOQUINOLINES AND USE THEREOF

(75) Inventors: James P. Beck, Kalamazoo, MI (US); Mark A. Smith, Landenberg, PA (US)

(73) Assignee: AMR Technology, Inc., Manchester Center, VT (US)

( * ) Notice: Subject to any disclaimer, the term of this patent is extended or adjusted under 35 U.S.C. 154(b) by 118 days.

(21) Appl. No.: 09/704,306

(22) Filed: Nov. 2, 2000

Related U.S. Application Data

(60) Provisional application No. 60/163,270, filed on Nov. 3, 1999.

(51) Int. Cl.
- A61P 25/00 (2006.01)
- A61K 31/535 (2006.01)
- A61K 31/47 (2006.01)
- C07D 413/00 (2006.01)
- C07D 217/00 (2006.01)

(52) U.S. Cl. ............... 514/307; 514/228.2; 514/235.2; 514/253.05; 514/310; 544/62; 544/128; 544/363; 546/143; 546/144

(58) Field of Classification Search ............... 546/144, 546/143; 514/307–310, 228.2, 235.2, 253.05; 544/62, 128, 363
See application file for complete search history.

(56) References Cited

U.S. PATENT DOCUMENTS

| | | | |
|---|---|---|---|
| 3,666,763 A | 5/1972 | Grethe et al. | 260/289 R |
| 3,947,456 A | 3/1976 | Rheiner | 260/289 R |
| 4,113,869 A | 9/1978 | Gardner | 514/307 |
| 4,340,600 A * | 7/1982 | Brenner et al. | 514/307 |
| 4,564,613 A | 1/1986 | Boltze et al. | 514/222 |
| 4,843,071 A | 6/1989 | Hohenwarter | 514/217 |
| 4,902,710 A | 2/1990 | Foster et al. | 514/438 |
| 5,444,070 A | 8/1995 | Moldt et al. | 514/304 |
| 5,532,244 A | 7/1996 | Wong et al. | 514/255 |
| 5,654,296 A | 8/1997 | Kato et al. | 514/213 |
| 5,789,449 A | 8/1998 | Norden | 514/651 |
| 6,121,261 A | 9/2000 | Glatt et al. | 514/236.2 |
| 6,136,803 A | 10/2000 | Freedman et al. | 514/231.2 |
| 6,579,885 B1 | 6/2003 | Beck et al. | 514/307 |
| 6,911,453 B1 | 6/2005 | Hofmeister et al. | 514/307 |

FOREIGN PATENT DOCUMENTS

| | | |
|---|---|---|
| CA | 2015114 | 10/1990 |
| CH | 538477 * | 8/1973 |
| DE | 2062001 * | 7/1971 |
| EP | 0 140 070 A1 | 5/1985 |
| EP | 0360390 A1 | 3/1990 |
| EP | 0 400 319 A1 | 4/1990 |
| EP | 0394989 B1 | 10/1990 |
| EP | 0428434 A2 | 5/1991 |
| EP | 0429366 B1 | 5/1991 |
| EP | 0430771 B1 | 6/1991 |
| EP | 0436334 B1 | 7/1991 |
| EP | 0443132 B1 | 8/1991 |
| EP | 0482539 B1 | 4/1992 |
| EP | 0498069 B1 | 8/1992 |
| EP | 0499313 B1 | 8/1992 |
| EP | 0512901 B1 | 11/1992 |
| EP | 0512902 A1 | 11/1992 |
| EP | 0514273 A1 | 11/1992 |
| EP | 0514274 A1 | 11/1992 |
| EP | 0514275 A1 | 11/1992 |
| EP | 0514276 A1 | 11/1992 |
| EP | 0515681 A1 | 12/1992 |
| EP | 0520555 A1 | 12/1992 |
| EP | 0522808 A2 | 1/1993 |
| EP | 0528495 A1 | 2/1993 |
| EP | 0533280 B1 | 3/1993 |
| EP | 0536817 A1 | 4/1993 |

(Continued)

OTHER PUBLICATIONS

Tirelli et al. Differential effects of direct and indirect dopamine agonists on the induction of gnawing in C57BI/6J mice. J. Pharm. Exp. Ther., 273, 7-15, 1995. Abstract.*

(Continued)

*Primary Examiner*—Brenda Coleman
(74) *Attorney, Agent, or Firm*—Nixon Peabody LLP

(57) ABSTRACT

Provided herein are compounds of the formulae IA–IF. These compounds are tetrahydroisoquinolines of the following structure:

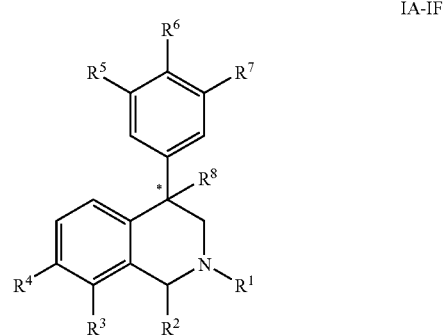

IA-IF wherein $R^1$–$R^8$ for compounds of each of the formulae IA, IB, IC, ID, IE and IF are as described herein. Said compounds are particularly useful in the treatment of various neurological and psychiatric disorders, e.g., ADHD.

38 Claims, No Drawings

FOREIGN PATENT DOCUMENTS

| | | |
|---|---|---|
| EP | 0545478 A1 | 6/1993 |
| EP | 0558156 A2 | 9/1993 |
| EP | 0577394 B1 | 1/1994 |
| EP | 0585913 B1 | 3/1994 |
| EP | 0 599 338 A2 | 6/1994 |
| EP | 0599538 A1 | 6/1994 |
| EP | 0610793 A1 | 8/1994 |
| EP | 0708101 B1 | 10/1994 |
| EP | 0634402 A1 | 1/1995 |
| EP | 0532456 B1 | 3/1995 |
| EP | 0707006 B1 | 10/1995 |
| EP | 0686629 A2 | 12/1995 |
| EP | 0693489 A1 | 1/1996 |
| EP | 0694535 A1 | 1/1996 |
| EP | 0699674 A1 | 3/1996 |
| EP | 0709375 A2 | 5/1996 |
| EP | 0709376 A2 | 5/1996 |
| EP | 0714891 A1 | 6/1996 |
| EP | 0723959 A1 | 7/1996 |
| EP | 0733632 A1 | 9/1996 |
| EP | 0517589 B1 | 12/1996 |
| EP | 0776893 A1 | 6/1997 |
| EP | 0699655 B1 | 9/1997 |
| EP | 0520555 B1 | 9/1999 |
| GB | 2266529 A | 11/1993 |
| GB | 2268931 A | 1/1994 |
| GB | 2269170 A | 2/1994 |
| GB | 2269590 A | 2/1994 |
| GB | 2271566 A | 4/1994 |
| GB | 2271774 A | 4/1994 |
| GB | 2292144 A | 2/1996 |
| GB | 2293168 A | 3/1996 |
| GB | 2293169 A | 3/1996 |
| GB | 2302689 A | 1/1997 |
| JP | 04193867 * | 7/1992 |
| WO | WO 9005525 | 5/1990 |
| WO | WO 9005729 | 5/1990 |
| WO | WO 9109844 | 7/1991 |
| WO | WO 9118899 | 12/1991 |
| WO | WO 9201688 | 2/1992 |
| WO | WO 9206079 | 4/1992 |
| WO | WO 9212151 | 7/1992 |
| WO | WO 9215585 | 9/1992 |
| WO | WO 9217449 | 10/1992 |
| WO | WO 9220661 | 11/1992 |
| WO | WO 9220676 | 11/1992 |
| WO | WO 9221677 | 12/1992 |
| WO | WO 9222569 | 12/1992 |
| WO | WO 9300330 | 1/1993 |
| WO | WO 9300331 | 1/1993 |
| WO | WO 9301159 | 1/1993 |
| WO | WO 9301165 | 1/1993 |
| WO | WO 9301169 | 1/1993 |
| WO | WO 9301170 | 1/1993 |
| WO | WO 9306099 | 4/1993 |
| WO | WO 9309116 | 5/1993 |
| WO | WO 9310073 | 5/1993 |
| WO | WO 9314084 | 7/1993 |
| WO | WO 9314113 | 7/1993 |
| WO | WO 9318023 | 9/1993 |
| WO | WO 9319064 | 9/1993 |
| WO | WO 9321155 | 10/1993 |
| WO | WO 9321181 | 10/1993 |
| WO | WO 9323380 | 11/1993 |
| WO | WO 9324465 | 12/1993 |
| WO | WO 9400440 | 1/1994 |
| WO | WO 9401402 | 1/1994 |
| WO | WO 9402461 | 2/1994 |
| WO | WO 9402595 | 2/1994 |
| WO | WO 9403429 | 2/1994 |
| WO | WO 9403445 | 3/1994 |
| WO | WO 9404494 | 3/1994 |
| WO | WO 9404496 | 3/1994 |
| WO | WO 9405625 | 3/1994 |
| WO | WO 9407843 | 4/1994 |
| WO | WO 9408997 | 4/1994 |
| WO | WO 9410165 | 5/1994 |
| WO | WO 9410167 | 5/1994 |
| WO | WO 9410168 | 5/1994 |
| WO | WO 9410170 | 5/1994 |
| WO | WO 9411368 | 5/1994 |
| WO | WO 9413639 | 6/1994 |
| WO | WO 9413663 | 6/1994 |
| WO | WO 9414767 | 7/1994 |
| WO | WO 9415903 | 7/1994 |
| WO | WO 9419320 | 9/1994 |
| WO | WO 9419323 | 9/1994 |
| WO | WO 9420500 | 9/1994 |
| WO | WO 9426735 | 11/1994 |
| WO | WO 9426740 | 11/1994 |
| WO | WO 9429309 | 12/1994 |
| WO | WO 9502595 | 1/1995 |
| WO | WO 9504040 | 2/1995 |
| WO | WO 9504042 | 2/1995 |
| WO | WO 9506645 | 3/1995 |
| WO | WO 9507886 | 3/1995 |
| WO | WO 9507908 | 3/1995 |
| WO | WO 9508549 | 3/1995 |
| WO | WO 9511880 | 5/1995 |
| WO | WO 9514017 | 5/1995 |
| WO | WO 9515311 | 6/1995 |
| WO | WO 9516679 | 6/1995 |
| WO | WO 9517382 | 6/1995 |
| WO | WO 9518124 | 7/1995 |
| WO | WO 9518129 | 7/1995 |
| WO | WO 9520575 | 8/1995 |
| WO | WO 9521819 | 8/1995 |
| WO | WO 9522525 | 8/1995 |
| WO | WO 9523798 | 9/1995 |
| WO | WO 9526338 | 10/1995 |
| WO | WO 9528418 | 10/1995 |
| WO | WO 9530674 | 11/1995 |
| WO | WO 9530687 | 11/1995 |
| WO | WO 9533744 | 12/1995 |
| WO | WO 9605181 | 2/1996 |
| WO | WO 9605193 | 2/1996 |
| WO | WO 9605203 | 2/1996 |
| WO | WO 9606094 | 2/1996 |
| WO | WO 9607649 | 3/1996 |
| WO | WO 9610562 | 4/1996 |
| WO | WO 9616939 | 6/1996 |
| WO | WO 9618643 | 6/1996 |
| WO | WO 9620197 | 7/1996 |
| WO | WO 9621661 | 7/1996 |
| WO | WO 9629304 | 9/1996 |
| WO | WO 9629317 | 9/1996 |
| WO | WO 9629326 | 9/1996 |
| WO | WO 9629328 | 9/1996 |
| WO | WO 9631214 | 10/1996 |
| WO | WO 9632385 | 10/1996 |
| WO | WO 9637489 | 11/1996 |
| WO | WO 9701553 | 1/1997 |
| WO | WO 9701554 | 1/1997 |
| WO | WO 9703066 | 1/1997 |
| WO | WO 9708144 | 3/1997 |
| WO | WO 9714671 | 4/1997 |
| WO | WO 9717362 | 5/1997 |
| WO | WO 9718206 | 5/1997 |
| WO | WO 9719084 | 5/1997 |
| WO | WO 9719942 | 6/1997 |
| WO | WO 9721702 | 6/1997 |
| WO | WO 9723458 | 7/1997 |
| WO | WO 9736876 | 10/1997 |
| WO | WO 9749710 | 12/1997 |

| WO | WO 9840358 | 9/1998 |
| WO | WO 02/04455 A2 | 1/2002 |

OTHER PUBLICATIONS

Salama et al., Antigenic determinants responsible for the reactions of drug-dependent antibodies with blood cells. Br. J. Haematol., 78, 535-539, 1991. Abstract.*
Trepanier et al., 3,4-dihydroisocarbostyril and 1,2,3,4-tetrahydroisoquinoline derivatives of ephedrine. J. Med. Chem., 16, 342-347, 1973. Abstract.*
Jacob et al, "Dopamine Agonist Properties of N-Alkyl-4-(3,4-dihydroxyphenyl)-1,2,3,4-tetrahydroisoquinolines." Journal of Medicinal Chemistry, 1981, pp. 1013-1015, vol. 24.
Ishimura, et al., "Heterocycles." 1987, pp. 1603-1610, vol. 26.
Mondeshka, et al., "Synthesis, Antiulcer and Antidepressive Activity of 4-(4-Halophenyl)-2-Phenyl-1,2,3,4-Tetrahydroisoquinolines." II Farmaco, 1994, pp. 475-480, vol. 49.
Berge et al., "Pharmaceutical Salts." Journal of Pharmaceutical Sciences, 1977, pp. 1-19, vol. 66, No. 1, American Pharmaceutical Association.
Bundgaard, "Design of Prodrugs." 1985, Elsevier, Amsterdam.
Krogsgaard-Larsen & Bundgaard, "A Textbook of Drug Design and Development." 1991, Harwood Academic Publishers, Chur.
Bundgaard, "Means to Enhance Penetration," Advanced Drug Delivery Reviews, 1992, pp. 1-38, vol. 8, Elsevier Science Publishers, Amsterdam.
Nielsen & Bundgaard, "Glycolamide Esters as Biolabile Prod drugs of Carboxylic Acid Agents: Synthesis, Stability, Bioconversion, and Physiocochemical Properties." Journal of Pharmaceutical Sciences, 1988, pp. 285-298, vol. 77, No. 4, American Pharmaceutical Association.
Kakeya, et al., "Studies on Prodrugs of Cephalosporins . . . " Chem. Pharm. Bull., 1984, pp. 692-698, vol. 32, No. 2.
Middlemiss & Tricklebank, "Centrally Active 5-HT Receptor Agonists and Antagonists." Neuroscience & Biobehavioral Reviews, vol. 16, pp. 75-82, Pergamon Press, 1992.
Greene & Wuts, Protective Groups in Organic Synthesis. 2d. Ed., John Wiley & Sons, Inc., New York, 1991.
Mcomie, Protective Groups in Organic Chemistry, Plenum Press, London, 1973.
Jorgenson, Preparation of ketones,from the reaction of organolithium reagents with carboxytic acids.
Larock, Comprehensive Organic Transformations. VCH Publishers, New York, 1989.
Venkov et al A New Synthesis of 1,2,3,4-Tetrahydro-2-methyl-4-phenylisoquinolines, 1990.
Dandridge, et al., "Synthesis, Resolution, Absolute Stereochemistry, and Enantioselectivity of 3', 4'-Dihydroxynomifensine." J. Med. Chem. 1984, 27, 28-35. American Chemical Society.
Kihara, et al., "A Convenient Synthesis of 4-Substituted 1,2,3,4-Tetrahydroisoquinolin-4-OLS by a Novel Intramolecular Barbier Reaction and by an Insertion Reaction: Reaction Scope and Limitations." Tetrahedron vol. 48, No. 1, pp. 67-78, Pergamon Press, 1992.
Blomberg et al, "The Barbier Reaction- A One-Step Alternative for Syntheses via Organomagnesium Compounds."
Hudlicky, "Fluorination with Diethylaminosulfur Trifluoride and Related Aminofluorosulfurances," Organic Reactions, 1985, vol. 35, pp. 513-637.
Gao, et al., "Asymmetric Hetero Diels-Alder Reaction Catalyzed by Stable and Easily Prepared CAB Catalysts." Tetrahedron, vol. 50, No. 4, pp. 979-988, Pergamon Press, 1994.
Miller et al, "An Efficient Synthesis of 4-Aryl-1,2,3,4-Tetrahydroisoquinolines." Synthetic Communications, vol. 24, No. 8, pp. 1187-1193, Marcel Dekker, Inc., 1994.
Dudley, et al., "The Actions of Xylamine on Central Noradrenergic Neurons." The Journal of Pharmacology and Experimental Therapeutics, vol. 217, No. 3, pp. 834-840, The American Society for Pharmacology and Experimental Therapeutics, 1981.
Stille, "Zur pharmakologischen Prufung von Antidepressiva am Beispiel eines Dibenzodiazepins" Arzneimittel-Forschung, Juni 1964.
Maryanoff et al., "Pyrroloisoquinoline Antidepressants. 2. In-Depth Exploration of Structure-Activity Relationships," J. Med. Chem. 30(8):1433-1454 (1987).
Kihara et al., "Synthesis and Pharmacological Evaluation of Phenolic 2-Methyl-4-Phenyl-1,2,3,4,-Tetrahydroisoquinolin-4-ols As New Norepinephrine Potentiator," Drug Design and Discovery 11(3):175-183 (1994).
Kihara et al., "Synthesis and Enantioselectivity of Optically Active 1- and 3-Substituted 4-Phenyl-1,2,3,4-Tetrahydroisoquinolin-4-ols and Related Compounds As Norepinephrine Potentiators," Chemical and Pharmaceutical Bulletin 43(9):1543-1546 (1995).
Cliffe, "(S)-N-tert Butyl-3-(4-(2-methoxyphenyl)-piperazin-l-yl)-2-phenylpropanamide[S]-WAY-100135): A Selective Antagonist at Presynaptic and Postsynaptic-5HT Receptors" J. Med. Chem. 36:1509-10 (1988).
Aihara et al., "Increasing 5-Lipoxygenase Inhibitory Activities by Oxidative Conversion of o-Methoxyphenols to Catechols Using a $Cu^{2+}$—Ascorbic Acid—$O_2$ System," Chem. Pharm. Bull., 38(3):842-844 (1990).
Jorgenson, Preparation of ketones,from the reaction of organolithium reagents with carboxylic acids. Organic Reactions, pp. 1-97 (1997).
Blomberg & Hartog, "The Barbier Reaction- A One-Step Alternative for Syntheses via Organomagnesium Compounds." Synthesis, pp. 18-30 (1970).
Zára-Kaczián et al., "8-Amino-4-Aryl-2-Methyl-1,2,3,4-Tetrahydroisoquinolines: Reactions of the Amino Group Via the Diazonium Salts," Acta Chimica Hungarica 126(4):573-584 (1989).
Banerji et al., "Studies on Single-Electron Transfer Reagents. Part $IV^{1a-c}$ Reaction of Nitrogen Heterocycles with Sodium Naphthalenide, " Tetrahedron 50(30):9079-9096 (1994).
Bobowski & Gottlieb, "4-Substituted 1,2,3,4-tetrahydro-3-3-dimethylisoquinolines. II.," Heterocyclic Chem. 19(1):21-27 (1982).
Brown & Dyke, "1,2-Dihydroisoquinolines. II. Berbine Synthesis," Tetrahedron 22(8):2429-35 (1966).
Brown & Dyke, "1,2-Dihydroisoquinolines. III. Dimerization," Tetrahedron 22(8):2437-2443 (1966).
Chandrasekhar et al., "Highly Efficient Synthesis of 3-alkyl/aryl1-4-aryl-1,2,3,4-tetrahydroisoquinolines from N,N-dibenzylaminols," Tetrahedron Lett. 43(10):1885-1888 (2002).
Georgiadis et al., "Synthesis and Complexation Properties of a Water-Soluble Optically Active Cyclophane Incorporating a 4-Naphthyl-1,2,3,4-tetrahydroisoquinoline Unit as a Chiral Spacer," J. Org. Chem. 56(10):3362-3369 (1991).
Knabe & Herbort, "Dehydrogenation of Tertiary Amines with Aercury (II) Acetate in the Presence of EDTA. XIII. Oxidative Dimerization of 6,7-dimethoxy-2-methyl-1,1-diethyl-1,2,3,4-tetrahydroisoquinoline," Archiv. der Pharmazie. und Berichte der Deutschen Pharmazeutischen Gesellschaft 300(9):774-783 (1967).
Knabe & Renz, "Synthesis of 3,4'-Biisoquinolines," Archiv. der Pharmazie. (Weinheim, Germany) 307(8):612-622 (1974).
Seebach et al., "Alkylation of Amino Acids without Loss of the Optical Activity: Preparation of α-Substituted Proline Derivatives. A Case of Self-Reproduction of Chirality," J. American Chem. Soc. 105(16):5390-5398 (1983).
Sugiura & Hamada, "Studies on Nitrogen-Containing Heterocyclic Compounds. XXXV. Syntheses and Reduction of 4-Amino-2-2cyano-1,3-dimethoxy-1,2,3,4-tetrahydroisoquinolines," Yakugaku Zasshi 99(6):556-563 (1979).
Sugiura et al., "Synthesis and Stereochemistry of 3,7-Diazatricyclo[4.2.2.2$^{2,5}$]dodeca-9,11-dienes Derived By [4+4] Cyclodimerization of 2,3-Dihydroisoquinoline Derivatives," Chem. Pharm. Bull. 46(12):1862-1865 (1998).
Uno et al., "A Novel Method for the Synthesis of 4-Isoquinolinols," J. Heterocyclic Chem. 28(2):341-346 (1991).
CAS Number 53885-32-8.
CAS Number 53885-23-7.
Beilstein No. 455853 (CAS 71730-66-0).
Beilstein No. 4048047 (CAS 17074-38-3, 17074-39-4).

Beilstein No. 4102323 (CAS 53885-34-0).
Beistein No. 4341479 (CAS 134021-24-2).
Beilstein No. 4494373 (CAS 82416-61-3).
Beilstein No. 4774688 (CAS 133160-36-8).
Beistein No. 4787749 (CAS 133043-12-6, 133160-34-6, 133160-35-7).
Beilstein No. 4787750 (CAS 133043-12-6, 133160-34-6, 133160-35-7).
Beilstein No. 4787836 (CAS 133043-20-6, 133043-31-9).
Beilstein No. 4787837 (CAS 133043-20-6, 133043-31-9).
Beilstein No. 4788234 (CAS 133043-19-3, 133043-30-8).
Beilstein No. 4788235 (CAS 133043-19-3, 133043-30-8).
Beilstein No. 4789758 (CAS 133043-21-7, 133043-22-8).
Burrows et al., "Antidepressant Efficacy and Tolerability of the Selective Norepinephrine Reuptake Inhibitor Reboxetine: A Review," *J. Clin Psychiatry* 59 (Suppl. 14):4-7 (1998)(98819-76-2 Registry (Reboxetine)).

Desai et al., "Relationship Between in Vivo Occupancy at the Dopamine Transporter and Behavioral Effects of Cocaine, GBR 12909 [1-{2-[Bis-(4-fluoropheny)methoxy]ethyl}-4-(3-phenylpropyl)piperazine], and Benztropine Analogs," *JPET* 315(1):397-404 (2005).

Hyttel, "Pharmacological Characterization of Selective Serotonin Reuptake Inhibitors (SSRIs)," *Int. Clin. Psychopharmacol.* 9(Suppl. 1):19-26 (1994) (61869-08-7 Registry (Paroxeine); 59729-32-7 Registry (Citalopram); 79559-97-0 Registry (Sertraline); 54910-89-3 Registry (Fluoxetine): 54739-18-3 Registry (Fluvoxamine)).

Kametani et al., "Studies on the Synthesis of Heterocyclic Compounds-DXCI," *Tetrahedron* 31:235-238 (1975).

Müller, "Current St. John's Wort Research from Mode of Action to Clinical Efficacy," *Pharmacological Research* 47:101-109 (2003).

\* cited by examiner

4-PHENYL SUBSTITUTED TETRAHYDROISOQUINOLINES AND USE THEREOF

This application claims the benefit of U.S. Provisional Application No. 60/163,270, filed Nov. 3, 1999.

FIELD OF THE INVENTION

The present invention relates to compounds, compositions, methods for the treatment of various neurological and psychological disorders, and the use of the compounds in combination therapy. In particular, the present invention relates to such compounds, compositions and methods wherein the compounds are novel 4-phenyl substituted tetrahydroisoquinolines derivatives.

BACKGROUND OF THE INVENTION

Serotonin, dopamine and norepinephrine are known to be important chemical messengers participating in the transmission of nerve impulses in the brain. These messengers are liberated at specific site on pre-synaptic cells and received, to complete transmission of the impulse, at specific sites on post-synaptic cells. Their effect is then terminated by metabolism or by uptake into the pre-synaptic cells. Drugs capable of blocking the pre-synaptosomal uptake of either of these chemical messengers in the brain, are useful in alleviating disorders associated with decreased levels of these chemical messengers. For example, duloxetine and fluoxetine which are known serotonin reuptake inhibitors have been found to be useful in the treatment of depression, obesity and obsessive-compulsive disease (Wong, et al., U.S. Pat. No. 5,532,244). Also, Moldt, et al., U.S. Pat. No. 5,444,070, discloses the use of dopamine reuptake inhibitors in the treatment of depression, Parkinsonism, drug addiction and/or abuse, cocaine and/or amphetamine addiction and/or abuse. Freedman, et al., U.S. Pat. No. 6,136,803 also discloses synaptic norepinephrine or serotonin uptake inhibitors which are useful in treating depression in a patient. Furthermore, Norden, U.S. Pat. No. 5,789,449 discloses the use of serotonin re-uptake inhibitors in treating psychiatric symptoms consisting of anger, rejection sensitivity, and lack of mental or physical energy. Also, Foster, et al., U.S. Pat. No. 4,902,710, discloses the use of serotonin and norepinephrine uptake inhibitors in suppressing the desire of humans to smoke or consume alcohol. Thus, there continues to remain a need to develop novel compounds which block reuptake of norephinephrine, dopamine or serotonin.

Compounds which inhibit the reuptake of serotonin or norepinephrine, have also been used in combination therapy. For example, Glatt, et al., U.S. Pat. No. 6,121,261 discloses the use of selective serotonin reuptake Inhibitors or norephinephrine uptake inhibitiors, in combination with neurokinin-1receptor antagonist for treating attention deficit disorder in a patient.

Also, Hohenwarter, U.S. Pat. No. 4,843,071 discloses the use of a norepinephrine re-uptake inhibitor and a norepinephrine precursor in the treatment of obesity, drug abuse, or narcolepsy in a patient. Furthermore, Wong, et al., U.S. Pat. No. 5,532,244, discloses the use of serotonin reuptake inhibitors in combination with a serotonin IA receptor antagonist, to increase the availability of serotonin, norepinephrine and dopamine in the brain.

The treatment of a variety of neurological and psychiatric disorders is characterized by a number of side effects believed to be due to the compounds' inability to selectvely block certain neurochemicals, and not others. ADHD, for example, is a disease affecting 3–6% of school age children, and is also recognized in percentage of adults. Aside from hampering performance at school, and at work, ADHD is a significant risk factor for the subsequent development of anxiety disorders, depression, conduct disorder and drug abuse. Since current treatment regimes require psychostimulants, and since a substantial number of patients (30%) are resistant to stimulants or cannot tolerate their side effects, there is a need for a new drug or class of drugs which treats ADHD and does not have resistance or side effect problems. In addition, methylphenidate, the current drug of choice for the treatment of ADHD, induces a number of side effects; these include anorexia, insomnia and jittery feelings, tics, as well as increased blood pressure and heart rate secondary to the activation of the sympathetic nervous system. However, Methylphenidate also has a high selectivity for the dopamine transporter protein over the norepinephrine transporter protein (DAT/NET Ki ratio of 0.1), which can lead to addiction liability and requires multiple doses per day for optimal efficacy. Thus, there continues to remain a need to develop novel compounds which block reuptake of norephinephrine, dopamine, and serotonin with particular selectivity ratios.

U.S. Pat. No. 3,947,456, discloses tetrahydroisoquinolines which are said to have utility as anti-depressants. U.S. Pat. No. 3,666,763, describes the use of phenyl tetrahydroisoquinoline derivatives as antidepressants and antihypotensives. Canadian Patent Application No. 2,015,114, discloses the use of phenyl tetrahydroisoquinoline derivatives as antidepressants; moreover, described therein are apparently nonselective as to norepinephrine, serotonin and dopamine uptake. UK Patent Application No. 2,271,566, discloses the use of phenyl tetrahydroisoquinoline derivatives as anti-HIV agents. PCT International Application No. WO98/40358 discloses the use of phenyl tetrahydroisoquinoline derivatives to be useful in the treatment of disorders of glucose metabolic pathways. WO97/36876 discloses the use of phenyl tetrahydroisoquinoline derivatives as anti-cancer agents. WO97/23458 also describes 4 phenyl-substituted tetrahydroisoquinolines as NMDA receptor ligands useful for conditions associated with neuronal loss. Phenyl-substituted tetrahydroisoquinolines are also described in Mondeshka et al II Farmaco, 1994,49 pp. 475–481.

Nomofensine® which is a 4 phenyl-substituted tetrahydroisoquinoline derivative is known to inhibit the neuronal uptake of dopamine and other catecholamines and has shown clinical efficacy for ADHD. However, long term administration of Nomofensine® results in fatal immune hemolytic anemia. Thus, there continues to remain a need to develop novel compounds which treat ADHD but do not have the serious side effects associated with Nomifensine® or the currently prescribed psychostimulants.

The present invention discloses novel aryl and heteroaryl substituted tetrahydroisoquinoline derivatives compounds which block reuptake of norephinephrine, dopamine, or serotonin, and are useful as alternatives to methylphenidate, and known psychostimulants, in the treatment of ADHD and other neurological and psychiatric disorders.

The present inventors have discovered that the claimed compounds which block reuptake of norephinephrine, dopamine, and serotonin with particular selectivity ratios, e.g., being more selective for the norepinephrine transporter (NET) protein than dopamine transporter (DAT) protein or serotonin transporter (SERT) protein (lower Ki for NET than for DAT and SERT). It is postulated that the compounds would therefore be effective as an ADHD treatment with reduced addictive liability profiles. In particular, some of the compounds of this invention are surprisingly and particularly selective for NET over the SERT protein, thus also affording compounds without the known side effect profiles of the selective serotonin reuptake inhibitor (SSRI) class of compounds.

SUMMARY OF THE INVENTION

This invention is directed to a compound of formulae (IA-F)

IA-IF

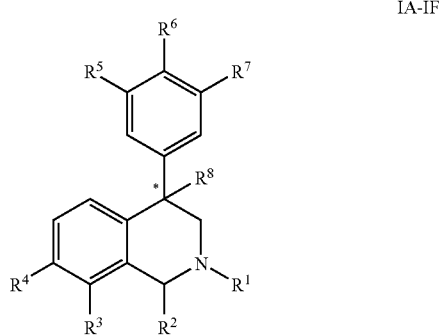

wherein:

the carbon atom designated * is in the R or S configuration;

$R_1$ is $C_1$–$C_6$ alkyl, $C_2$–$C_6$ alkenyl, $C_2$–$C_6$ alkynyl, $C_3$–$C_6$ cycloalkyl or $C_4$–$C_2$cycloalkylalkyl, each of which is optionally substituted with 1 to 3 substituents independently selected at each occurrence thereof from $C_1$–$C_3$ alkyl, halogen, aryl, —CN, —$OR^9$ and —$NR^9R^{10}$;

$R^2$ is H, $C_1$–$C_6$ alkyl, $C_2$–$C_6$ alkenyl, $C_2$–$C_6$ alkynyl, $C_3$–C. cycloalkyl, $C_1$–$C_6$ cycloalkylalkyl or $C_1$–$C_6$ haloalkyl;

$R^2$ is H, halogen, —$OR^{11}$, —$S(O)_nR^{12}$, —$S(O)_nNR^{11}R^{12}$, —CN, —$C(O)R^{12}$, —$C(O)NR^{11}R^{12}$, $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl, —O(phenyl) or —O(benzyl), wherein each of —O(phenyl) and —O(benzyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy, or wherein $R^3$ is a $C_1$–$C_6$ alkyl, $C_1$–$C_6$ alkenyl, $C_2$–$C_6$ alkynyl, $C_3$–$C_6$ cycloalkyl or $C_4$–$C_2$ cycloalkylalkyl group, then said group is optionally substituted with from 1 to 3 substituents selected independently at each occurrence thereof from $C_1$–$C_3$ alkyl, halogen, aryl, —CN, —$OR^9$ and —$NR^9R^{10}$; provided that for compounds of formula IA, $R^3$ is $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, each of which is optionally substituted with from 1 to 3 substituents selected independently at each occurrence thereof from $C_1$–$C_3$ alkyl, halogen, aryl, —CN, —$OR^9$ and $NR^9R^{10}$;

provided that for compounds of formula IB, $R^3$ is —O(phenyl), —O(benzyl), —$OC(O)R^{13}$ or —$S(O)_nR^{12}$, each of —O(phenyl) and —O(benzyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;

$R^4$ is H, halogen, —$OR^{11}$, —$S(O)_nR^{12}$, —$S(O)NR^{11}R^{12}$, —CN, —$C(O)R^{12}$, —$C(O)NR^{11}R^{12}$, —$NR^{11}R^{12}$, $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl, —O(phenyl) or —O(benzyl), wherein each of —O(phenyl) and —O(benzyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy and wherein $R^4$ is a $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl group, then said group is optionally substituted with from 1 to 3 substituents selected independently at each occurrence thereof from $C_1$–$C_3$ alkyl, halogen, aryl, —CN, —$OR^9$ and —$NR^9R^{10}$; provided that for compounds of formula IC, $R^4$ is $C_1$–$C_6$ alkyl, $C_2$–$C_6$ alkenyl, $C_2$–$C_6$ alkynyl, $C_3$–$C_6$ cycloalkyl, or $C_4$–$C_7$ cycloalkylalkyl, each of which is is optionally substituted with from 1 to 3 substituents selected independently at each occurrence thereof from $C_1$–$C_3$ alkyl, halogen, aryl, —CN, —$OR^9$ and —$NR^9R^{10}$, or $R^5$ and $R^6$ or $R^6$ and $R^7$ may be —O—$C(R^2)_2$—O—;

provided that for compounds of formula ID, $R^4$ is —O(phenyl), —O(benzyl), —$OC(O)R^{13}$, —$NR^{11}R^{12}$ or —$S(O)_nR^{12}$, each of —O(phenyl) and —O(benzyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;

$R^5$, $R^6$ and $R^7$ in compounds of each of the formulae IA, IB, IC, ID, IE and IF are each independently H, halogen, —$OR^{11}$, —$S(O)_nR^{12}$, —CN, —$C(O)R^{12}$, —$NR^{11}R^{12}$, —$C(O)NR^{11}R^{12}$, —$NR^{11}C(O)R^{12}$, —$NR^{11}C(O)_2R^{12}$, —$NR^{11}C(O)NR^{12}R^{13}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, wherein each of $R^5$, $R^6$ and $R^7$ is a $C_1$–$C_9$ alkyl, $C_2$–$C_6$ alkenyl, $C_2$–$C_6$ alkynyl, $C_3$–$C_6$ cycloalkyl or $C_4$–$C_7$ cycloalkylalkyl group, then said group is optionally substituted with from 1 to 3 substituents selected independently at each occurrence thereof from $C_1$–$C_3$ alkyl, halogen, aryl, —CN, —$OR^9$ and —$NR^9R^{10}$, or $R^5$ and $R^6$ or $R^6$ and $R^7$ may be —O—$C(R^{12})_2$—O—;

provided that for compounds of formula IE at least one of $R^5$ or $R^7$ is fluoro, chloro, or methyl; or $R^5$ and $R^6$ are each independently —O—$C(R^{12})_2$—O— in compounds of the formulae IE, but only where $R^7$ is fluoro, chloro or methyl;

or $R^7$ and $R^6$ can independently also be —O—$C(R^{12})_2$—O— in compounds of the formulae IE, but only where $R^5$ is fluoro, chloro or methyl;

$R^8$ is H, halogen, or $OR^{11}$, provided that for compounds of formula IF, $R^8$ is halogen;

$R^9$ and $R^{10}$ are each independently H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, —$C(O)R^{13}$, phenyl or benzyl, where phenyl or benzyl is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;

or $R^9$ and $R^{10}$ are taken together with the nitrogen to which they are attached to form piperidine, pyrrolidine, piperazine, N-methylpiperazine, morpholine, or thiomorpholine;

$R^{11}$ is H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, —$C(O)R^{13}$, phenyl or benzyl, where $R^{11}$ is a $C_1$–$C_4$ alkyl, phenyl or benzyl group, then said group is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;

$R^{12}$ is H, amino, $C_1$–$C_4$ alkyl, ($C_1$–$C_4$ alkyl)amino, $C_1$–$C_4$ haloalkyl, $C_1$–$C_4$ alkoxyalkyl, $C_3$–$C_6$ cycloalkyl, $C_4$–$C_7$ cycloalkylalkyl, phenyl or benzyl, where phenyl or benzyl is optionally substituted from 1 to 3 times with a substituent selected independently from halogen, cyano, $C_1$–$C_4$ alkyl, $C_1$–$C_4$ haloalkyl and $C_1$–$C_4$ alkoxy;

or $R^{11}$ and $R^{12}$ are taken together with the nitrogen to which they are attached to form piperidine, pyrrolidine, piperazine, N-methylpiperazine, morpholine, or thiomorpholine;

provided that only one of $R^9$ and $R^{10}$ or $R^9$ and $R^{10}$ are taken together with the nitrogen to which they are attached to form piperidine, pyrrolidine, piperazine, N-methylpiperazine, morpholine, or thiomorpholine;

$R^{13}$ is $C_1$–$C_4$ alkyl, $C_1$–$C_4$ haloalkyl or phenyl;

n is 0, 1, or 2, and;

aryl is phenyl which is optionally substituted 1–3 times with halogen, cyano, $C_1$–$C_4$ alkyl, $C_1$–$C_4$ haloalkyl and $C_1$–$C_4$ alkoxy, or an oxide thereof, a pharmaceutically acceptable salt thereof, a solvate thereof, or prodrug thereof.

DETAILED DESCRIPTION OF THE INVENTION

As used above, and throughout the description of the invention, the following terms, unless otherwise indicated, shall be understood to have the following meanings:—

The term "Alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "Alkenyl" means an aliphatic hydrocarbon group containing a carbon—carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Exemplary alkenyl groups include ethenyl, propenyl, n-butenyl, and i-butenyl.

The term "Alkynyl" means an aliphatic hydrocarbon group containing a carbon—carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Exemplary alkynyl groups include ethynyl, propynyl, n-butynyl, 2-butynyl, 3-methylbutynyl, and n-pentynyl.

The term "Aryl" means an aromatic monocyclic or multicyclic ring system of 6 to about 14 carbon atoms, preferably of 6 to about 10 carbon atoms. Representative aryl groups include phenyl and naphthyl.

The term "Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen or sulfur. Preferred heteroaryls contain about 5 to 6 ring atoms. The prefix aza, oxa or thia before heteroaryl means that at least a nitrogen, oxygen or sulfur atom, respectively, is present as a ring atom. A nitrogen atom of a heteroaryl is optionally oxidized to the corresponding N-oxide. Representative heteroaryls include pyrazinyl; furanyl; thienyl; pyridyl; pyrimidinyl; isoxazolyl; isothiazolyl; oxazolyl; thiazolyl; pyrazolyl; furazanyl; pyrrolyl; pyrazolyl; triazolyl; 1,2,4-thiadiazolyl; pyrazinyl; pyridazinyl; quinoxalinyl; phthalazinyl; 1(2H)-phthalazinonyl; imidazo[1,2-a]pyridine; imidazo[2,1-b]thiazolyl; benzofurazanyl; indolyl; azaindolyl; benzimidazolyl; benzothienyl; quinolinyl; imidazolyl; thienopyridyl; quinazolinyl; thienopyrimidyl; pyrrolopyridyl; imidazopyridyl; isoquinolinyl; benzoazaindolyl; azabenzimidazolyl, 1,2,4-triazinyl; benzothiazolyl and the like.

The term "Alkoxy" means an alkyl-O— group wherein the alkyl group is as herein described. Exemplary alkoxy groups include methoxy, ethoxy, n-propoxy, i-propoxy, n-butoxy and heptoxy.

The term "Compounds of the invention", and equivalent expressions, are meant to embrace compounds of general formulae (IA-F) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "Cycloalkyl" means a non-aromatic mono- or multicyclic ring system of about 3 to about 7 carbon atoms, preferably of about 5 to about 7 carbon atoms. Exemplary monocyclic cycloalkyl include cyclopentyl, cyclohexyl, cycloheptyl, and the like.

The term "Cycloalkylalkyl" means an cycloalkyl-alkyl-group in which the cycloalkyl and alkyl are as defined herein. Exemplary cycloalkylalkyl groups include cyclopropylmethyl and cyclopentylmethyl.

The term "Halo" or "halogen" means fluoro, chloro, bromo, or iodo.

The term "Haloalkyl" means both branched and straight-chain alkyl substituted with 1 or more halogen, wherein the alkyl group is as herein described.

The term "Haloalkoxy" means a $C_{1-4}$ alkoxy group substituted by at least one halogen atom, wherein the alkoxy group is as herein described.

The term "Substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "Pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example S. M. Berge, et al., "Pharmaceutical Salts," J. Pharm. Sci., 66: p. 1–19 (1977) and *Remington's Pharmaceutical Sciences,* 17th ed., Mack Publishing Company, Easton, Pa., 1985, p. 1418, which are incorporated herein by reference.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, Nethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p. 309–396, 1985; A Textbook of Drug Design and Development, Krogsgaard-Larsen and H. Bundgaard, ed., Chapter 5; "Design and Applications of Prodrugs" p. 113–191, 1991; Advanced Drug Delivery Reviews, H. Bundgard, 8, p. 1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference. Examples of prodrugs include, but are not limited to, acetate, formate and benzoate derivatives of alcohol and amine functional groups in the compounds of the invention.

The term "Therapeutically effective amounts" is meant to describe an amount of compound of the present invention effective in increasing the levels of serotonin, norepinephrine or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history; the particular compound used, as well as the carrier in which it is formulated and the route of administration selected for it; and, the nature and severity of the condition being treated.

The term "Pharmaceutical composition" means a composition comprising a compound of formulae (IA-F) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar—agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

The term "Pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "Pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

PREFERRED EMBODIMENTS

Another embodiment of the invention is a compound of formulae IA–IF wherein:
 the carbon atom designated * is in the R or S configuration.

Another embodiment of the invention is a compound of formulae IA, IB, IC, ID, IE and IF, wherein:
 $R^1$ is $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, each of which is optionally substituted with from 1 to 3 substituents selected independently at each occurrence thereof from $C_1$–$C_3$ alkyl, halogen, aryl, —CN, —$OR^9$ and —$NR^9R^{10}$.

Another embodiment of the invention is a compound of formulae IA, IB, IC, ID, IE and IF, wherein:
 $R^2$ is H, $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl or $C_1$–$C_6$ haloalkyl.

Another embodiment of the invention is a compound of formulae IA, wherein:
 $R^3$ as $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, each of which is optionally substituted with from 1 to 3 substituents selected independently at each occurrence thereof from $C_1$–$C_3$ alkyl, halogen, aryl, —CN, —$OR^9$ and —$NR^9R^{10}$.

Another embodiment of the invention is a compound of formulae IB, wherein:
 $R^3$ as —O(phenyl), —O(benzyl), —OC(O)$R^{13}$ or —S(O)$_n$$R^{12}$, each of —O(phenyl) and —O(benzyl) optionally substituted with 1 to 3 substituents selected independently at each occurrence thereof from halogen, cyano, $C_1$–$C_4$ alkyl, $C_1$–$C_4$ haloalkyl or $C_1$–$C_4$ alkoxy.

Another embodiment of the invention is a compound of formulae IC, ID, IE and IF, wherein:
 $R^3$ is H, halogen, —$OR^{13}$, —S(O)$_n$$R^{12}$, —S(O)$NR^{11}R^{12}$, —CN, —C(O)$R^{12}$, —C(O)$NR^{11}R^{12}$, —O(phenyl), O(benzyl), —OC(O)$R^{13}$ or —S(O)$_n$$R^2$, $C_1$–$C_6$ alkyl, $C_2$–$C_6$ alkenyl, $C_2$–$C_6$ alkynyl, $C_3$–$C_6$ cycloalkyl and $C_4$–$C_7$ cycloalkylalkyl, wherein each of $C_1$–$C_6$ alkyl, $C_2$–$C_6$ alkenyl, $C_2$–$C_6$ alkynyl, $C_3$–$C_6$ cycloalkyl and $C_4$–$C_7$ cycloalkylalkyl is optionally substituted with from 1 to 3 substituents selected independently at each occurrence thereof from $C_1$–$C_3$ alkyl, halogen, aryl, —CN, —$OR^9$ and —$NR^9R^{10}$, and wherein $R^3$ is a —O(phenyl) or —O(benzyl) group, then said group is optionally substituted with 1 to 3 substituents selected independently at each occurrence thereof from halogen, cyano, $C_1$–$C_4$ alkyl, $C_1$–$C_4$ haloalkyl or $C_1$–$C_4$ alkoxy.

Another embodiment of the invention is a compound of formula IC, wherein:
 $R^4$ is $C_1$–$C_6$ alkyl, $C_2$–$C_6$ alkenyl, $C_2$–$C_6$ alkynyl, $C_3$–$C_6$ cycloalkyl, or $C_4$–$C_7$ cycloalkylalkyl, each of which is optionally substituted with from 1 to 3 substituents selected independently at each occurrence thereof from $C_1$–$C_3$ alkyl, halogen, aryl, —CN, —$OR^9$ and —$NR^9R^{10}$.

Another embodiment of the invention is a compound of formula ID, wherein:
 $R^4$ is —O(phenyl), —O(benzyl), —OC(O)$R^{13}$, —$NR^{11}R^{12}$ or —S(O)$_n$$R^{12}$, and said —O(phenyl) or —O(benzyl) is optionally substituted with 1 to 3 substituents selected independently at each occurrence thereof from halogen, cyano, $C_1$–$C_4$alkyl, $C_1$–$C_4$ haloalkyl and $C_1$–$C_4$ alkoxy.

Another embodiment of the invention is a compound of formula IA, IB, IE and IF, wherein:
 $R^4$ is H, halogen, —$OR^{11}$, —S(O)$_n$$R^{12}$, —S(O)$NR^{11}R^{12}$, —CN, —O(phenyl), —O(benzyl), —OC(O)$R^{13}$, —C(O)$R^{12}$, —C(O)$NR^{11}R^{12}$, —$NR^{11}R^{12}$, $C_1$–$C_6$ alkyl, $C_2$–$C_6$ alkenyl, $C_2$–$C_6$ alkynyl, $C_3$–$C_6$ cycloalkyl and $C_4$–$C_7$ cycloalkylalkyl, wherein $R^4$ is a $C_1$–$C_6$ alkyl, $C_2$–$C_6$ alkenyl, $C_1$–$C_6$ alkynyl, $C_3$–$C_6$ cycloalkyl or $C_4$–$C_7$ cycloalkylalkyl group, then said group is optionally substituted with 1 to 3 substituents selected independently at each occurrence thereof from $C_1$–$C_3$ alkyl, halogen, aryl, —CN, —$OR^9$ and —$NR^9R^{10}$, and wherein $R^4$ a —(O)phenyl or —(O)benzyl group, then said group is optionally substituted from 1 to 3 times with a substituent selected independently at each occurrence thereof from halogen, cyano, $C_1$–$C_4$ alkyl, $C_1$–$C_4$ haloalkyl, and $C_1$–$C_4$ alkoxy.

Another embodiment of the invention is a compound of formulae IA, IB, IC, ID and IF, wherein:
 $R^5$, $R^6$ and $R^7$ are each independently H, halogen, —$OR^{11}$, —S(O)$_n$$R^{12}$, —CN, —C(O)$R^{12}$, —$NR^{11}R^{12}$, —C(O)$NR^{11}R^{12}$, —$NR^{11}$C(O)$R^{12}$, —$NR^{11}$C(O)$_2$$R^{12}$, —$NR^{11}$C(O)$NR^{12}R^{13}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, wherein each $R^5$, $R^6$ and $R^7$ is independently a $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl group, then said group is optionally substituted from 1 to 3 times with substituents selected independently at each occurrence thereof from $C_1$–$C_3$ alkyl, halogen, aryl, —CN, —$OR^9$ and —$NR^9R^{10}$, or $R^5$ and $R^6$ or $R^6$ and $R^7$ may be —O—C($R^{12}$)$_2$—O—.

Another embodiment of the invention is a compound of formula IE, wherein:
 when $R^5$ is fluoro, chloro, or methyl; then $R^7$ and $R^6$ are each independently H, halogen, —$OR^{11}$, —S(O)$_n$$R^{12}$, —CN, —C(O)$R^{12}$, —$NR^{11}R^{12}$, —C(O)$NR^{11}R^{12}$, —$NR^{11}$C(O)$R^{12}$, —$NR^{11}$C(O)$_2$$R^{12}$, —$NR^{11}$C(O)$NR^{12}R^{13}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, wherein each of $R^7$ and $R^6$ are a $C_1$–$C_6$ alkyl, $C_2$–$C_6$ alkenyl, $C_2$–$C_6$ alkynyl, $C_1$–$C_6$ cycloalkyl or $C_4$–$C_7$ cycloalkylalkyl group, said group is optionally substituted with from 1 to 3 substituents selected independently at each occurrence thereof from $C_1$–$C_3$ alkyl, halogen, aryl, —CN, —$OR^9$ and —$NR^9R^{10}$, provided that $R^7$ is not fluoro, chloro, or methyl.

Another embodiment of the invention is a compound of formula IE, wherein:
 $R^7$ is fluoro, chloro or methyl, then $R^5$ and $R^6$ together can also be —O—C($R^{12}$)$_2$—O—.

Another embodiment of the invention is a compound of formula IE, wherein:
 $R^5$ is fluoro, chloro or methyl, then $R^7$ and $R^6$ together can also be —O—C($R^{12}$)$_2$—O—.

Another embodiment of the invention is a compound of formulae IA–IE, wherein:
 $R^8$ is H, halogen, or $OR^{11}$.

Another embodiment of the invention is a compound of formula IF, wherein
R$^8$ is halogen.

Another embodiment of the invention is a compound of formulae IA-F, wherein:
R$^9$ and R$^{10}$ are each independently H, C$_1$–C$_4$ alkyl, C$_1$–C$_4$ haloalkyl, C$_1$–C$_4$ alkoxyalkyl, C$_3$–C$_6$ cycloalkyl, C$_4$–C$_7$ cycloalkylalkyl, —C(O)R$^{13}$, phenyl or benzyl, where said phenyl or benzyl is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy; or
R$^9$ and R$^{10}$ are taken together with the nitrogen to which they are attached to form piperidine, pyrrolidine, piperazine, N-methylpiperazine, morpholine, or thiomorpholine rings.

Another embodiment of the invention is a compound of formulae IA-F, wherein:
R$^{11}$ is H, C$_1$–C$_4$ alkyl, C$_1$–C$_4$ haloalkyl, C$_1$–C$_4$ alkoxyalkyl, C$_3$–C$_6$ cycloalkyl, C$_4$–C$_7$ cycloalkylalkyl, —C(O)R$^{13}$, phenyl or benzyl, where said phenyl or benzyl is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy.

Another embodiment of the invention is a compound of formulae IA-F, wherein:
R$^{12}$ is H, C$_1$–C$_4$ alkyl, C$_1$–C$_4$ haloalkyl, C$_1$–C$_4$ alkoxyalkyl, C$_3$–C$_6$ cycloalkyl, C$_4$–C$_7$ cycloalkylalkyl, phenyl or benzyl, where said phenyl or benzyl is optionally substituted from 1 to 3 times with a substituent selected independently at each occurrence thereof from halogen, cyano, C$_1$–C$_4$ alkyl, C$_1$–C$_4$ haloalkyl and C$_1$–C$_4$ alkoxy; or
R$^{11}$ and R$^{12}$ are taken together with the nitrogen to which they are attached to form piperidine, pyrrolidine, piperazine, N-methylpiperazine, morpholine or thiomorpholine rings.

Another embodiment of the invention is a compound of formulae IA-F, wherein:
R$^{13}$ is C$_1$–C$_4$ alkyl, C$_1$–C$_4$ haloalkyl or phenyl; and n is 0, 1, or 2.

Another embodiment of the invention is a compound of formulae IA-F, wherein:
substituents R$^1$–R$^8$ are as set forth in the following table:

TABLE A

| | IA | IB | IC | ID | IE | IF |
|---|---|---|---|---|---|---|
| R$^1$ | C$_1$–C$_6$ alkyl, C$_2$–C$_6$ alkenyl, C$_2$–C$_6$ alkynyl, C$_3$–C$_6$ cycloalkyl or C$_4$–C$_7$ cycloalkylalkyl, each of which is optionally substituted with from 1 to 3 substituents selected independently at each occurrence thereof from C$_1$–C$_3$ alkyl, halogen, aryl, —CN, —OR$^9$ and —NR$^9$R$^{10}$ | | | | | |
| R$^2$ | H, C$_1$–C$_6$ alkyl, C$_2$–C$_6$ alkenyl, C$_2$–C$_6$ alkynyl, C$_3$–C$_6$ cycloalkyl, C$_4$–C$_7$ cycloalkylalkyl or C$_1$–C$_6$ haloalkyl | | | | | |
| R$^3$ | C$_1$–C$_6$ alkyl, C$_2$–C$_6$ alkenyl, C$_2$–C$_6$ alkynyl, C$_3$–C$_6$ cycloalkyl or C$_4$–C$_7$ cycloalkylalkyl, each of which is optionally substituted as set forth above for the groups in R$^3$ of IC-IF | —O(phenyl), —O(benzyl), —OC(O)R$^{13}$, —S(O)$_n$R$^{12}$, - wherein, —O(phenyl) and —O(benzyl) are optionally substituted 1 to 3 times with cyano, halogen, C$_1$–C$_4$ alkyl, C$_1$–C$_4$ haloalkyl, or C$_1$–C$_4$ alkoxy | H, halogen, —OR$^{11}$, —S(O)$_n$R$^{12}$, —S(O)NR$^{11}$R$^{12}$, —CN, —C(O)R$^{12}$, —C(O)NR$^{11}$R$^{12}$, C$_1$–C$_6$ alkyl, C$_2$–C$_6$ alkenyl, C$_2$–C$_6$ alkynyl, C$_3$–C$_6$ cycloalkyl, C$_4$–C$_7$ cycloalkylalkyl, —O(phenyl), —O(benzyl) and —OC(O)R$^{13}$, wherein C$_1$–C$_6$ alkyl, C$_2$–C$_6$ alkenyl, C$_2$–C$_6$ alkynyl, C$_3$–C$_6$ cycloalkyl and C$_4$–C$_7$ cycloalkylalkyl are optionally substituted with 1 to 3 substituents selected independently at each occurrence thereof from C$_1$–C$_3$ alkyl, halogen, aryl, —CN, —OR$^9$ and —NR$^9$R$^{10}$ and wherein —(O)phenyl and —(O)benzyl are optionally substituted as described for these groups in R$^3$ of IB | | | |
| R$^4$ | H, halogen, —OR$^{11}$, —S(O)$_n$R$^{12}$, —S(O)NR$^{11}$R$^{12}$, —CN, —C(O)R$^{12}$, —C(O)NR$^{11}$R$^{12}$, —NR$^{11}$R$^{12}$, C$_1$–C$_6$ alkyl, C$_2$–C$_6$ alkenyl, C$_2$–C$_6$ alkynyl, C$_3$–C$_6$ cycloalkyl, C$_4$–C$_7$ cycloalkylalkyl, wherein C$_1$–C$_6$ alkyl, C$_2$–C$_6$ alkenyl, C$_2$–C$_6$ alkynyl, C$_3$–C$_6$ cycloalkyl and C$_4$–C$_7$ cycloalkylalkyl optionally substituted with from 1 to 3 substituents selected independently at each occurrence thereof from C$_1$–C$_3$ alkyl, halogen, aryl, —CN, —OR$^9$ and —NR$^9$R$^{10}$ | | C$_1$–C$_6$ alkyl, C$_2$–C$_6$ alkenyl, C$_2$–C$_6$ alkynyl, C$_3$–C$_6$ cycloalkyl, or C$_4$–C$_7$ cycloalkylalkyl, each optionally substituted as for R$^4$ in IA, IB, IE and IF | —O(phenyl), —O(benzyl), —OC(O)R$^{13}$, —NR$^{11}$R$^{12}$ or —S(O)$_n$R$^{12}$, —O(phenyl) and —O(benzyl) optionally substituted 1 to 3 times with cyano, halogen, C$_1$–C$_4$ alkyl, C$_1$–C$_4$ haloalkyl, or C$_1$–C$_4$ alkoxy | H, halogen, —OR$^{11}$, —S(O)$_n$R$^{12}$, —S(O)NR$^{11}$R$^{12}$, —CN, —C(O)R$^{12}$, —C(O)NR$^{11}$R$^{12}$, —NR$^{11}$R$^{12}$, C$_1$–C$_6$ alkyl, C$_2$–C$_6$ alkenyl, C$_2$–C$_6$ alkynyl, C$_3$–C$_6$ cycloalkyl, C$_4$–C$_7$ cycloalkylalkyl, wherein C$_1$–C$_6$ alkyl, C$_2$–C$_6$ alkenyl, C$_2$–C$_6$ alkynyl, C$_3$–C$_6$ cycloalkyl and C$_4$–C$_7$ cycloalkylalkyl optionally substituted with from 1 to 3 substituents selected independently at each occurrence thereof from C$_1$–C$_3$ alkyl, halogen, aryl, —CN, —OR$^9$ and —NR$^9$R$^{10}$ | |

TABLE A-continued

| | IA | IB | IC | ID | IE | IF |
|---|---|---|---|---|---|---|
| $R^5$ | H, halogen, $-OR^{11}$, $-S(O)_nR^{12}$, $-CN$, $-C(O)R^{12}$, $-NR^{11}R^{12}$, | | | | at least one of $R^5$ or $R^7$ is F, Cl, or Me; the other of $R^5$ or $R^7$ and $R^6$ are any of the groups described for $R^{5-7}$ in IA–ID. $R^5$, $R^6$ (or $R^6$, $R^7$) are $-O-C(R^{12})_2-O-$ only where $R^7$ (or $R^5$) is F, Cl, or Me | see $R^5$, $R^6$ and $R^7$ for IA, IB, IC and ID |
| $R^6$ | $-C(O)NR^{11}R^{12}$, $-NR^{11}C(O)R^{12}$, $-NR^{11}C(O)_2R^{12}$, | | | | | |
| $R^7$ | $-NR^{11}C(O)NR^{12}R^{13}$, $C_1-C_6$ alkyl, $C_2-C_6$ alkenyl, $C_2-C_6$ alkynyl, $C_3-C_6$ cycloalkyl or $C_4-C_7$ cycloalkylalkyl, wherein each of $C_1-C_6$ alkyl, $C_2-C_6$ alkenyl, $C_2-C_6$ alkynyl, $C_3-C_6$ cycloalkyl and $C_4-C_7$ cycloalkylalkyl is optionally substituted with from 1 to 3 substituents selected independently at each occurrence thereof from $C_1-C_3$ alkyl, halogen, aryl, $-CN$, $-OR^9$ and $-NR^9R^{10}$, or $R^5$ and $R^6$ or $R^6$ and $R^7$ may be $-O-C(R^{12})_2-O-$. | | | | | |
| $R^8$ | H, halogen, $-OR^{11}$ | | | | | halogen |

Preferred embodiments of this invention are compounds of formullae IA–IF, wherein:
  $R^1$ is $C_1-C_3$ alkyl;
  $R^2$ is H, $C_1-C_4$ alkyl or $C_1-C_6$ haloalkyl.

Preferred embodiments of this invention are compounds of formulae IA, IC, ID, IE and IF, wherein:
  $R^3$ is $C_1-C_4$ alkyl, $C_3-C_6$ cycloalkyl or $C_4-C_7$ cycloalkylalkyl, each of these groups being optionally substituted with from 1 to 3 substituents selected independently at each occurrence thereof from $C_1-C_3$ alkyl, halogen, aryl, $-CN$, $-OR^9$ and $-NR^9R^{10}$.

Preferred embodiments of this invention are compounds of formula IB, wherein:
  $R^3$ is $-O(phenyl)$ or $-O(benzyl)$, is optionally substituted from 1 to 3 times with a substituent selected independently at each occurrence thereof from halogen, cyano, $C_1-C_4$ alkyl, $C_1-C_4$ haloalkyl, or $C_1-C_4$ alkoxy.

Preferred embodiments of this invention are compounds of formulae IC, ID, IE and IF:
  wherein $R^3$ is $-O(phenyl)$ or $-O(benzyl)$, and is optionally substituted from 1 to 3 times with a substituent selected independently at each occurrence thereof from halogen, cyano, $C_1-C_4$ alkyl, $C_1-C_4$ haloalkyl, and $C_1-C_4$ alkoxy.

Preferred embodiments of this invention are compounds of formulae IC–IF, wherein:
  $R^3$ is H.

Preferred embodiments of this invention are compounds of formulae IA, IB, IC, IE and IF, wherein:
  $R^4$ is $C_1-C_4$ alkyl, $C_3-C_6$ cycloalkyl or $C_4-C_7$ cycloalkylalkyl, each of these groups being optionally substituted with from 1 to 3 substituents selected independently at each occurrence thereof from $C_1-C_3$ alkyl, halogen, aryl, $-CN$, $-OR^9$ and $-NR^9R^{10}$.

Preferred embodiments of this invention are compounds of formulae IA, IB, IE and IF, wherein:
  $R^4$ is H.

Preferred embodiments of this invention are compounds of formulae IA, IB, IE and IF, wherein:
  $R^4$ is $-NR^{11}R^{12}$, $-O(phenyl)$ or $-O(benzyl)$, each of these aryl groups being is optionally substituted from 1 to 3 times with a substituent selected independently at each occurrence thereof from halogen, cyano, $C_1-C_4$ alkyl, $C_1-C_4$ haloalkyl, or $C_1-C_4$ alkoxy.

Preferred embodiments of this invention are compounds of formulae IE and IF, wherein:
  $R^3$ and $R^4$ are both halogen.

Preferred embodiments of this invention are compounds of formulae IA, IB, IC, ID and IF, wherein:
  $R^5$, $R^6$ and $R^7$ are each H, halogen, $-OR^{11}$, $-NR^{11}R^{12}$, $C_1-C_6$ alkyl or $C_1-C_6$ alkyl optionally substituted with from 1 to 3 substituents selected independently at each occurrence thereof from $C_1-C_3$ alkyl, halogen, aryl, $-CN$, $-OR^9$ and $-NR^9R^{10}$.

Preferred embodiments of this invention are compounds of formulae IA, IB, IC, ID, IE and IF, wherein:
  $R^5$ is fluoro, chloro or methyl;
  one of $R^6$ or $R^7$ is H; and the other of $R^6$ or $R^7$ which is not H is halogen, $-OR^{11}$, $-NR^{11}R^{12}$, $C_1-C_6$ alkyl or $C_1-C_6$ alkyl each of which is optionally substituted with from 1 to 3 substituents selected independently at each occurrence thereof from $C_1-C_3$ alkyl, halogen, aryl, $-CN$, $-OR^9$ and $NR^9R^{10}$.

Preferred embodiments of this invention are compounds of formulae IA, IB, IC, ID and IE, wherein:
  $R^8$ is H or halogen.

Preferred embodiments of this invention are compounds of formula IF, wherein:
  $R^8$ is halogen.

Preferred embodiments of this invention are compounds of formulae IA, IB, IC, ID, IE and IF, wherein:
  the substituents $R^1-R^8$ are as set forth in the following table B:

TABLE B

| | IA | IB | IC | ID | IE | IF |
|---|---|---|---|---|---|---|
| $R^1$ | | | $C_1$–$C_3$ alkyl | | | |
| $R^2$ | | | H, $C_1$–$C_4$ alkyl or $C_1$–$C_6$ haloalkyl | | | |
| $R^3$ | $C_1$–$C_6$ alkyl, $C_3$–$C_6$ cycloalkyl or $C_4$$C_7$ cycloalkyl-alkyl, each optionally substituted | —O(phenyl) or —O(benzyl), each optionally substituted | H; or, alternatively, $C_1$–$C_6$ alkyl, $C_3$–$C_6$ cycloalkyl or $C_4$–$C_7$ cycloalkyl-alkyl, each optionally substituted, or —O(phenyl) or —O(benzyl), each optionally substituted | | | |
| $R^4$ | H; or, alternatively, $C_1$–$C_4$ alkyl, $C_3$–$C_6$ cycloalkyl or $C_4$–$C_7$ cycloalkyl-alkyl, each optionally substituted, —$NR^{11}R^{12}$; or, —(O)phenyl or —O(benzyl), each optionally substituted | $C_1$–$C_4$ alkyl, $C_3$–$C_6$ cycloalkyl or $C_4$–$C_7$ cycloalkyl-alkyl, each optionally substituted | —O(phenyl) or —O(benzyl), each optionally substituted | H; or, alternatively, $C_1$–$C_6$ alkyl, $C_3$–$C_6$ cycloalkyl or $C_4$–$C_7$ cycloalkyl-alkyl, each optionally substituted, $NR^{11}R^{12}$; or, —(O)phenyl or —O(benzyl), each optionally substituted | | |
| $R^5$ | H, halogen, —$OR^{11}$, —$NR^{11}R^{12}$, $C_1$–$C_6$ alkyl or $C_1$–$C_6$ alkyl optionally substituted | | | | F, Cl, Me | See $R^5$ for IA–ID |
| $R^6$, $R^7$ | H, halogen, —$OR^{11}$, —$NR^{11}R^{12}$, $C_1$–$C_6$ alkyl or $C_1$–$C_6$ alkyl optionally substituted | | | | one is H and the other is halogen, —$OR^{11}$, —$NR^{11}R^{12}$, $C_1$–$C_6$ alkyl or $C_1$–$C_6$ alkyl optionally substituted | See $R^6$, $R^7$ for IA–ID |
| $R^8$ | H, halogen, —$OR^{11}$ | | | | | halogen |

More preferred embodiments of this invention are compounds wherein:

$R^1$ is $C_1$–$C_3$ alkyl;
$R^2$ is H or $C_1$–$C_3$ alkyl;
$R^3$ is H, $C_1$–$C_4$ alkyl, —O(phenyl) or optionally substituted —O(phenyl), more preferably halogen;
$R^4$ is H, $C_1$–$C_4$ alkyl, —O(phenyl) or optionally substituted —O(phenyl), more preferably halogen;
$R_5$ is F, Cl or Me, more preferably —$OR^{11}$, wherein $R^{11}$ is $C_1$–$C_3$ alkyl;
$R^6$ is H or more preferably Cl, F, $C_1$–$C_3$ alkyl, halosubstituted $C_1$–$C_3$ alkyl, or —$OR^{11}$,
$R^{11}$ is $C_1$–$C_3$ alkyl or —$NR^{11}R^{12}$;
$R^7$ is H or more preferably Cl, F, $C_1$–$C_3$ alkyl or —$OR^{11}$, wherein $R^{11}$ is $C_1$–$C_3$ alkyl.

A further more preferred embodiments of this invention are compounds wherein:

$R^1$ is $CH_3$;
$R^2$ is H or $CH_3$;
$R^3$ is H, $CH_3$, or —O(phenyl) or —O—$CH_2$— (phenyl), each of said —O(phenyl) or —O—$CH_2$— (phenyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;
$R^4$ is H, F, $CH_3$, $CH_2CH_3$, $CH_2CH_2CH_3$, $CH_2CH(CH_3)$ $CH_3$, —O(phenyl) or —O—$CH_2$-phenyl, where each of said —O(phenyl) or —O—$CH_2$— (phenyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;
$R^5$ is H, $CH_3$, $OCH_3$, F or Cl;
$R^6$ is H, $CH_3$, —$OCH_3$, F, Cl or $CF_3$;
$R^7$ is H, F, Cl, $CH_3$ or $OCH_3$; and
$R^8$ is halogen.

A further more preferred embodiments of this invention are compounds of formulae IA–IF, wherein: $R^1$–$R^8$ are as follows:

TABLE C

| $R^1$ | $R^2$ | $R^3$ | $R^4$ | $R^5$ | $R^6$ | $R^7$ | $R^8$ |
|---|---|---|---|---|---|---|---|
| Me | H | H | Me | H | H | H | H |
| Me | H | H | Me | H | OMe | H | H |
| Me | H | H | Me | H | F | H | H |
| Me | H | H | Me | F | H | H | H |
| Me | H | H | Me | F | F | H | H |
| Me | H | H | Me | Me | F | H | H |
| Me | H | H | Me | Cl | F | H | H |
| Me | H | H | Me | Cl | H | H | H |
| Me | H | H | Me | H | Me | H | H |
| Me | H | H | Me | F | Me | H | H |
| Me | H | H | Me | H | Cl | H | H |
| Me | H | H | Me | F | Cl | H | H |
| Me | H | H | Me | Cl | Cl | H | H |
| Me | H | H | Et | H | H | H | H |

TABLE C-continued

| R¹ | R² | R³ | R⁴ | R⁵ | R⁶ | R⁷ | R⁸ |
|---|---|---|---|---|---|---|---|
| Me | H | H | Et | F | F | H | H |
| Me | H | H | F | H | OMe | H | H |
| Me | H | H | F | F | OMe | H | H |
| Me | H | H | F | F | Me | H | H |
| Me | H | H | F | F | Cl | H | H |
| Me | H | H | F | F | F | H | H |
| Me | H | H | F | Cl | H | H | H |
| Me | H | H | CN | H | H | H | H |
| Me | H | H | CF₃ | H | H | H | H |
| Me | Me | H | Me | H | H | H | H |
| Me | Me | H | H | H | Cl | H | H |
| Me | Me | H | H | F | F | H | H |
| Me | H | Me | Me | H | H | H | H |
| Me | H | F | Me | H | H | H | H |
| Me | H | Me | F | H | H | H | H |
| Me | H | OMe | Me | H | H | H | H |
| Me | H | OH | Me | H | H | H | H |
| Me | H | H | OCF₃ | H | H | H | H |
| Me | H | H | OMe | F | F | H | H |
| Me | H | H | OMe | Me | F | H | H |
| Me | H | H | OMe | F | Me | H | H |
| Me | H | H | OMe | Me | H | H | H |
| Me | H | H | O(Ph) | H | H | H | H |
| Me | H | H | O(4-OMePh) | H | H | H | H |
| Me | H | H | O(CH₂Ph) | H | H | H | H |
| Me | H | H | OH | Me | H | H | H |
| Me | H | H | OH | F | Me | H | H |
| Me | H | H | OH | Me | F | H | H |
| Me | H | H | OH | F | F | H | H |
| Me | H | H | H | CN | H | H | H |
| Me | H | Me | H | H | H | H | H |
| Me | H | Me | H | H | F | H | H |
| Me | H | Me | H | F | F | H | H |
| Me | H | Me | H | F | H | F | H |
| Me | H | Me | H | F | H | H | H |
| Me | H | Me | H | Me | F | H | H |
| Me | H | Me | H | Cl | F | H | H |
| Me | H | Me | H | Cl | Cl | H | H |
| Me | H | Me | H | Cl | H | H | H |
| Me | H | Me | H | H | Cl | H | H |
| Me | H | Me | H | F | Cl | H | H |
| Me | H | Me | H | H | OMe | H | H |
| Me | H | Me | H | H | CN | H | H |
| Me | H | Me | H | H | CF₃ | H | H |
| Me | H | Me | H | H | Me | H | H |
| Me | H | CH₂NHMe | H | H | H | H | H |
| Me | H | CH₂OH | H | H | H | H | H |
| Me | H | SO₂NH₂ | H | H | H | H | H |
| Me | H | SO₂NHMe | H | H | H | H | H |
| Me | H | OMe | H | H | Me | H | H |
| Me | H | OMe | H | F | H | F | H |
| Me | H | OMe | H | Cl | H | H | H |
| Me | H | OMe | H | Cl | Cl | H | H |
| Me | H | OMe | H | F | Cl | H | H |
| Me | H | OMe | H | Cl | F | H | H |
| Me | H | H | H | F | H | F | H |
| Me | H | H | H | F | H | Cl | H |
| Me | H | Me | H | F | H | F | H |
| Me | H | Me | H | F | H | Cl | H |
| Me | H | H | H | F | F | F | H |
| Me | H | H | H | F | Me | H | H |
| Me | H | H | H | Me | F | H | H |
| Me | H | H | H | F | F | H | H |
| Me | H | H | H | Cl | H | H | H |
| Me | H | H | H | F | Cl | H | H |
| Me | H | H | H | Cl | F | H | H |
| Me | H | H | H | CN | H | H | H |
| Me | H | H | H | H | NHCOMe | H | H |
| Me | H | H | H | H | Cl | H | F |
| Me | Me | H | Me | F | H | F | H |
| Me | H | H | Me | F | F | F | H |
| Et | H | H | Me | F | F | H | H |
| Me | H | H | Me | H | F | H | OH |
| Me | H | F | CH₂Me | H | H | H | H |
| Me | H | H | CH₂NH₂ | H | H | H | H |
| Me | H | H | CH₂NHMe | H | H | H | H |
| Me | H | OH | CN | H | H | H | H |
| Me | H | H | CH₂OH | H | H | H | H |
| Et | H | H | H | H | H | H | H |

That is, the specifically preferred compounds are:
2,7-dimethyl-4-phenyl-1,2,3,4-tetrahydroisoquinoline;
4-(4-methoxy)phenyl-2,7-dimethyl-1,2,3,4-tetrahydroisoquinoline;
2,7-dimethyl-4-(4-fluoro)phenyl-1,2,3,4-tetrahydroisoquinoline;
2,7-dimethyl-4-(3-fluoro)phenyl-1,2,3,4-tetrahydroisoquinoline;
4-(3,4-difluoro)phenyl-2,7-dimethyl-1,2,3,4-tetrahydroisoquinoline;
2,7-dimethyl-4-(4-fluoro-3-methyl)phenyl-1,2,3,4-tetrahydroisoquinoline;
4-(3-chloro-4-fluoro)phenyl-2,7-dimethyl-1,2,3,4-tetrahydroisoquinoline;
4-(3-chloro)phenyl-2,7-dimethyl-1,2,3,4-tetrahydroisoquinoline;
2,7-dimethyl-4-(4-methyl)phenyl-1,2,3,4-tetrahydroisoquinoline;
2,7-dimethyl-4-(3-fluoro-4-methyl)phenyl-1,2,3,4-tetrahydroisoquinoline;
4-(4-chloro)phenyl-2,7-dimethyl-1,2,3,4-tetrahydroisoquinoline;
4-(4-chloro-3-fluoro)phenyl-2,7-dimethyl-1,2,3,4-tetrahydroisoquinoline;
4-(3,4-dichloro)phenyl-2,7-dimethyl-1,2,3,4-tetrahydroisoquinoline;
7-ethyl-2-methyl-4-phenyl-1,2,3,4-tetrahydroisoquinoline;
4-(3,4-difluoro)phenyl-7-ethyl-2-methyl-1,2,3,4-tetrahydroisoquinoline;
7-fluoro-4-(4-methoxy)phenyl-2-methyl-1,2,3,4-tetrahydroisoquinoline;
7-fluoro-4-(3-fluoro-4-methoxy)phenyl-2-methyl-1,2,3,4-tetrahydroisoquinoline;
7-fluoro-4-(3-fluoro-4-methyl)phenyl-2-methyl-1,2,3,4-tetrahydroisoquinoline;
7-fluoro-4-(4-chloro-3-fluoro)phenyl-2-methyl-1,2,3,4-tetrahydroisoquinoline;
4-(3,4-difluoro)phenyl-7-fluoro-2-methyl-1,2,3,4-tetrahydroisoquinoline;
4-(3-chloro)phenyl-7-fluoro-2-methyl-1,2,3,4-tetrahydroisoquinoline;
7-cyano-2-methyl-4-phenyl-1,2,3,4-tetrahydroisoquinoline;
2-methyl-4-phenyl-7-trifluoromethyl-1,2,3,4-tetrahydroisoquinoline;
4-phenyl-1,2,7-trimethyl-1,2,3,4-tetrahydroisoquinoline;
4-(4-chloro)phenyl-1,2-dimethyl-1,2,3,4-tetrahydroisoquinoline;
4-(3,4-difluoro)phenyl-1,2-dimethyl-1,2,3,4-tetrahydroisoquinoline;
4-phenyl-2,7,8-trifluoromethyl-1,2,3,4-tetrahydroisoquinoline;
2,7-dimethyl-8-fluoro-4-phenyl-1,2,3,4-tetrahydroisoquinoline;
2,8-dimethyl-7-fluoro-4-phenyl-1,2,3,4-tetrahydroisoquinoline;
2,7-dimethyl-8-methoxy-4-phenyl-1,2,3,4-tetrahydroisoquinoline;

2,7-dimethyl-8-hydroxy-4-phenyl-1,2,3,4-tetrahydroisoquinoline;
2-methyl-4-phenyl-7-trifluoromethoxy-1,2,3,4-tetrahydroisoquinoline;
4-(3,4-difluoro)phenyl-7-methoxy-2-methyl-1,2,3,4-tetrahydroisoquinoline;
4-(4-fluoro-3-methyl)phenyl-7-methoxy-2-methyl-1,2,3,4-tetrahydroisoquinoline;
4-(3-fluoro-4-methyl)phenyl-7-methoxy-2-methyl-1,2,3,4-tetrahydroisoquinoline;
7-methoxy-4-(3-methyl)phenyl-2-methyl-1,2,3,4-tetrahydroisoquinoline;
2-methyl-7-phenoxy-4-phenyl-1,2,3,4-tetrahydroisoquinoline;
7-(4-methoxy)phenoxy-2-methyl-4-phenyl-1,2,3,4-tetrahydroisoquinoline;
7-benzyloxy-2-methyl-4-phenyl-1,2,3,4-tetrahydroisoquinoline;
7-hydroxy-2-methyl-4-(3-methyl)phenyl-1,2,3,4-tetrahydroisoquinoline;
4-(3-fluoro-4-methyl)phenyl-7-hydroxy-2-methyl-1,2,3,4-tetrahydroisoquinoline;
4-(4-fluoro-3-methyl)phenyl-7-hydroxy-2-methyl-1,2,3,4-tetrahydroisoquinoline;
4-(3,4-difluoro)phenyl-7-hydroxy-2-methyl-1,2,3,4-tetrahydroisoquinoline;
4-(3-cyano)phenyl-2-methyl-1,2,3,4-tetrahydroisoquinoline;
2,8-dimethyl-4-phenyl-1,2,3,4-tetrahydroisoquinoline;
2,8-dimethyl-4-(4-fluoro)phenyl-1,2,3,4-tetrahydroisoquinoline;
4-(3,4-difluoro)phenyl-2,8-dimethyl-1,2,3,4-tetrahydroisoquinoline;
4-(3,5-difluoro)phenyl-2,8-dimethyl-1,2,3,4-tetrahydroisoquinoline;
2,8-dimethyl-4-(3-fluoro)phenyl-1,2,3,4-tetrahydroisoquinoline;
2,8-dimethyl-4-(4-fluoro-3-methyl)phenyl-1,2,3,4-tetrahydroisoquinoline;
4-(3-chloro-4-fluoro)phenyl-2,8-dimethyl-1,2,3,4-tetrahydroisoquinoline;
4-(3,4-dichloro)phenyl-2,8-dimethyl-1,2,3,4-tetrahydroisoquinoline;
4-(3-chloro)phenyl-2,8-dimethyl-1,2,3,4-tetrahydroisoquinoline;
4-(4-chloro)phenyl-2,8-dimethyl-1,2,3,4-tetrahydroisoquinoline;
4-(4-chloro-3-fluoro)phenyl-2,8-dimethyl-1,2,3,4-tetrahydroisoquinoline;
2,8-dimethyl-4-(4-methoxy)phenyl-1,2,3,4-tetrahydroisoquinoline;
4-(4-cyano)phenyl-2,8-dimethyl-1,2,3,4-tetrahydroisoquinoline;
2,8-dimethyl-4-(4-trifluoromethyl)phenyl-1,2,3,4-tetrahydroisoquinoline;
2,8-dimethyl-4-(4-methyl)phenyl-1,2,3,4-tetrahydroisoquinoline;
2-methyl-8-(N-methylamino)methyl-4-phenyl-1,2,3,4-tetrahydroisoquoinoline;
8-(hydroxy)methyl-2-methyl-4-phenyl-1,2,3,4-tetrahydroisoquinoline;
2-methyl-4-phenyl-8-sulfonamide-1,2,3,4-tetrahydroisoquinoline;
2-methyl-8-(N-methyl)sulfonamide-4-phenyl-1,2,3,4-tetrahydroisoquinoline;
8-methoxy-2-methyl-4-(4-methyl)phenyl-1,2,3,4-tetrahydroisoquinoline;
4-(3,5-difluoro)phenyl-8-methoxy-2-methyl-1,2,3,4-tetrahydroisoquinoine;
4-(3-chloro)phenyl-8-methoxy-2-methyl-1,2,3,4-tetrahydroisoquinoline;
4-(3,4-dichloro)phenyl-8-methoxy-2-methyl-1,2,3,4-tetrahydroisoquinoline;
4-(4-chloro-3-fluoro)phenyl-8-methoxy-2-methyl-1,2,3,4-tetrahydroisoquinoline;
4-(3-chloro-4-fluoro)phenyl-8-methoxy-2-methyl-1,2,3,4-tetrahydroisoquinoline;
4-(3,5-difluoro) phenyl-2-methyl-1, 2,3,4-tetrahydroisoquinoline;
4-(3-chloro-5-fluoro)phenyl-2-methyl-1,2,3,4-tetrahydroisoquinoline;
4-(3,5-difluoro)phenyl-2,7-dimethyl-1,2,3,4-tetrahydroisoquinoline;
4-(3-chloro-5-fluoro)phenyl-2,7-dimethyl-1,2,3,4-tetrahydroisoquinoline;
2-methyl-4-(3,4,5-trifluoro)phenyl-1, 2,3,4-tetrahydroisoquinoline;
2–4-(3-fluoro)phenyl-2-methyl-1, 2,3,4-tetrahydroisoquinoline;
4-(3-fluoro-4-methyl)phenyl-2-methyl-1,2,3,4-tetrahydroisoquinoline;
4-(4-fluoro-3-methyl)phenyl-2-methyl-1,2,3,4-tetrahydroisoquinoline;
4-(3,4-difluoro) phenyl-2-methyl-1, 2,3,4-tetrahydroisoquinoline;
4-(3-chloro)phenyl-2-methyl-1,2,3,4-tetrahydroisoquinoline;
4-(4-chloro)3-fluoro)phenyl-2-methyl-1,2,3,4-tetrahydroisoquinoline;
4-(3-chloro-4-fluoro)phenyl-2-methyl-1,2,3,4-tetrahydroisoquinoline;
4-(3-cyano)phenyl-1-2-methyl-1-1,2,3,4-tetrahydroisoquinoline;
4-(4-acetanilide)-2-methyl-1,2,3,4-tetrahydroisoquinoline;
4-(4-chloro)phenyl-4-fluoro-2-methyl-1,2,3,4-tetrahydroisoquinoline;
(3,5-difluoro)-4-phenyl-1,2,7-trimethyl-1,2,3,4-tetrahydroisoquinoline;
(8-fluoro-2-methyl-4-phenyl-1,2,3,4-tetrahydro-7-isoquinolinyl)-N-methylmethanamine;
(2-methyl-4-phenyl-7-isoquinolinyl)-N-methylmethanamine;
N-methyl(2-methyl-4-phenyl-7-isoquinolinyl)-N-methylmethanamine;
8-hydroxy-2-methyl-4-phenyl-1,2,3,4-tetrahydro-7-isoquinolinecarbonitrile;
(2-methyl-4-phenyl-1,2,3,4-tetrahydro-7-isoquinolinyl) methanol; and
2-ethyl-4-phenyl-1,2,3,4-tetrahydroisoquinoline; or an oxide thereof, a pharmaceutically acceptable salt thereof, a solvate thereof, or prodrug thereof.

Further more preferred compound of this invention include those (+) enantiomers of compounds of formulae IA–IF, selected from table D:

TABLE D

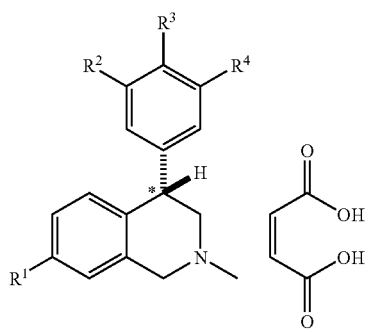

| Ex. | R¹ | R² | R³ | R⁴ | Chiral Technologies Column | % IPA in Hexanes | Peak Order | Mp (° C.) |
|---|---|---|---|---|---|---|---|---|
| 1 | H | H | Me | F | Chiralcel ® OD | 10 | 1st | 190.0–190.5 |
| 2 | OMe | H | F | F | Chiralpak ® AD | 10 | 2nd | 160.0–163.5 |
| 3 | Me | H | F | F | Chiralpak ® AD | 2.5 | 2nd | 136.0–138.0 |
| 4 | H | H | Cl | F | Chiralcel ® OD | 10 | 1st | 171.0–172.0 |
| 5 | H | H | F | F | Chiralcel ® OD | 10 | 1st | 138.0–139.0 |
| 6 | Me | F | H | F | Chiralpak ® AD | 10 | 2nd | 174.0–175.0 |
| 7 | Me | H | F | H | Chiralpak ® AD | 10 | 2nd | 144.5–146.0 |
| 8 | Me | H | H | F | Chiralpak ® AD | 10 | 2nd | 172.0–173.5 |

Another preferred aspect of the invention is a mixture of compounds of formulae (IA-F) wherein the compound of formulae (IA-F) is radiolabeled, i.e., wherein one or more of the atoms described are replaced by a radioactive isotope of that atom (e.g., C replaced by $^{14}$C and H replaced by $^{3}$H). Such compounds have a variety of potential uses, e.g., as standards and reagents in determining the ability of a potential pharmaceutical to bind to neurotransmitter proteins.

Another aspect of the invention is a therapeutically effective amount of the compound of formulae (IA-F) and a pharmaceutically acceptable carrier.

Another aspect of the invention is a method of treating a disorder which is created by or is dependent upon decreased availability of serotonin, norepinephrine or dopamine, which comprises administering to a patient in need of such treatment a therapeutically effective amount of a compound of formulae (IA-F), or a pharmaceutically acceptable salt thereof.

Another aspect of the invention is a method of treating a disorder which is created by or is dependent upon decreased availability of serotonin, norepinephrine or dopamine, which comprises administering to a patient in need of such treatment a therapeutically effective amount of a compound of formulae (IA-F), or a pharmaceutically acceptable salt thereof and a therapeutically effective amount of a serotonin IA receptor antagonist, or pharmaceutically acceptable salt thereof.

Another aspect of the invention is a method of treating a disorder which is created by or is dependent upon decreased availability of serotonin, norepinephrine or dopamine, which comprises administering to a patient in need of such treatment a therapeutically effective amount of a compound of formulae (IA-F), or a pharmaceutically acceptable salt thereof and a therapeutically effective amount of a compound selected from the group consisting of WAY 100135 and spiperone, or pharmaceutically acceptable salt thereof.

WAY 100135 (N-(t-butyl)-3-[a-(2-methoxyphenyl)piperazin-1-yl]-2-phenylpropanamide) is disclosed in Abou-Gharbia et al., U.S. Pat. No. 4,988,814, as having an affinity for the 5-HT$_{1A}$ receptor. Also, Cliffe et al., J. Med. Chem. 36, 1509–10 (1993) showed that the compound is a 5-HT$_{1A}$ antagonist. Spiperone (8-[4-(4-fluorophenyl)-4-oxobutyl]-1-phenyl-1,3,8-triazaspiro[4,5]decan-4-one) is a well-known compound, and is diclosed in U.S. Pat. Nos. 3,155,669 and 3,155,670. The activity of Spiperone as a 5-HT$_{1A}$ antagonist is shown in Middlemiss et al., Neurosci. and Biobehav. Rev. 16, 75–82 (1992).

Another aspect of the invention is a method of treating a disorder which is created by or is dependent upon decreased availability of serotonin, norepinephrine or dopamine, which comprises administering to a patient in need of such treatment a therapeutically effective amount of a compound of formulae (IA-F), or a pharmaceutically acceptable salt thereof and a therapeutically effective amount of a selective neurokinin-1 receptor antagonist, or pharmaceutically acceptable salt thereof.

Neurokinin-1 receptor antagonists of use in combination a compound of formulae (IA-F) in the present invention, are fully described, for example, in U.S. Pat. Nos. 5,373,003, 5,387,595, 5,459,270, 5,494,926, 5,162,339, 5,232,929, 5,242,930, 5,496,833, 5,637,699; PCT International Patent Publication Nos. WO 90/05525, 90/05729, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767,94/15903, 94/19320, 94/19323, 94/20500, 91/09844, 91/18899, 92/01688, 92/06079, 92/12151,92/ 15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in U.K. Patent Application Nos. 2 266 529, 2 268 931, 2 269 170, 2 269 590, 2 271 774, 2 292 144, 2 293 168, 2 293 169, and 2 302 689, European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0610 793, 0 634 402, 0 686 629, 0 693 489, 0 694 535, 0 699 655, 0 394 989, 0 428 434, 0 429 366, 0 430 771, 0 436 334, 0 443 132, 0482 539, 0498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0 733 632 and 0 776 893. The preparation of such compounds are fully described in the aforementioned patents and publications.

Another aspect of the invention is a method of treating a disorder which is created by or is dependent upon decreased availability of serotonin, norepinephrine or dopamine, which comprises administering to a patient in need of such treatment a therapeutically effective amount of a compound of formulae (IA-F), or a pharmaceutically acceptable salt thereof and a therapeutically effective amount of a norepinephrine precursor, or pharmaceutically acceptable salt thereof.

Another aspect of the invention is a method of treating a disorder which is created by or is dependent upon decreased availability of serotonin, norepinephrine or dopamine, which comprises administering to a patient in need of such treatment a therapeutically effective amount of a compound of formulae (IA-F), or a pharmaceutically acceptable salt thereof and a therapeutically effective amount of a compound selected from L-tyrosine and L-phenylalanine, or pharmaceutically acceptable salt thereof.

Another aspect of the invention is a method of treating a disorder referred to in the above-mentioned embodiments, wherein the disorder is selected from the group: attention deficit disorder, hyperactivity disorder, anxiety, depression, post-traumatic stress disorder, supranuclear palsy, eating disorders, obsessive compulsive disorder, analgesia, nicotine addiction, panic attacks, Parkinsonism and phobia, obesity, late luteal phase syndrome or narcolepsy, cocaine addiction, amphetamine addiction, and psychiatric symptoms anger such as, rejection sensitivity, and lack of mental or physical energy.

Another aspect of the invention is a method of inhibiting synaptic norepinephrine uptake in a patient in need thereof comprising administering a therapeutically effective inhibitory amount of a compound of formulae (IA-F).

Another aspect of the invention is a method of inhibiting synaptic serotonin uptake in a patient in need thereof comprising administering a therapeutically effective inhibitory amount of a compound of formulae (IA-F).

Another aspect of the invention is a method of inhibiting synaptic dopamine uptake in a patient in need thereof comprising administering a therapeutically effective inhibitory amount of a compound of formulae (IA-F).

Another aspect of the invention is a therapeutic method described herein wherein the (+)—stereoisomer of the compound of formulae (IA-F) is employed.

Another aspect of the invention is a therapeutic method described herein wherein the (−)—stereoisomer of the compound of formulae (IA-F) is employed.

Another aspect of the invention is a kit comprising a compound of formulae (IA-F) and at least one compound selected from the group consisting of: a serotonin IA receptor antagonist compound, a selective neurokinin-1 receptor antagonist compound, and a norepinephrine precursor compound.

Another aspect of the invention is a method of treating depression in a patient in need thereof comprising inhibiting synaptic serotonin and norepinephrine uptake by administering a therapeutically effective inhibitory amount of a compound of formulae (IA-F) which functions as both a serotonin and norepinephrine uptake inhibitor.

Another aspect of the invention is a method of treating depression in a patient in need thereof comprising inhibiting synaptic serotonin and dopamine uptake by administering a therapeutically effective inhibitory amount of a compound of formulae (IA-F) which functions as both a serotonin and dopamine uptake inhibitor.

Another aspect of the invention is a method of treating depression in a patient in need thereof comprising inhibiting synaptic dopamine and norepinephrine uptake by administering a therapeutically effective inhibitory amount of a compound of formulae (IA-F) which functions as both a dopamine and norepinephrine uptake inhibitor.

Another aspect of the invention is a method for inhibiting serotonin uptake in mammals which comprises administering to a mammal requiring increased neurotransmission of serotonin a pharmaceutically effective amount of a compound of formulae (IA-F).

Another aspect of the invention is a method for inhibiting dopamine uptake in patients which comprises administering to a mammal requiring increased neurotransmission of dopamine a pharmaceutically effective amount of a compound of formulae (IA-F).

Another aspect of the invention is a method for inhibiting norepinephrine uptake in patients which comprises administering to a mammal requiring increased neurotransmission of norepinephrine a pharmaceutically effective amount of a compound of formulae (IA-F).

Another aspect of the invention is a method of suppressing the desire of humans to smoke comprising administering to a human in need of such suppression an effective dose, to relieve the desire to smoke, of a compound of formulae (IA-F).

Another aspect of the invention is a method of suppressing the desire of humans to consume alcohol comprising administering to a human in need of such suppression an effective dose, to relieve the desire to consume alcohol, of a compound of formulae (IA-F).

It is appreciated that certain features of the invention, which are, for clarity, described in the context of separate embodiments, may also be provided in combination in a single embodiment. Conversely, various features of the invention which are, for brevity, described in the context of a single embodiment, may also be provided seperately or in any suitable subcombination.

Preparation of Compounds of the Invention

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by R. C. Larock in Comprehensive Organic Transformations, VCH publishers, 1989.

A compound of formulae (IA-F) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

Compounds provided herein are synthesized, for example, using the methods described below (see Schemes 1–4), together with methods known in the art of synthetic organic chemistry, or variations thereon as appreciated by those skilled in the art. Preferred methods include, but are not limited to, those methods described below.

Compounds of formulae (IA-F) of this invention are, for example, prepared according to Scheme 1. Treatment of an optionally substituted acetophenone of formula (II) with common brominating agents such as, but not limited to, bromine, NBS, or tetrabutylammonium tribromide readily affords the desired bromoacetophenones of formula (III, X=Br). These reactions are optimally conducted in acetic acid or methylene chloride with methanol used as a co-solvent for the tribromide reagent with reaction temperatures at or below room temperature. Another embodiment of this methodology would include compounds of formula (III, X=Cl).

The acetophenones of formula (II) are available from commercial sources or are conveniently obtained via several well known methods, including the treatment of the corresponding benzoic acid intermediates with two stoichiometric equivalents of methyllithium as thoroughly described in the review of Jorgenson, M. J. (*Organic Reactions,* 1970, 18, pg. 1). Alternatively, one may treat the corresponding benzaldehydes with an alkyl-Grignard (for example, MeMgBr) or alkyl-lithium (for example, MeLi) nucleophile follwed by routine oxidation to the ketone as well demonstrated by Larock, R. C. (*Comprehensive Organic Transformations, VCH Publishers, New York,* 1989, p. 604).

Treatment of intermediates of formula (III) with intermediates of formula $(R^3,R^4\text{-Ph})$—$CH(R^2)$—$NHR^1$ cleanly generates the alkylation products of formula (V). The alkylation reactions may be run under a wide variety of conditions familiar to one skilled in the art of organic synthesis. Typical solvents include acetonitrile, toluene, diethyl ether, tetrahydrofuran, dimethylsulfoxide, dimethylformamide, methylene chloride, and lower alkyl alcohols including ethanol. The reactions may be successfully run at temperatures ranging from 0° C. up to the boiling point of the solvent employed. Reaction progress is conventionally determined by standard chromatographic and spectroscopic methods. The alkylation reaction is optionally run with the addition of a non-nucleophilic organic base such as, but not limited to, pyridine, triethylamine and diisopropyl ethylamine.

The $R^1$-substituted N-benzyl amines of formula $(R^3,R^4\text{-Ph})$-$CH(R^2)$—$NHR1$ may be purchased from commercial sources, or alternatively, obtained from a simple reductive amination protocol. Thus, carbonyl containing compounds of Formulae (IV, Scheme 1) may be treated with $H_2N$—$R^1$ in lower alkyl alcoholic solvents (preferably methanol) at temperatures at or below room temperature. The resulting imine may be reduced most commonly with alkaline earth borohydrides (preferably sodium borohydride) to provide the desired amine intermediate.

Reductions of compounds of formula (V) to the benzyl alcohols of formula (VI) proceeds with many reducing agents including, as example, sodium borohydride, lithium borohydride, borane, diisobutylaluminum hydride, and lithium aluminum hydride. The reductions are carried out for a period of time between 1 hour to 3 days at room temperature or elevated temperature up to the reflux point of the solvent employed. If borane is used, it may be employed as a complex for example, but not limited to, borane-methyl sulfide complex, borane-piperidine complex, borane-tetrahydrofuran complex. One skilled in the art will understand the optimal combination of reducing agents and reaction conditions needed or may seek guidance from the text of Larock, R. C. (*Comprehensive Organic Transformations,* VCH Publishers, New York, 1989, p. 527).

Compounds of formula (VI) may be cyclized to the target compounds of formulae IA–IF of this invention by brief treatment with a strong acid. Suitable acids include, but are not limited to, concentrated sulfuric acid, polyphosphoric acid, methanesulfonic acid and trifluoroacetic acid. The reactions are run neat or in the optional presence of a co-solvent such as, for example, methylene chloride and 1,2-dichloroethane. The cyclizations may be conducted at temperatures ranging from 0° C. up to the reflux point of the solvent employed. One skilled in the art of heterocyclic chemistry will readily understand these conditions or may consult the teachings of Mondeshka, et al. (ll Farmaco, 1994, 49, 475–480) or Venkov, et al. (*Synthesis,* 1990, 253–255). Cyclizations may also be effected by treatment of compounds of formula (VI) with strong Lewis Acids, such as for example, aluminum trichloride typically in halogenated solvents such as methylene chloride. One skilled in the art will be familiar with the precedent taught by Kaiser, et al. (*J. Med. Chem.,* 1984, 27, 28–35) and Wyrick, et al. (*J. Med. Chem.,* 1981, 24, 1013–1015).

Compounds of formulae IA–IF may be obtained in enantiomerically pure (R) and (S) form by crystallization with chiral salts as well known to one skilled in the art, or alternatively, may be isolated through chiral HPLC employing commercially available chiral columns.

Alternatively, compounds of formulae (V) and (VI) may be arrived at as described in Scheme 2. Thus, the haloacetophenones of formula may be treated with simple amines of formula $H_2N-R^1$ under alkylation conditions as described above (vide supra) to provide compounds of formulae (VII). A second alkylation may then be performed utilizing reagents of formula (VIII) where X represents a leaving group, such as for example, but not limited to, halogen, mesylate, or tosylate to afford the common intermediate of formula (V). Reagents of formula (VIII) are in turn available from the appropriately substituted carbonyl compound of formula (IV) via reduction (vide supra) and activation.

Activation to leaving group X is effected by treatment of the alcohol with methanesulfonyl chloride or p-toluenesulfonyl chloride in the presence of a non-nucleophilic base such as, but not limited to, 1,5-diazabicyclo[4.3.0]non-5-ene (DBN), pyridine or triethylamine. The reaction is commonly performed in halogenated organic solvent, for example, methylene chloride, and at temperatures from $-78°$ C. up to the boiling point of the solvent employed. Benzylic activation to Leaving Group X may also be effected by treatment with halogenating agents such as, but not limited to, $SO_2Cl_2$, $Cl_2$, $PCl_5$, $Br_2$, $CuBr_2$, NBS, and $CBr_4$. The various conditions necessary to accomplish this transformation will be readily apparent to those skilled in the art of organic chemistry and additional reference on benzylic activiation may be sought from Larock, R. C. (*Comprehensive Organic Transformations*, VCH Publishers, New York, 1989, p. 313).

The flexibility of the synthesis is further demonstrated by an alternative sequence of reactions, wherein (VII) may be reduced (vide supra) and either i) alkylated as above with (VIII) to afford (VI) or ii) condensed with (IV) followed by in-situ imine reduction to also afford (VI). Where $R^5=R^6=R^7=H$, and the (methylaminomethyl)benzyl alcohol derivative may be obtained from commercial sources.

Compounds of formulae IA–IF of this invention may also be prepared according to Scheme 3. Treatment of an appropriately substituted 2-iodobenzaldehyde (or a 2-bromobenzaldehyde) (X) with an amine $H_2N-R^1$ in lower alkyl alcohol solvents followed by reduction of the resultant imine as described above in Scheme I (vide supra) affords an intermediate (2-I or Br),$R^2$,$R^3$-PhCH$_2$—NH—$R^1$ which, when treated with an optionally substituted bromoacetophenone (as described for the synthesis of (V), Scheme 1) provides the alkylation product (XI).

Compounds of formula (XI) may be treated with strong bases, such as, but not limited to lower alkyl ($C_{1-6}$) lithium bases (preferably t-BuLi or n-BuLi) to afford the anticipated halogen-metal exchange followed by intramolecular Barbier cyclization to generate compounds of formulae (IA–IE, $R^8$=OH). Inert solvents such as dialkyl ethers (preferably diethyl ether), cyclic ethers (preferably tetrahydrofuran or 1,4-dioxane), etc. are necessary, and reaction temperatures are kept low ($-78°$ C. to $-25°$ C.) to avoid by-products. Alternatively, halogen-metal exchange may also be effected in the presence of zerovalent nickel, in which case N,N-dialkylformamides (preferably dimethylformamide) serve as ideal solvents. One skilled in the art of organic synthesis will understand the optimal combination of conditions and may seek further reference from Kihara, et al. (*Tetrahedron*, 1992, 48, 67–78), and Blomberg, et al. (*Synthesis*, 1977, p. 18–30). Additionally, compounds of formulae (IA-E, $R^8$=OH) may be readily alkylated (vide supra) to afford compounds formulae (IA-E, $R^8$=OR$^{11}$). Finally, further treatment of compounds of formulae (IA-E, $R^8$=OH) with a halogenating reagent or specifically a fluorinating reagent such as, but not limited to, diethylaminosulfur trifluoride (DAST), readily provides compounds of formulae (IA-F, $R^8$=F). Further reference may be gained from the review of Hudlicky (*Organic Reactions*, 1985, 35, p. 513–637).

Compounds of formulae IA-F of this invention may also be prepared according to Scheme 4. 4-Bromoisoquinolines (XII) may be treated with an aryl boronic acid or aryl boronic acid ester where Y is equivalent to $B(OH)_2$ or $B(OR^a)(OR^b)$ (where $R^a$ and $R^b$ are lower alkyl, ie. $C_1$–$C_6$, or taken together, $R^a$ and $R^b$ are lower alkylene, ie. $C_2$–$C_{12}$) in the presence of a metal catalyst with or without a base in an inert solvent to give isoquinoline compounds of formula (XIII). Metal catalysts include, but are not limited to, salts or phosphine complexes of Cu, Pd, or Ni (eg. $Cu(OAc)_2$, $PdCl_2(PPh_3)_2$, $NiCl_2(PPh_3)_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloaalkanes (preferably methylene chloride). Prefered reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao, et al. (*Tetrahedron*, 1994, 50, 979–988).

Compounds of formula (XIII) are converted into the target tetrahydroisoquinolines of formula via a two-step procedure employing first amine quaternization with a reagent $R^1$-LG, where LG represents a suitable leaving group such as I, Br, O-triflate, O-tosylate, O-methanesulfonate, etc. The reactions are optimally conducted in haloaalkanes (preferably methylene chloride), dialkyl ethers (preferably diethyl ether), cyclic ethers (preferably tetrahydrofuran or 1,4-dioxane) or other inert solvent. The reactions are optimally conducted at or below room temperature and reaction times vary from 10 minutes to 24 hours. The second step of the sequence involves reduction to the tetrahydroisoquinolines of formulae IA-F. Optimally, a mild reducing agent is employed, such as for example, sodium cyanoborohydride in the presence of acid catalyst to facilitate the reaction. Additional guidance for effectively conducting this chemistry may be located from the works of Miller, et al. (*Synthetic Communications*, 1994, 24, 1187–1193) and Terashima, et al. (*Heterocycles*, 1987, 26, 1603–1610).

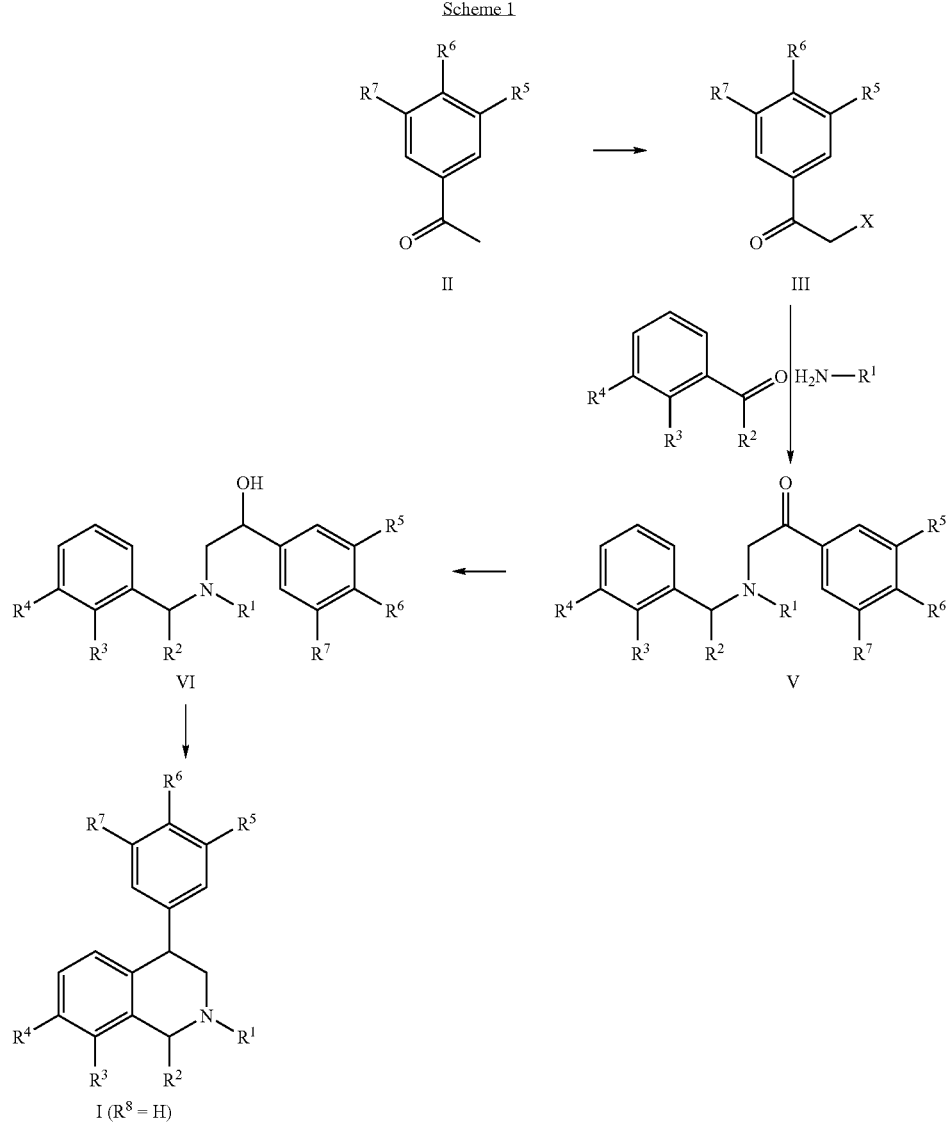
Scheme 1
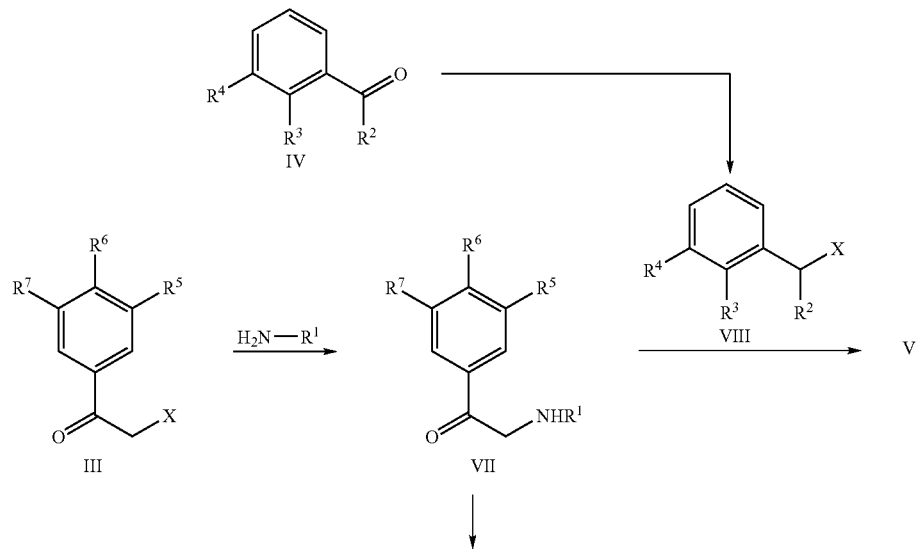
Scheme 2

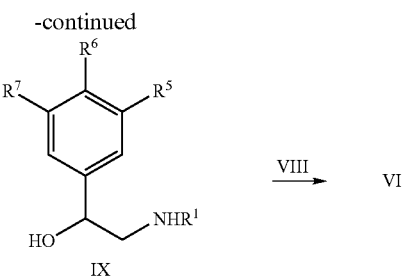
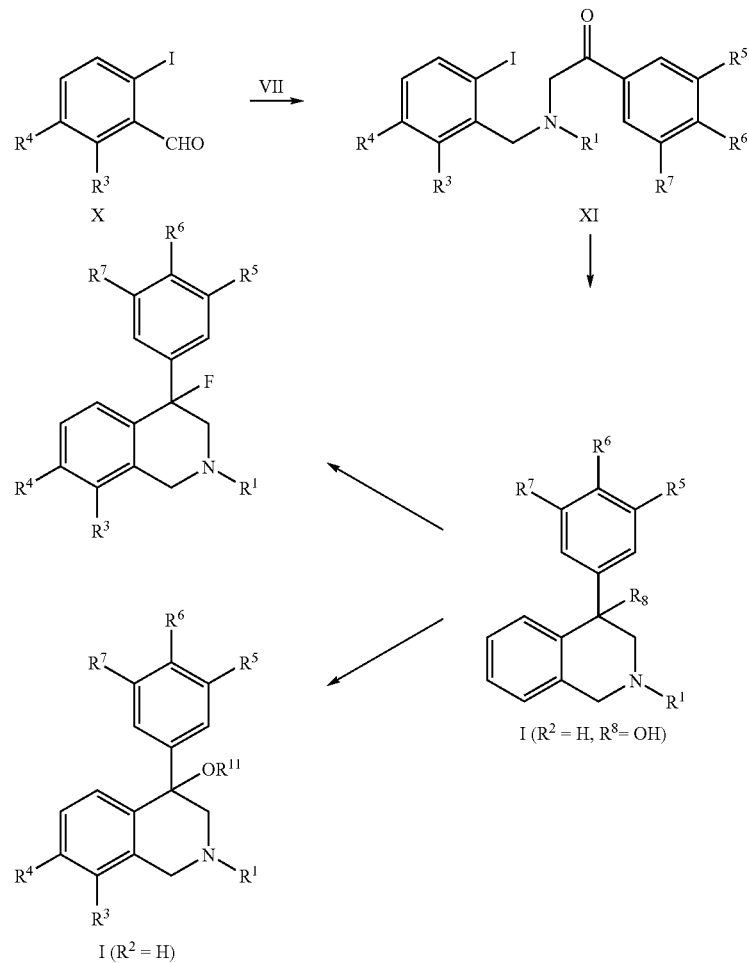
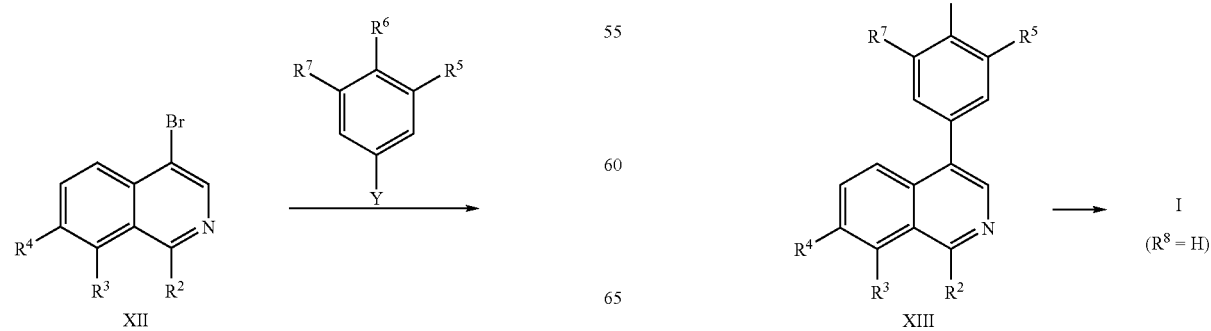

It will be appreciated that compounds useful according to the present invention may contain asymmetric centres. These asymmetric centres may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formulae (IA-F) hereinabove. Such isomers can be separated from their mixtures, by the application or adaptation of known methods, for example chromatographic techniques and recrystallisation techniques, or they are separately prepared from the appropriate isomers of their intermediates.

Radiolabelled compounds of the invention are synthesized by a number of means well known to those of ordinary skill in the art, e.g., by using starting materials incorporating therein one or more radioisotopes.

This invention provides compositions containing the compounds described herein, including, in particular, pharmaceutical compositions comprising therapeutically effective amounts of the compounds and pharmaceutically acceptable carriers.

It is a further object of the invention to provide kits having a plurality of active ingredients (with or without carrier) which, together, may be effectively utilized for carrying out the novel combination therapies of the invention.

It is another object of the invention to provide a novel pharmaceutical compositions which is effective, in and of itself, for utilization in a beneficial combination therapy because it includes a plurality of active ingredients which may be utilized in accordance with the invention.

The invention also provides kits or single packages combining two or more active ingredients useful in treating a disorder described herein. A kit may provide (alone or in combination with a pharmaceutically acceptable diluent or carrier), the compound of formulae (IA-F) and the additional active ingredient (alone or in combination with diluent or carrier) selected from a serotonin IA receptor antagonist, a selective neurokinin-1 receptor antagonist, and a norepinephrine precursor.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formulae (IA-F).

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine and serotonin uptake and are therefore believed to be useful in treating a disorder which is created by or is dependent upon decreased availability of serotonin, norepinephrine or dopamine. Although the compounds of the formulae (IA-F) inhibit synaptic norepinephrine, dopamine and serotonin uptake, in any individual compound these inhibitory effects may be manifested at the same or vastly different concentrations or doses. As a result, some compounds of the formulae (IA-F) are useful in treating such a disorder at doses at which synaptic norepinephrine uptake may be substantially inhibited but at which synaptic serotonin uptake or dopamine uptake is not substantially inhibited, or visa versa. Also, some compounds of the formulae (IA-F) are useful in treating such a disorder at doses at which synaptic dopamine uptake may be substantially inhibited but at which synaptic norepinephrine or serotonin uptake is not substantially inhibited, or visa versa. And, conversely, some compounds of the formulae (IA-F) are useful in treating such a disorder at doses at which synaptic serotonin uptake may be substantially inhibited but at which synaptic norepinephrine or dopamine uptake is not substantially inhibited, or visa versa. Other compounds of formulae (IA-F) are useful in treating such a disorder at doses at which synaptic norepinephrine, dopamine and serotonin uptake are substantially inhibited.

The concentrations or doses at which a test compound inhibits synaptic norepinephrine, dopamine and serotonin uptake is readily determined by the use of standard assay and techniques well known and appreciated by one of ordinary skill in the art. For example, the degree of inhibition at a particular dose in rats can be determined by the method of Dudley, et al., J. Pharmacol. Exp. Ther. 217, 834–840 (1981), which is incorporated by reference.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine and serotonin uptake. The therapeutically effective inhibitory dose can be readily determined by those skilled in the art by using conventional range finding techniques and analagous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds' having higher binding affinities, e.g. their ability to be selective, for the norepinephrine transporter protein ("NET") over the transporters for other neurochemicals, e.g., the dopamine transporter protein ("DAT") and the serotonin transporter protein ("SERT").

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radiolabelled ligands for the proteins. The binding of the radioligands to the proteins is reversible in the presence of other protein ligands, e.g., the compounds of this invention; said reversability, as described below, provides a means of measuring the compounds' binding affinities for the proteins (Ki). A higher Ki value for a compound is indicative that the compound has less binding affinity for a protein than is so for a compound with a lower Ki; conversely, lower Ki values are indicative of greater binding affinities.

Accordingly, the difference in compound selectivity for proteins is indicated by a lower Ki for the protein for which the compound is more selective, and a higher Ki for the protein for which the compound is less selective. Thus, the higher the ratio in Ki values of a compound for protein A over protein B, the greater is the compounds' selectivity for the latter over the former (the former having a higher Ki and the latter a lower Ki for that compound). Compounds provided herein induce fewer side effects during therapeutic usage because of their selectivity for the norepinephrine transporter protein, as indicated by the ratios of their Ki's for binding to NET over those for binding to other transporter proteins, e.g., DAT and SERT. Generally, some of the compounds of this invention have a Ki ratio for DAT/NET of at least about 2:1; generally also have a SERT/NET ratio of at least about 20:1.

Moreover, in vivo assessment of the activity of compounds at the NE and DA transporters is, for example, by determining their ability to prevent the sedative effects of tetrabenazine (TBZ) (see, e.g., G. Stille, Arzn. Forsch 14:534–537, 1964, the contents of which are incorporated herein by reference). Randomized and coded doses of test compounds are administered to mice, as is then a dose of tetrabenazine. Animals are then evaluated for antagonism of tetrabenazine-induced exploratory loss and ptosis at specified time intervals after drug administration. Exploratory activity is, for example, evaluated by placing the animal in the center of a circle and then evaluating the amount of time it takes for the animal to intersect the circle's perimeter—generally, the longer it takes for the animal to make this intersection, the greater is its loss of exploratory activity. Furthermore, an animal is considered to have ptosis if its eyelids are at least 50% closed. Greater than 95% of the control (vehicle-treated) mice are expected to exhibit exploratory loss and ptosis; compound-related activity is then calculated as the percentage of mice failing to respond to the tetrabenazine challenge dose, with therapeutically more effective compounds expected to better at reducing loss of exploratory behavior and ptosis.

Accordingly, this invention provides methods of treating subjects afflicted with various neurological and psychiatric disorders by administering to said subjects a dose of a pharmaceutical composition provided herein. Said disorders include, without limitation, attention deficit-hyperactivity disorder, anxiety, depression, post-traumatic stress disorder, supranuclear palsy, feeding disorders, obsessive compulsive disorder, analgesia, smoking cessation, panic attacks, Parkinson's and phobia. The compounds provided herein are particularly useful in the treatment of these and other disorders due, at least in part, to their ability to selectively bind to the transporter proteins for certain neurochemicals with a greater affinity than to the transporter proteins for other neurochemicals.

The compounds of the invention, their methods or preparation and their biological activity will appear more clearly from the examination of the following examples which are presented as an illustration only and are not to be considered as limiting the invention in its scope.

EXAMPLES

The compounds listed in the following Table I were made by the processes described above. Specific reaction and processing conditions for the preparation of 2,7-dimethyl-4-phenyl-1,2,3,4-tetrahydroisoquinoline (example 1), 2,7-dimethyl-4-(3-fluorophenyl)-1,2,3,4-tetrahydroisoquinoline (example 4), 2,7-dimethyl-4-(4-fluoro-3-methylphenyl)-1,2,3,4-tetrahydroisoquinoline (example 6), 2,7-dimethyl-8-fluoro-4-phenyl-1,2,3,4-tetrahydroisoquinoline (example 28), 4-(4-chloro-3-fluorophenyl)-2-methyl-1,2,3,4-tetrahydroisoquinoline (example 70), 4-(3,4-difluorophenyl)-2-methyl-1,2,3,4-tetrahydroisoquinoline (example 78) and 4-(3,5-difluorophenyl)-2-methyl-1,2,3,4-tetrahydroisoquinoline (example 80) are given following the table.

TABLE I

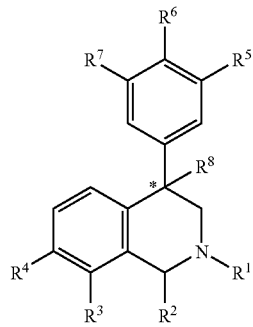

I

| Ex. | $R^1$ | $R^2$ | $R^3$ | $R^4$ | $R^5$ | $R^6$ | $R^7$ | $R^8$ | Mp (° C.) |
|---|---|---|---|---|---|---|---|---|---|
| 1 | Me | H | H | Me | H | H | H | H | 245–250[a] |
| 2 | Me | H | H | Me | H | OMe | H | H | 186–188[b] |
| 3 | Me | H | H | Me | H | F | H | H | 151–153[b] |
| 4 | Me | H | H | Me | F | H | H | H | Oil, MS[e] |
| 5 | Me | H | H | Me | F | F | H | H | 235–240[a] |
| 6 | Me | H | H | Me | Me | F | H | H | Oil, MS[e] |
| 7 | Me | H | H | Me | Cl | F | H | H | 243–253[a] |
| 8 | Me | H | H | Me | Cl | H | H | H | 226–230[c] |
| 9 | Me | H | H | Me | H | Me | H | H | 257–260[a] |
| 10 | Me | H | H | Me | F | Me | H | H | 230–231[a] |
| 11 | Me | H | H | Me | H | Cl | H | H | 208–210[b] |
| 12 | Me | H | H | Me | F | Cl | H | H | 240–249[a] |
| 13 | Me | H | H | Me | Cl | Cl | H | H | 245–246[a] |
| 14 | Me | H | H | Et | H | H | H | H | 160–162[d] |
| 15 | Me | H | H | Et | F | F | H | H | 140–141[d] |
| 16 | Me | H | H | F | H | OMe | H | H | 100–102[e] |
| 17 | Me | H | H | F | F | OMe | H | H | 225–230[a] |
| 18 | Me | H | H | F | F | Me | H | H | 240–241[f] |
| 19 | Me | H | H | F | F | Cl | H | H | 225–230[a] |
| 20 | Me | H | H | F | F | F | H | H | 232–235[f] |
| 21 | Me | H | H | F | Cl | H | H | H | 255–256[f] |
| 22 | Me | H | H | CN | H | H | H | H | Oil, MS[e] |
| 23 | Me | H | H | $CF_3$ | H | H | H | H | 257–275[a] |
| 24 | Me | Me | H | Me | H | H | H | H | 87–89[g] |
| 25 | Me | Me | H | H | H | Cl | H | H | Oil, MS[e] |
| 26 | Me | Me | H | H | F | F | H | H | Oil, MS[e] |
| 27 | Me | H | Me | Me | H | H | H | H | 108–113[h] |
| 28 | Me | H | F | Me | H | H | H | H | 215–216[a] |
| 29 | Me | H | Me | F | H | H | H | H | 185–186[i] |
| 30 | Me | H | OMe | Me | H | H | H | H | 130–131[j] |
| 31 | Me | H | OH | Me | H | H | H | H | 260–261[k] |
| 32 | Me | H | H | $OCF_3$ | H | H | H | H | 150–151[d] |
| 33 | Me | H | H | OMe | F | F | H | H | 94–95[e] |
| 34 | Me | H | H | OMe | Me | F | H | H | 215–217[l] |
| 35 | Me | H | H | OMe | F | Me | H | H | 165–166[d] |
| 36 | Me | H | H | OMe | Me | H | H | H | 173–177[d] |
| 37 | Me | H | H | O(Ph) | H | H | H | H | 175–176[d] |
| 38 | Me | H | H | O(4-OMePh) | H | H | H | H | 165–166[d] |
| 39 | Me | H | H | O($CH_2$Ph) | H | H | H | H | 155–156[m] |
| 40 | Me | H | H | OH | Me | H | H | H | 254–265[n] |
| 41 | Me | H | H | OH | F | Me | H | H | 186–187[b] |
| 42 | Me | H | H | OH | Me | F | H | H | 190–191[o] |

TABLE I-continued

I

| Ex. | R¹ | R² | R³ | R⁴ | R⁵ | R⁶ | R⁷ | R⁸ | Mp (° C.) |
|---|---|---|---|---|---|---|---|---|---|
| 43 | Me | H | H | OH | F | F | H | H | 236–237ⁿ |
| 44 | Me | H | H | H | CN | H | H | H | Oil, MSᵉ |
| 45 | Me | H | Me | H | H | H | H | H | Oil, MSᵉ |
| 46 | Me | H | Me | H | H | F | H | H | 165–166ᵇ |
| 47 | Me | H | Me | H | F | F | H | H | 125–127ᵃ |
| 48 | Me | H | Me | H | F | H | F | H | 250–252ᵍ |
| 49 | Me | H | Me | H | F | H | H | H | 125–127ᵒ |
| 50 | Me | H | Me | H | Me | F | H | H | Oil, MSᵉ |
| 51 | Me | H | Me | H | Cl | F | H | H | 243–260ᵃ |
| 52 | Me | H | Me | H | Cl | Cl | H | H | 246–248ᵃ |
| 53 | Me | H | Me | H | Cl | H | H | H | 228–230ᵃ |
| 54 | Me | H | Me | H | H | Cl | H | H | 200–202ᵖ |
| 55 | Me | H | Me | H | F | Cl | H | H | 218–228ᵃ |
| 56 | Me | H | Me | H | H | OMe | H | H | 79–81ᶜ |
| 57 | Me | H | Me | H | H | CN | H | H | Oil, MSᵉ |
| 58 | Me | H | Me | H | H | CF₃ | H | H | 214–216ᵒ |
| 59 | Me | H | Me | H | H | Me | H | H | Oil, MSᵉ |
| 60 | Me | H | CH₂NHMe | H | H | H | H | H | 278–282ᵃ |
| 61 | Me | H | CH₂OH | H | H | H | H | H | 144–146ᑫ |
| 62 | Me | H | SO₂NH₂ | H | H | H | H | H | 231–242ʳ |
| 63 | Me | H | SO₂NHMe | H | H | H | H | H | 258–265ᵃ |
| 64 | Me | H | OMe | H | H | Me | H | H | 225–260ᶠ |
| 65 | Me | H | OMe | H | F | H | F | H | 165–166ᵇ |
| 66 | Me | H | OMe | H | Cl | H | H | H | 147–148ᵇ |
| 67 | Me | H | OMe | H | Cl | Cl | H | H | 230–235ᵖ |
| 68 | Me | H | OMe | H | F | Cl | H | H | 179–183ˢ |
| 69 | Me | H | OMe | H | Cl | F | H | H | 245–252ᵃ |
| 70 | Me | H | H | H | F | H | F | H | 230–233ᵍ |
| 71 | Me | H | H | H | F | H | Cl | H | 205–207ᵃ |
| 72 | Me | H | H | Me | F | H | F | H | 230–231ᵃ |
| 73 | Me | H | H | Me | F | H | Cl | H | 180–200ᵃ |
| 74 | Me | H | H | H | F | F | F | H | 227–230ᶠ |
| 75 | Me | H | H | H | F | H | H | H | 218–220ᵃ |
| 76 | Me | H | H | H | F | Me | H | H | 215–217ᵖ |
| 77 | Me | H | H | H | Me | F | H | H | 193–195ᵇ |
| 78 | Me | H | H | H | F | F | H | H | 200(Sub.)ᶠ |
| 79 | Me | H | H | H | Cl | H | H | H | 218–220ᵃ |
| 80 | Me | H | H | H | F | Cl | H | H | 230–235ᵃ |
| 81 | Me | H | H | H | Cl | F | H | H | Oil, MSᵉ |
| 82 | Me | H | H | H | CN | H | H | H | Oil, MSᵉ |
| 83 | Me | H | H | H | H | NHCOMe | H | H | 183–189ᑫ |
| 84 | Me | H | H | H | H | Cl | H | F | 205–210ᵃ |
| 85 | Me | Me | H | Me | F | H | F | H | 194–197ᶠ |
| 86 | Me | H | H | Me | F | F | F | H | 269–274ᵃ |
| 87 | Et | H | H | Me | H | F | H | H | Oil-Msᵉ |
| 88 | Me | H | H | Me | H | F | H | OH | Oil-Msᵉ |
| 89 | Me | H | F | CH₂Me | H | H | H | H | 185–205ˢ |
| 90 | Me | H | H | CH₂NH₂ | H | H | H | H | 176–177ᵘ |
| 91 | Me | H | H | CH₂NHMe | H | H | H | H | 160–163ᵘ |
| 92 | Me | H | OH | CN | H | H | H | H | 234–238ᵉ |

TABLE I-continued

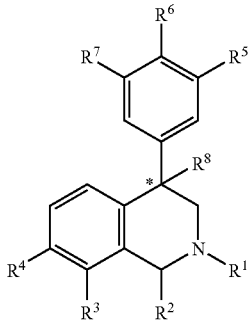

| Ex. | R[1] | R[2] | R[3] | R[4] | R[5] | R[6] | R[7] | R[8] | Mp (° C.) |
|---|---|---|---|---|---|---|---|---|---|
| 93 | Me | H | H | CH$_2$OH | H | H | H | H | 237–240[l] |
| 94 | Et | H | H | H | H | H | H | H | 172–174[b] |

Footnotes for Table I for Salt Forms of the examples:
[a]Mono Hydrochloride
[b]Mono Maleate
[c]Mono Hydrochloride.0.2 Hydrate
[d]Mono Fumarate
[e]Free Base - mass spectrum shows molecular ion
[f]Mono Hydrochloride.0.25 Hydrate
[g]Mono Hydrochloride.0.10 Hydrate
[h]Mono Hydrochloride.0.75 Hydrate
[i]1.5 Fumarate.0.25 Hydrate
[j]Mono Fumarate.0.5 Diethyl ether
[k]Mono Hydrobromide.0.25 Hydrate
[l]Mono Hydrochloride.0.33 Hydrate
[m]Mono Fumarate.0.25 Hydrate
[n]Mono Hydrobromide
[o]Mono Maleate.0.25 Hydrate
[p]Mono Hydrochloride.0.5 Hydrate
[q]0.25 Hydrate
[r]Mono Maleate.0.25 Hydrate.0.13 Ethanol
[s]Mono Sulfate
[t]Di Hydrochloride.0.5 Hydrate
[u]Bis Maleate Example 1

Preparation of 2,7-dimethyl-4-phenyl-1,2,3,4-tetrahydroisoquinoline

Step A: A solution of m tolualdehyde (500 mg; 4.16-mmol), □-(methylaminomethyl)benzyl alcohol (630 mg, 4.16 mmol) and acetic acid (0.5 ml) was stirred in methanol (16 ml) at 0° C. under nitrogen as sodium cyanoborohydride (784 mg, 12.5 mmol) was added in small portions. The reaction mixture was stirred for 5 minutes at 0° C. and two days at ambient temperature. The reaction mixture was brought to pH 12 with 2N sodium hydroxide, diluted with water, and extracted with diethyl ether (3×). The combined organic extracts were washed with brine, dried over anhydrous magnesium sulfate, and the solvent removed in vacuo to provide the desired intermediate (1.24 g): $^1$H NMR (300 MHz, CDCl$_3$) δ 7.08–7.35 (m, 9H), 4.73–4.77 (m, 1H), 3.71 (d, J=13.0 Hz, 1H), 3.50 (d, J=13.0 Hz, 1H), 2.46–2.67 (m, 2H), 2.36 (s, 3H), 2.32 (s, 3H); CI MS m/z=256 [C$_{17}$H$_{21}$NO+H]$^+$.

Step B: The product from Step A (1.24 g, 4.90 mmol) was stirred in methylene chloride (208 ml) and treated dropwise with concentrated sulfuric acid (98%, 10 ml) over 3 minutes. After stirring for 20 minutes, the reaction was diluted with ice chips and made basic with 25% aqueous ammonium hydroxide. The reaction mixture was extracted with methylene chloride (3×) and the organic extracts combined, dried over anhydrous sodium sulfate, filtered, and concentrated in vacuo. Purification by column chromatography, eluting with hexanes/ethyl acetate (5/1), afforded the desired tetrahydroisoquinoline (0.23 g): $^1$H NMR (300 MHz, CDCl$_3$) δ 7.17–7.31 (m, 5H), 6.87–6.89 (m, 2H), 6.75 (d, J=7.8 Hz, 1H), 4.20–4.26 (m, 1H), 3.72 (d, J=14.8 Hz, 1H), 3.57 (d, J=14.8 Hz, 1H), 2.96–3.10 (m, 1H), 2.51–2.58 (m, 1H), 2.42 (s, 3H), 2.29 (s, 3H).

Step C: The product from Step B (0.23 g) was treated with ethereal HCl in methanol (5 ml) to afford a precipitate. The solvents and excess HCl were removed in vacuo and the resultant solid recrystallized from ethanol/diethyl ether to provide the HCl salt of the target (0.21 g) as a white solid: mp 245–250° C.; $^1$H NMR (CD$_3$OD) δ 6.86–7.40 (m, 7H), 6.74 (d, J=7.8 Hz, 1H), 4.52–4.64 (m, 3H), 3.72–3.88 (m, 1H), 3.45–3.55 (m, 1H), 3.08 (s, 3H), 2.32 (s, 3H); $^{13}$C NMR (75 MHz, CD$_3$OD) □130.6, 130.3, 129.1, 127.8, 59.3, 56.8, 44.5, 44.0, 21.1; IR (Kbr) 2937, 2474, 1454, 701 cm$^{-1}$; CI MS m/z=238 [C$_{17}$H$_{19}$N+H]$^+$. Anal. Calcd. for C$_{17}$H$_{19}$N—HCl: C, 74,57; H, 7.36; N, 5.12. Found: C, 74.20; H, 7.34; N, 4.82.

Example 4

Preparation of 2,7-dimethyl-4-(3-fluorophenyl)-1,2,3,4-tetrahydroisoquinoline Step A: m-Tolualdehyde (1.66 g, 14.0 mmol) was treated with methyl amine (40% aqueous, 1.39 ml, 18.0 mmol) in methanol (20 ml) at room temperature. The reaction was stirred 20 minutes and treated with sodium borohydride (0.26 g, 7.0 mmol) portionwise. The reaction was stirred 1 hour and treated with 3'-fluoro-2-bromoacetophenone (3.0 g, 14.0 mmol) followed by stirring for 45 minutes at room temperature. The reaction was finally treated with sodium borohydride (0.52 g, 14.0 mmol) portionwise and stirring continued overnight. The reaction was diluted with water (100 ml) and extracted with methylene chloride (3×100 ml). The combined organic extracts were washed with brine and dried over anhydrous sodium sulfate, followed by filtration and concentration in vacuo. Purification by column chromatography on silica gel eluting with hexanes/ethyl acetate (3/1) provided the amino alcohol (4.3 g) as a yellow oil; 1 H NMR (300 MHz, CDCl$_3$) δ 7.08–7.30 (m, 7H), 4.73 (t, J=6.0 Hz, 1H), 3.60 (ABq, JAB=14.0 Hz, 2H), 2.55 (d, J=8.0 Hz, 2H), 2.36 (s, 3H), 2.31 (s, 3H); CI MS m/z=274 [C$_{17}$H$_{20}$NFO+H]$^+$.

Step B: The product from Step A (1.0 g, 4.0 mmol) was stirred in methylene chloride (100 ml) and treated dropwise with concentrated sulfuric acid (98%, 7.0 ml) over 3 minutes. After stirring for 1 hour, the reaction was diluted with ice chips and and made basic with 25% aqueous ammonium hydroxide. The reactions mixture was extracted with methylene chloride (3×100 ml) and the organic extracts combined, dried over anhydrous sodium sulfate, filtered, and concentrated in vacuo. Purification by column chromatography, eluting with hexanes/ethyl acetate (3/1), afforded the desired tetrahydroisoquinoline as a yellow oil: $^1$H NMR (300 MHz, CDCl$_3$) δ 6.89–7.00 (m, 5H), 6.75 (d, J=8.0 Hz,1H), 4.21 (t, J=7.0 Hz, 1H), 3.64 (AB$_q$, J$_{AB}$=15.0 Hz, 2H), 3.02 (m, 1H), 2.56 (m, 1H), 2.41 (s, 3H), 2.29 (s, 3H); CI MS m/z=256 [C$_{17}$H$_{18}$NF+H]$^+$.

Step C: The product from Step B was subjected to chiral HPLC separation employing a Chiral Technologies Chiracel® AD column (5 cm×50 cm) eluting with hexanes/isopropanol (9/1) to afford the (R), [a]$_D^{25}$−16.3 (c=0.498, MEOH) and (S), [α]$_D^{25}$+16.3 (c=0.476, MEOH) enantiomers in order of elution. The (S)-(+) enantiomer was treated with maleic acid (1.0 equilvalent) and the resultant maleate salt filtered and dried to constant weight. (S)-(+)-2,7-dimethyl-4-(3-fluorophenyl)-1,2,3,4-tetrahydroisoquinoline, maleate salt: mp 172–173.5° C.

Example 6

Preparation of 2,7-dimethyl-4-(4-fluoro-3-methylphenyl)-1,2,3,4-tetrahydroisoquinoline Step A: m-Tolualdehyde (4.0 g, 33.0 mmol) was treated with methyl amine (40% aqueous, 3.36 ml, 43.0 mmol) in methanol (40 ml) at room temperature. The reaction was stirred 20 minutes and treated with sodium borohydride (0.64 g, 33.0 mmol) portionwise. The reaction was stirred 1 hour and treated with 4'-fluoro-3'-methyl-2-bromoacetophenone (7.69 g, 33.0 mmol) followed by stirring for 45 minutes at room temperature. The reaction was finally treated with sodium borohydride (1.0 g, 33 mmol) portionwise and stirring continued overnight. The reaction was diluted with water (100 ml) and extracted with methylene chloride (3×100 ml). The combined organic extracts were washed with brine and dried over anhydrous sodium sulfate, followed by filtration and concentration in vacuo. Purification by column chromatography on silica gel eluting with hexanes/ethyl acetate (2/1) provided the amino alcohol (65.3 g) as a yellow oil; CI MS m/z=286[C$_{18}$H$_{22}$NFO+H]$^+$.

Step B: The product from Step A (0.52 g, 2.0 mmol) was dissolved in methylene chloride (20 ml) and treated dropwise with concentrated sulfuric acid (98%, 3 ml). The reaction was stirred overnight at room temperature, then diluted with ice chips and and made basic with 25% aqueous ammonium hydroxide. The reaction mixture was extracted with methylene chloride (3×50 ml) and the organic extracts combined, dried over anhydrous sodium sulfate, filtered, and concentrated in vacuo. Purification by column chromatography, eluting with hexanes/ethyl acetate (3/1) afforded the desired tetrahydroisoquinoline (0.08 g): $^1$H NMR (300 MHz, CDCl$_3$) δ 6.87–7.00 (m, 5H), 6.74 (d, J=8.0 Hz, 1H), 4.17 (t, J=7.0 Hz, 1H), 3.64 (AB$_q$, J$_{AB}$=15.0 Hz, 2H), 3.01 (m, 1H), 2.53 (m, 1H), 2.40 (s, 3H), 2.29 (s, 3H), 2.23 (s, 3H); CI MS m/z=270 [C$_{18}$H$_{20}$NF+H]$^+$.

Example 28

Preparation of 2,7-dimethyl-8-fluoro-4-phenyl-1,2,3,4-tetrahydroisoquinoline Step A: A solution of □-(methylaminomethyl)benzyl alcohol (745 mg, 4.9 mmol) and triethylamine (0.79 ml, 5.66 mmol) in acetonitrile (45 ml) at 0° C. under nitrogen was treated dropwise with 2-fluoro-3-methylbenzyl bromide (1.0 g, 4.9 mmol) as a solution in acetonitrile (25 ml). The reaction was stirred at 0° C. for 1 hour and at room temperature for 1.5 hours, followed by dilution with water and extraction with methylene chloride (3×). The combined organic extracts were dried over anhydrous magnesium sulfate, filtered, and concentrated in vacuo to provide the alkylation product (1.35 g); $^1$H NMR (CDCl$_3$) δ 7.23 (m, 5H), 7.08–7.17 (m, 2H), 6.97–7.06 (m, 1H), 4.71–4.82 (m, 1H), 3.79 (d, J=13.1 Hz, 1H), 3.62 (d, J=13.2 Hz, 1H), 2.33 (s, 3H), 2.29 (s, 3H).

Step B: The product from Step A (0.5 g, 1.8 mmol) was treated with sulfuric acid (3.7 ml) and purified by column chromatography as described for Example 1, Step B to afford the desired product (0.33 g) as an oil: $^1$H NMR (CDCl$_3$) δ 7.06–7.37 (m, 5H), 6.88 (t, J=7.8 Hz, 1H), 6.54 (d, J=7.8 Hz, 1H), 4.18–4.27 (m, 1H), 3.86 (d, J=15.6 Hz, 1H), 2.94–3.04 (m, 1H), 2.49–2.59 (m, 1H), 2.45 (s, 3H), 2.22 (s, 3H).

Step C: The product from Step B (0.33 g, 1.3 mmol) was treated with ethereal HCl as described in Example 1, Step C to provide the anticipated hydrochloride salt (0.30 g): mp 215–216° C.; $^1$H NMR (300 MHz, CD$_3$OD) δ 7.31–7.44 (m, 2H), 7.21–7.28 (m, 2H), 7.15 (t, J=7.9 Hz, 1H), 6.61 (d, J=8.0 Hz, 1H), 4.67–4.78 (m, 1H), 4.42–4.62 (m, 2H), 3.77–3.88 (m, 1H), 3.55 (t, J=12.0 Hz, 1H), 3.11 (s, 3H), 2.26 (s, 3H); IR (KBr) 3432, 2954, 2376, 1497, 1457, 1216, 1043, 704 cm$^{-1}$; CI MS m/z=256 [C$_{17}$H$_{18}$NF+H]$^+$. Anal. Calcd.for C$_{17}$H$_{18}$NF—HCl: C, 69.98; H, 6.56; N, 4.80. Found: C, 69.64; H, 6.49; N, 4.65.

Example 70

Preparation of 4-(4-chloro-3-fluorophenyl)-2-methyl-1,2,3,4-tetrahydroisoquinoline

Step A: Methylmagnesium bromide was added dropwise over 5 minutes to a stirred solution of 4-chloro-3-fluorobenzaldehyde (10.86 g, 68.5 mmol) in anhydrous tetrahydrofuran (100 ml) at −78° C. under nitrogen. After stirring for 15 minutes, the cooling bath was removed, and the solution allowed to warm to room temperature. After stirring 3 hours, the solution was poured slowly with stirring into saturated ammonium chloride (100 ml), then diluted with water (50 ml) and extracted with diethyl ether. The organic extracts were washed with water and saturated sodium chloride, dried over anhydrous sodium sulfate, filtered and the solvent removed in vacuo to provide the benzylic alcohol (11.89 g) as a clear, yellow oil: $^1$H NMR (300 MHz, CDCl$_3$) δ 7.35 (t, J=7.8 Hz, 1H), 7.18 (dd, J=2.0, 10.0 Hz, 1H), 7.07 (dd, J=10.7, 8.1 Hz, 1H), 4.83–4.92 (m, 1H), 2.01 (d, J=3.6 Hz, 1H), 1.47 (d, J=6.3 Hz, 3H), CI MS m/z=175 [C$_8$H$_8$ClFO+H]$^+$.

Step B: The product from Step A (9.0 g, 52.0 mmol) in anhydrous methylene chloride (60 ml) under nitrogen was added by cannula to a stirred suspension of pyridinium chlorochromate (16.7 g, 77.0 mmol) and diatomaceous earth (15 g) in anhydrous methylene chloride (150 ml) at 0° C. under nitrogen. After stirring for 26 hours, the heterogeneous mixture was diluted with diethyl ether (300 ml), stirred for 1 hour, and filtered. The filtrate was concentrated in vacuo and the volatile product purified by column chromatography on silica gel (60 g) eluting with hexanes/ethyl acetate (9/1) to provide the desired acetophenone in quantitative crude yield: $^1$H NMR (300 MHz, CDCl$_3$) δ 7.65–7.75 (m, 2H), 7.51 (t, J=7.6 Hz, 1H), 2.60 (s, 3H), CI MS m/z=173 [C$_8$H$_6$ClFO+H]$^+$.

Step C: The product from Step B (52 mmol) was treated with tetrabutylammonium tribromide (25.5 g, 52.9 mmol) in methanol/methylene chloride (1/3, 240 ml) under nitrogen. After stirring 3 days at room temperature, the solvents were removed in vacuo, and the residue dissolved in diethyl ether (200 ml), washed with water (4×50 ml), dried over anhydrous sodium sulfate, filtered and concentrated in vacuo. Purification by column chromatography on silica gel (120 g) eluting with hexanes/ethyl acetate (30/1) afforded the desired □-bromoacetophenone (6.23 g) as a crystalline solid: $^1$H NMR (300 MHz, CDCl$_3$) δ 7.70–7.81 (m, 2H), 7.55 (t, J=7.7 Hz, 1H), 4.39 (s, 2H); CI MS m/z=251 [C$_8$H$_5$BrClFO+H]$^+$.

Step D: Methylamine (40 wt % aqueous, 18.0 mmol) was added to a stirred solution of benzaldehyde (1.8 g, 17 mmol) in methanol (20 ml) under nitrogen. After stirring 10 minutes at room temperature, the solution was cooled to 0° C. and treated with sodium borohydride (0.32 g, 8.5 mmol) portionwise. The reaction was stirred for 15 minutes, warmed to room temperature and stirred an additional 1 hour, whereupon the product from Step C (4.3 g, 17 mmol) was added. The reaction was stirred 1 hour, cooled to 0° C. again with sodium borohydride (0.32 g, 8.5 mol) and allowed to stir overnight with warming to room temperature. The solution was diluted with water (100 ml) and extracted with methylene chloride (3×50 ml). The organic extracts were dried over anhydrous sodium sulfate, filtered, and concentrated in vacuo to provide the desired product as a clear yellow oil (1.77 g): $^1$H NMR (300 MHz, CDCl$_3$) δ 7.25–7.39 (m, 6H), 7.17 (dd, J=11.8, 10.0 Hz, 1H), 7.04 (d, J=8.3 Hz, 1H), 4.69 (dd, J=5.8, 8.2 Hz, 1H), 3.74 (d, J=13.0 Hz, 1H), 3.52 (d, J=13.0 Hz, 1H), 2.45–2.57 (m, 2H), 2.32 (s, 3H), CI MS m/z=294 [C$_{16}$H$_{17}$ClFNO+H]$^+$.

Step E: The product from Step D (1.77 g, 6.0 mmol) was stirred in concentrated sulfuric acid (4.0 ml) and methylene chloride (40 ml) for 15 minutes at room temperature. The reaction was poured on ice, made alkaline with concentrated ammonium hydroxide, and extracted with diethyl ether. The combined ether extracts were dried over sodium sulfate, filtered and concentrated in vacuo to afford the crude product as a cloudy yellow oil (1.7 g): $^1$H NMR (300 MHz, CDCl$_3$) δ7.30 (t, J=7.9 Hz, 1H), 7.06–7.22 (m, 3H), 6.92–7.03 (m, 2H), 6.85 (d, J=7.4 Hz, 1H), 4.28 (t, J=6.7 Hz, 1H), 3.77 (d, J=15.1 Hz, 1H), 3.70 (d, J=15.1 Hz, 1H), 3.05 (dd, J=5.6, 11.9 Hz, 1H), 2.62 (dd, J=8.0, 11.5 Hz, 1H), 2.46 (s, 3H).

Step F: The product from Step E (1.7 g, 6.0 mmol) was treated with ethereal HCl (1.0 M, 12.0 ml, 12.0 mmol) in methanol (20 ml) to afford a precipitate. The solvents and excess HCl were removed in vacuo and the resultant solid recrystallized from methanol/diethyl ether to provide the HCl salt of the target (1.1 g) as a white solid: mp 230–235° C.; $^1$H NMR (CD$_3$OD) δ 7.51 (t, J=8.0 Hz, 1H), 7.26–7.39 (m, 3H), 7.18 (dd, J=2.0, 10.2 Hz, 1H), 7.11 (dd, J=11.8, 8.3 Hz, 1H), 6.92 (d, J=7.9 Hz, 1H), 4.68 (dd, J=6.3, 11.3 Hz, 1H), 4.59 (bs, 2H), 3.87 (dd, J=6.2, 12.4 Hz, 1H), 3.56 (t, J=11.8 Hz, 1H), 3.08 (s, 3H); IR (Kbr) 3448, 2928, 2365, 1491, 1060, 747 cm$^{-1}$; CI MS m/z=276 [C$_{16}$H$_{15}$NCIF+H]$^+$; Anal. Calcd. for C$_{16}$H$_{15}$NCIF·HCl: C, 61.55; H, 5.17; N, 4.49. Found: C, 61.20; H, 5.07; N, 4.32.

Step G: The product from Step E was subjected to chiral HPLC separation employing a Chiral Technologies Chiracel® OD column (2 cm×20 cm) eluting with hexanes/isopropanol (9/1) to afford the (S) and (R) enantiomers in order of elution. Each enantiomer was treated with maleic acid (1.0 equivlalent) and the resultant maleate salts filtered and dried to constant weight. (S)-(+)-4-(4-chloro-3-fluorophenyl)-2-methyl-1,2,3,4-tetrahydroisoquinoline, maleate salt: mp 171–172° C.; $[\alpha]_D^{25}$+16.0 (c=0.200, MeOH)-(R)-(−)-4-(4-chloro-3-fluorophenyl)-2-methyl-1;2,3,4-tetrahydroisoquinoline, maleate salt: mp 171–172° C.; $[\alpha]_D^{25}$−15.5 (c=0.200, MeOH).

Example 78

Preparation of 4-(3,4-difluorophenyl)-2-methyl-1,2,3,4-tetrahydroisoquinoline

Step A: 3,4-Difluoroacetophenone (25.0 g, 160.0 mmol) was treated with acetic acid (250 ml) and bromine (8.23 ml, 160.0 mmol, solution in 13 ml acetic acid) at room temperature under nitrogen. The reaction was stirred at room temperature for 1 hour and concentrated in vacuo to remove acetic acid. The residue was suspended in saturated sodium carbonate and extracted with methylene chloride several times. The combined organic extracts were dried over anhydrous sodium sulfate, filtered and concentrated in vacuo to afford the desired bromoacetophenone derivative (37.0 g) as a yellow crystalline solid: $^1$H NMR (300 MHz, CDCl$_3$) δ 7.81 (m, 2H), 7.32 (m, 1H), 4.39 (s, 2H).

Step B: The product from Step A (37.0 g, 158.0 mmol) was dissolved in methylene chloride (290 ml) and added dropwise to a solution of N-benzyl-N-methylamine (20.3 ml, 158.0 mmol) and triethylamine (22.0 ml, 158.0 mmol) in methylene chloride (312 ml). The addition was carried out over 45 minutes at 0° C., warmed to room temperature and allowed to stir an additional 4 hours. The reaction was diluted with water (300 ml) and extracted with methylene chloride. The combined organic extracts were dried over anhydrous sodium sulfate, filtered, and concentrated in vacuo. The product was purifed by column chromatography on silica gel (600 g) eluting with hexanes/ethyl acetate (7/3) to afford the desired alkylation product as a clear, light brown oil (30.2 g): $^1$H NMR (300 MHz, CDCl$_3$) δ 7.87–7.73 (m, 2H), 7.35–7.15 (m, 6H), 3.68 (s, 2H), 3.64 (s, 2H), 2.34 (s, 3H).

Step C: The product from Step B (15.0 g, 54.0 mmol) was dissolved in methanol (65 ml), chilled in an ice bath and treated with sodium borohydride (1.38 g, 36.0 mmol). The reaction was stirred at 0° C. for 1 hour and at room temperature for 1 hour, followed by quenching with water and extraction with methylene chloride. The combined organic extracts were dried over sodium sulfate, filtered and concentrated in vacuo to directly provide the pure benzylic alcohol (14.4 g) as a yellow oil: $^1$H NMR (300 MHz, CDCl$_3$) δ 7.38–7.00 (m, 8H), 4.67 (t, J=7.0 Hz, 1H), 3.74 and 3.35 (AB$_q$, J$_{AB}$=13.2 Hz, 2H), 2.50 (d, J=7.0 Hz, 2H), 2.31 (s, 3H). Anal. Calcd. for C$_{16}$H$_{17}$N$_1$O$_1$F$_2$: C, 69.30; H, 6.19; N, 5.05. Found: C, 68.94; H, 6.21; N, 4.94.

Step D: The product from Step C (14.4 g, 52.0 mmol) was stirred in concentrated sulfuric acid (27.0 ml) and methylene chloride (333 ml) for 15 minutes at room temperature. The reaction was poured on ice, made alkaline with concentrated ammonium hydroxide, and extracted with diethyl ether. The combined ether extracts were dried over sodium sulfate, filtered, and concentrated in vacuo. The product was purified by column chromatography on silica gel eluting with hexanes i ethyl acetate (1/1) to provide the pure tetrahydroisoquinoline (11.4 g): $^1$H NMR (300 MHz, CDCl$_3$) δ 7.29–7.36 (m, 1H), 6.83–7.20 (m, 6H), 4.20 (t, J=6.3 Hz, 1H), 3.66 (s, 2H), 2.95 (dd, J=5.4, 11.5 Hz, 1H), 2.58 (dd, J=7.4, 11.3 Hz, 1H), 2.41 (s, 3H).

Step E: The product from Step D (0.8 g, 3.0 mmol) was treated with ethereal HCl as described in Example 1, Step F to provide the anticipated hydrochloride salt (0.6 g): mp 200° C. (sublimed); $^1$H NMR (300 MHz, CD$_3$OD) δ 7.24–7.39 (m, 4H), 7.14–7.23 (m, 1H), 7.06–7.13 (m, 1H), 6.92 (d, J=7.8 Hz, 1H), 4.65 (dd, J=6.1, 11.4 Hz), 4.58 (s, 2H), 3.85 (dd, J=6.2, 12.4 Hz, 1H), 3.54 (t, J=11.8 Hz, 1H), 3.07 (s, 3H); IR (KBr) 3448, 2932, 2549, 1512, 1465, 1276, 742 cm$^{-1}$; CI MS m/z=260 [C$_{16}$H$_{15}$NF$_2$+H]+. Anal. Calcd. for C$_{16}$H$_{15}$NF$_2$—HCl-0.25H$_2$O: C, 64.00, H, 5.54; N, 4.66. Found: C, 64.11; H, 5.30; N, 4.62.

Step F: The product from Step D was subjected to chiral HPLC separation employing a Chiral Technologies Chiracel® OD column (2 cm×20 cm) eluting with hexanes/ isopropanol (9/1) to afford the (S) and (R) enantiomers in order of elution. Each enantiomer was treated with maleic acid (1.0 equilvalent) and the resultant maleate salts filtered and dried to constant weight. (S)-(−)-4-(3,4-difluorophenyl)-2-methyl-1,2,3,4-tetrahydroisoquinoline, maleate salt: mp 138–139° C.; [α]$_D^{25}$−2.6 (c=0.366, MeOH). (R)-(+)-4-(3,4-difluorophenyl)-2-methyl-1,2,3,4-tetrahydroisoquinoline, maleate salt: 138–139° C.; [α]$_D^{25}$ +2.5 (c=0.386, MeOH).

Example 80

Preparation of 4-(3.5-difluorophenyl)-2-methyl-1,2,3,4-tetrahydroisoquinoline

Step A: Tetrabutylammonium tribromide (18.6 g, 38.6 mmol) was added to a stirred solution of 3,5-difluoroacetophenone (6.0 g, 38.6 mmol) in methanol/methylene chloride (1/3, 180 ml) under nitrogen. After stirring at room temperature for 72 hours, the solvents were removed in vacuo. The residue was dissolved in diethyl ether (200 ml), washed with water (4×50 ml), dried over anhydrous sodium sulfate, filtered and the solvent removed in vacuo to give a mixture of the α-bromoacetophenone and the corresponding dimethyl ketal (9.0 g): $^1$H NMR (300 MHz, CDCl$_3$) δ 7.50 (dd, J=2.0, 4.0 Hz, 2H), 7.08 (m, 1H), 4.39 (s, 2H).

Step B: To the product mixture from Step A (3.5 g, 14.7 mmol) and N-methyl-N-benzylamine (1.8 g, 14.7 mmol) in methylene chloride (15 ml) was added diisopropyl ethyl amine (3.0 ml, 17 mmol). The reaction was stirred at room temperature for 5.5 hours, then washed with water and dried over anhydrous sodium sulfate. After filtration and concentration in vacuo, the material was purified by column chromatography on silica gel (140 g) eluting with hexanes/ethyl acetate/triethylamine (9/1/0.1) to provide the desired alkylation product (1.2 g) as an orange oil: $^1$H NMR (300 MHz, CDCl$_3$) δ 7.48 (dd, J=2.0, 4.0 Hz, 2H), 7.33 (m, 5H), 7.00 (m, 1H), 3.69 (s, 2H), 3.66 (s, 2H), 2.36 (s, 3H).

Step C: The product from Step B (1.1 g, 4.0 mmol) was dissolved in methanol, chilled in an ice bath and treated with sodium borohydride (0.1 g, 2.7 mmol). The reaction was stirred at 0° C. for 1 hour and at room temperature for 1 hour, followed by quenching with water and extraction with methylene chloride. The combined organic extracts were dried over sodium sulfate, filtered and concentrated in vacuo to provide the benzylic alcohol (0.8 g) as an orange oil: $^1$H NMR (300 MHz, CDCl$_3$) δ 7.40–7.30 (m, 5H), 6.90–6.82 (m, 1H), 6.70–6.60 (m, 1H), 4.70 (m, 1H), 3.73 (d, J=14.0 Hz, 1H), 3.52 (d, J=14.0 Hz, 1H), 2.55–2.40 (m, 2H), 2.29 (s, 3H).

Step D: The product from Step C (0.4 g, 1.4 mmol) was stirred in concentrated sulfuric acid (1.5 ml) and methylene chloride (10 ml) for 15 minutes at room temperature. The reaction was poured on ice, made alkaline with concentrated ammonium hydroxide, and extracted with diethyl ether. The combined ether extracts were dried over sodium sulfate, filtered and concentrated in vacuo. Purification by column chromatography on silica gel (15 g) eluting with hexanes/ ethyl acetate/triethylamine (9/1/0.1) afforded the target (70 mg): $^1$H NMR (300 MHz, CDCl$_3$) δ 7.40–7.07 (m, 4H), 6.87 (d, J=7.0 Hz, 1H), 6.77–6.62 (m, 2H), 4.21 (t, J=6.0 Hz, 1H), 3.66 (d, J=2.0 Hz, 2H), 2.95 (dd, J=5.0, 6.0 Hz, 1H), 2.61 (dd, J=6.0 Hz, 7.0 Hz, 1H), 2.41 (s, 3H).

Step E: The product from Step D (70 mg, 0.27 mmol) was treated with ethereal HCl (1.0 M, 0.6 ml, 0.6 mmol) in methanol (1.4 ml) to afford a precipitate. The solvents and excess HCl were removed in vacuo and the resultant solid recrystallized from methanol/diethyl ether to provide the HCl salt of the target (53 mg) as a white solid: mp 230–233° C.; $^1$H NMR (300 MHz, CD$_3$OD) δ 7.36–7.28 (m, 3H), 6.99–6.90 (m, 4H), 4.67 (dd, J=6.0, 6.0 Hz, 1H), 4.58 (bs, 1H), 3.87 (dd, J=6.0, 6.0 Hz, 1H), 3.57 (m, 1H), 3.08 (s, 3H); IR (KBr) 2931, 2473, 1625, 1598, 1462, 1119 cm$^{-1}$; CI MS m/z=260 [C$_{16}$H$_{15}$F$_2$N+H]$^+$; Anal. Calcd. for C$_{16}$H$_{15}$F$_2$N— HCl-0.1H$_2$O: C, 64.58; H, 5.49; N, 4.71. Found: C, 64.45; H, 5.43; N, 4.49.

Example 85

Preparation of (3,5-difluoro)-4-phenyl-1,2,7-trimethyl-1,2,3,4-tetrahydroisoquinoline Step A: Nitromethane (1.6 mL, 30 mmol) was added dropwise to an ice-cold solution of tetrabutylammonium fluoride (7.5 mmol) in dry THF (20 mL). A solution of 3,5-difluorobenzaldehyde (2.85 g, 20.1 mmol) in dry THF (5 mL) was added dropwise. Triethylamine (2.8 mL, 20 mmol)

was then added dropwise. A solution of tert-butyldimethylsilyl chloride (4.54 g, 30.1 mmol) in dry THF (15 mL) was added dropwise, causing a white precipitate to form. The reaction was stirred at 0° C. for 30 min and then was filtered. The solid was washed with ether/hexanes. The filtrate was washed (2×) with water. The organic layer was dried over $MgSO_4$, filtered, and concentrated under reduced pressure leaving a yellow oil. The yellow oil was purified by column chromatography on silica gel (300 g) eluting with 30% EtOAc/hexanes to give compound the product (2.65 g, 65%) as a colorless oil: $^1$H NMR (300 MHz, $CDCl_3$) δ 6.98–6.95 (m, 2H), 6.80 (tt, J=8.8, 2.3 Hz, 1H), 5.49–5.44 (m, 1H), 4.56–4.53 (m, 2H), 3.00 (d, J=2.9 Hz, 1H).

Step B: A slurry of the product from Step A (2.35 g, 11.6 mmol) and platinum oxide (0.20 g) in solute ethanol (20 mL) was hydrogenated at 40 psig for 4 h. The reaction was filtered throgh a plug of Celite, which was washed with additional absolute ethanol. The solvent was removed in vacuo leaving the amine product (1.97 g, 98%) as a white solid: mp 54–58° C.; $^1$H NMR (300 MHz, $CD_3OD$) δ 7.01–6.98 (m, 2H), 6.87–6.81 (m, 1H), 4.70 (dd, J=8.2, 3.8 Hz, 1H), 2.90 (dd, J=13.0, 3.8 Hz, 1H), 2.76 (dd, J=13.0, 8.2 Hz, 1H).

Step C: A solution of 3-methylacetophenone (1.36 g, 10.1 mmol) and the product from Step B (1.75 g, 10.1 mmol) in toluene (20 mL) was heated at reflux with azeotropic removal of water for 4 h under nitrogen. The toluene was removed in vacuo leaving an orange oil. To an ice-cold solution of the orange oil in methanol (10 mL), was added $NaBH_4$ (0.44 g, 12 mmol). The reaction was stirred for 1 h at 0° C. and then slowly allowed to warm to room temperature over 4 h. The reaction was concentrated under reduced pressure. The residue was taken up in water and extracted (3×) with ether. The combined organic extracts were dried over $NaSO_4$, filtered, and concentrated in vacuo to give the product as a mixture of diastereomers (3.00 g, >100%) as a yellow oil: $^1$H NMR (300 MHz, $CDCl_3$) δ 7.22–7.18 (m, 2H), 7.08–7.06 (m, 2H), 6.91–6.81 (m, 2H), 6.70–6.64 (m, 1H), 4.69–4.45 (m, 1H), 3.813.67 (m, 1H), 2.83–2.75 (m, 1H), 2.58–2.40 (m, 1H), 2.34 (s, 3H), 1.39–1.36 (m, 3H).

Step D: Concentrated $H_2SO_4$ (12.0 mL) was added to a stirred, ice-cold solution of the crude product from Step C (3.00 g, 10.3 mmol) in $CH_2Cl_2$ (105 mL). After stirring 15 min, the mixture was poured onto ice, made strongly alkaline with excess conc. $NH_4OH$, and extracted (2×) with $Et_2O$. The combined organic extracts were dried over $Na_2SO_4$, filtered, and the solvent was removed in vacuo. The residue (1.75 g) was purified by column chromatography on silica gel (145 g) eluting with 10% EtOAc/hexanes containing 1% $Et_3N$ and then 20% EtOAc/hexanes containing 1% $Et_3N$ to afford the product, a mixture of diastereomers, (426 mg, 15%) as a yellow oil: $^1$H NMR (300 MHz, $CDCl_3$) δ 7.046.61 (m, 6H), 4.22–3.99 (m, 2H), 3.49–3.29 (m, 1H), 3.19–2.92 (m, 1H), 2.34–2.32 (m, 3H), 1.52–1.47 (m, 3H).

Step E: Formaldehyde (37 wt %, 0.70 mL, 9.4 mmol) was added to a solution of the product from Step D (426 mg, 1.56 mmol) in methanol (16 mL). After 1.5 h, Raney nickel (0.51 g) was added, and the reaction was hydrogenated at 35 psig for 21 h. The reaction was filtered through a pad of Celite, which was washed with methanol. The filtrate was evaporated in vacuo, leaving a milky liquid, which was extracted with ether. The ether extract was dried over $Na_2SO_4$, filtered, and the solvent was removed in vacuo. The residue (392 mg) was purified by column chromatography on silica gel (150 g) eluting with 10% EtOAc/hexanes containing 1% $Et_3N$ to give the desired compound (82 mg, 18%) as a colorless oil.: $^1$H NMR (300 MHz, $CDCl_3$) δ 6.97 (s, 1H), 6.92 (d, J=7.7 Hz, 1H), 6.78–6.61 (m, 4H), 4.11 (t, J=6.4 Hz, 1H), 3.65 (q, J=6.6 Hz, 1H), 3.04–2.86 (m, 2H), 2.45 (s, 3H), 2.32 (s, 3H), 1.45 (d, J=6.6 Hz, 3H).

Step F: A 1 M HCl solution in ether (1.0 mL, 1.0 mmol) was added dropwise to a stirred solution of of the product from Step E (82 mg, 0.28 mmol) in methanol (3 mL). After 30 min, the solvents and excess HCl were removed in vacuo, and the residue precipitated from ether and sonicated for 30 min. The off-white solid was isolated by filtration and then dried at room temperature under vacuum for 24 h to give the product (78 mg, 83%) as an off-white solid: mp 194–197° C. (with decomposition); $^1$H NMR (300 MHz, $CD_3OD$) δ 7.14–7.12 (m, 2H), 7.00–6.81 (m, 4H), 4.65–4.59 (m, 2H), 3.66–3.64 (m, 2H), 3.03 (s, 3H), 2.35 (s, 3H), 1.75 (d, J=6.5 Hz, 3H); IR (KBr) 2928, 2480, 1624, 1599, 1464, 1119, 975, 859 cm$^{-1}$; CI MS m/z=288 $[C_{18}H_{19}F_2N+H]^+$; HPLC>99%, $t_r$=16.96 min; Anal. Calcd. for $C_{18}H_{19}F_2N$—HCl-0.25$H_2O$: C, 65.85; H, 6.29; N, 4.27. Found: C, 65.98; H, 6.12; N, 4.16.

Example 89

Preparation of (8-fluoro-2-methyl-4-phenyl-1,2,3,4-tetrahydro-7-isoquinolinyl)-N-methylmethanamine Step A: Methylamine (15.3 mL, 40% aq. solution, 177 mmol) was added to a stirred solution of 3-fluorobenzaldehyde (20.0 g, 161 mmol) in MeOH (150 mL) at room temperature. After stirring for 6 h, the reaction was cooled to 0° C. and then $NaBH_4$ (6.10 g, 161 mmol) was added portionwise. The cooling bath was removed and the reaction was warmed to room temperature and stirred for 16.5 h. The reaction was quenched with $H_2O$, and cautiously acidified with 2 N HCl, and then extracted (3×) with $CH_2Cl_2$. The aq. phase was then basified using 6 N NaOH and then extracted (4×) with $CH_2Cl_2$. The latter organic extracts were combined, dried over $NA_2SO_4$, filtered, and concentrated in vacuo to afford the product (21.51 g, 96%), as a clear oil: $^1$H NMR (300 MHz, $CDCl_3$) δ 7.32 (td, J=7.5, 1.7 Hz, 1H), 7.28–7.19 (m, 1H), 7.14–6.98 (m, 2H), 3.80 (s, 2H), 2.45 (s, 3H), 1.47 (br s, 1H).

Step B: Triethylamine (8.40 mL, 60.0 mmol) was added to a stirred solution of the product from Step A (8.35 g, 60.0 mmol) and phenacyl bromide (11.94 g, 60.0 mmol) in $CH_2Cl_2$ (200 mL) at room temperature under $N_2$. After stirring for 18 h, the reaction was quenched with a mixture 10:1 mixture of $H_2O$/6 N NaOH (33 mL) and organic layer was dried over $NASO_4$, filtered, and the solvent evaporated in vacuo, affording crude product (17.08 g, theoretical=15.44 g), as a yellow oil: $^1$H NMR (300 MHz, $CDCl_3$) δ 8.00–7.94 (m, 2H), 7.59–7.52 (m, 1H), 7.48–7.37 (m, 3H), 7.30–7.21 (m, 1H), 7.15–7.10 (m, 2H), 3.85 (s, 2H), 3.79 (s, 2H), 2.39 (s, 3H); IR ($CH_2Cl_2$ solution) 3055, 2925, 2850, 1682, 1598, 1490, 1450, 1266, 1225, 738, 703 cm$^{-1}$; CI MS m/z=258 $[C_{16}H_{16}FNO+H]^+$. This material was used without further manipulation.

Step C: Sodium borohydride (4.54 g, 120 mmol) was added portionwise to a stirred solution of the product from Step B (17.1 g, ~60.0 mmol) in MeOH (150 mL), cooled to 0° C. under $N_2$. After stirring for 4.5 h at room temperature, the reaction was diluted with $H_2O$ (300 mL) and extracted (4×) with $CH_2Cl_2$. The organic extracts were combined, washed with sat. NaCl, dried over $Na_2SO_4$, filtered, and the solvent evaporated in vacuo. Chromatography of the residual yellow oil (15.81 g) using silica (200 g) and elution with 50% EtOAc/hexanes afforded the product (14.81 g, 95% over 2 steps), as a yellow oil: $^1$H NMR (300 MHz, CDCl$_3$) δ 7.39–7.22 (m, 7H), 7.15–7.01 (m, 2H), 4.75 (dd, J=8.3, 5.6 Hz, 1H), 3.79(d, J=13.3 Hz, 1H), 3.64 (d, J=13.3 Hz, 1H), 2.65–2.53 (m, 2H), 2.33 (s, 3H); IR (CH$_2$Cl$_2$ solution) 3062, 2849, 1587, 1491, 1455, 1333, 1266, 1228, 1094, 1062, 1023, 897, 877, 758, 738, 701 cm$^{-1}$; CI MS m/z=260 [C$_{16}$H$_{18}$FNO+H]$^+$.

Step D: Conc. sulfuric acid (24 mL) was added dropwise to a stirred solution of the product from Step C (14.8 g, 57.1 mmol) in CH$_2$Cl$_2$ (280 mL), cooled to 0° C., using an ice-water bath. The cooling bath was removed after addition was complete and the reaction was vigorously stirred at room temperature for 20 min. The reaction was then poured into an ice/water mixture (400 mL) and the resultant mixture basified with conc. NH$_4$OH solution to pH ~10. The aq. layer was extracted (3×) with CH$_2$Cl$_2$. The organic extracts were combined, washed with a 2:1 mixture of sat. NaCl/1 N NaOH, dried over Na$_2$SO$_4$, filtered and concentrated in vacuo. Chromatography of the residue (13.91 g) on silica (450 g) and elution with 33% EtOAc/hexanes afforded the product (12.66 g, 92%), as a yellow oil: $^1$H NMR (300 MHz, CDCl$_3$) δ 7.33–7.15 (m, 5H), 7.08–6.98 (m, 1H), 6.90–6.82 (m, 1H), 6.66 (d, J=7.7 Hz, 1H), 4.30–4.22 (m, 1H), 3.86 (d, J=15.6 Hz, 1H), 3.53 (d, J=15.6 Hz, 1H), 3.02 (dd, J=11.4, 5.6, 1.1 Hz, 1H), 2.57 (dd, J=11.6, 8.7 Hz, 1H), 2.47 (s, 3H); IR (CH$_2$Cl$_2$ solution) 2941, 2782, 1583, 1494, 1468, 1457, 1378, 1248, 1139, 1040, 887, 792, 764, 736, 701 cm$^{-1}$; CI MS m/z=242 [C$_{16}$H$_{18}$FN+H]$^+$.

Step E: t-Butyl lithium (30 mL, 1.7 M in pentane, 50.5 mmol) was added dropwise to a stirred solution of the product from Step D (5.50 g, 22.8 mmol) and TMEDA (7.6 mL, 50.2 mmol) in Et$_2$O (120 mL) cooled to –60° C. under N$_2$. After stirring for 45 min, DMF (7.0 mL, 91.2 mmol) was added and the reaction mixture was stirred at –60° C. for 1.5 h. The reaction was quenched with MeOH (10 mL), warmed to room temperature, and then diluted with H$_2$O (200 mL) and the aqueous layer was extracted (4×) with CH$_2$Cl$_2$. The combined CH$_2$Cl$_2$ extract was dried over Na$_2$SO$_4$, filtered and concentrated in vacuo. Chromatography of the residue (9.05 g) on silica (350 g) and elution with 33% EtOAc/hexanes afforded the product (1.21 g, 20%), as a brown oil: $^1$H NMR (300 MHz, CDCl$_3$) δ 10.32 (s, 1H), 7.56 (t, J=7.6 Hz, 1H), 7.34–7.21 (m, 3H), 7.19–7.10 (m, 2H), 6.79 (d, J=8.2 Hz, 1H), 4.31–4.23 (m, 1H), 3.90 (d, J=15.8 Hz, 1H), 3.58 (d, J=15.8 Hz, 1H), 3.04 (dd, J=11.9,5.6,1.0 Hz, 1H), 2.61 (dd, J=11.7, 8.3 Hz, 1H), 2.49 (s, 3H); CI MS m/z=270 [C$_{17}$H$_{16}$FNO+H]$^+$.

Step F: Methylamine (0.05 mL, 40% aq. solution, 0.62 mmol) was added to a stirred solution of impure aldehyde 147 (0.15 g, ~0.57 mmol) in MeOH (3 mL) at room temperature. After stirring for 6 h, the reaction was cooled to 0° C. and then NaBH$_4$ (0.022 g, 0.57 mmol) was added. The cooling bath was removed and the reaction was warmed to room temperature and stirred for 18 h. The reaction was quenched with H$_2$O extracted (4×) with CH$_2$Cl$_2$. The organic extracts were combined, dried over NaSO$_4$, filtered, and concentrated in vacuo. Chromatography of the residue (0.18 g) using silica (10 g) and elution with 88:12:1 CHCl$_3$:MeOH:conc. NH$_4$OH afforded methylamine 147 (0.10 g), as a brown oil: $^1$H NMR (300 MHz, CDCl$_3$) δ 7.32–7.12 (m, 5H), 7.02 (t, J=7.8 Hz, 1H), 6.63 (d, J=7.9 Hz, 1H), 4.28–4.20 (m, 1H), 3.86 (d, J=15.6 Hz, 1H), 3.75 (s, 2H), 3.52 (d, J=15.6 Hz, 1H), 3.00 (dd, J=11.3, 5.6, 0.9 Hz, 1H), 2.55 (dd, J=11.5, 8.7 Hz, 1H), 2.46 (s, 3H), 2.4s, 3H); CI MS m/z=285 [C$_{18}$H$_{21}$FN$_2$+H]$^+$.

Step G: An ethereal HCl solution (1.80 mL, 1 N, 1.80 mmol) was added to a solution of the product from Step F (0.10 g, 0.35 mmol) in MeOH (0.5 mL) and Et$_2$O (5 mL) at room temperature, resulting in the formation of a off-white solid. The solid was isolated and then recrystallized from MeOH/Et$_2$O (3×) and the solid was dried in vacuo (54° C.) to afford the salt (0.083 g, 66%) as a light green solid: mp 185–205° C.; $^1$H NMR (300 MHz, CD$_3$OD) δ 7.50–7.24 (m, 6H), 6.86–6.78 (m, 1H), 4.80–4.50 (m, 3H), 4.29 (s, 2H), 3.92–3.83 (m, 1H), 3.70–3.55 (m, 1H), 3.15 (s, 3H), 2.76 (s, 3H); IR (KBr) 3422, 2956, 2698, 1635, 1497, 1456, 1218, 1032, 895, 770, 703, 560 cm$^{-1}$; CI MS m/z=285 [C$_{18}$H$_{21}$FN$_2$+H]$^+$; HPLC 95.5%, t, =10.96 min; Anal. Calcd. for C$_{18}$H$_{21}$FN$_2$·2HCl·0.5H$_2$O: C, 59.02; H, 6.60; N, 7.65. Found: C, 59.13; H, 6.73; N, 7.42.

Example 90

Preparation of (2-methyl-4-phenyl-7-isoquinolinyl)-N-methylmethanamine

Step A: Methylamine (40 wt % aqueous, 2.6 mL, 30 mmol) was added to a stirred solution of 3-bromobenzaldehyde (5.44 g, 29.4 mmol) in MeOH (30 mL) under N$_2$. After stirring 1 h, the colorless solution was cooled to 0° C. and then NaBH$_4$ (0.60 g, 16 mmol) was added portionwise. After stirring 1 h, the cooling bath was removed. After stirring for 90 min, the reaction was cooled to 0° C. and then phenacyl bromide (5.90 g, 29.6 mmol) was added portionwise over 30 min. The reaction was allowed to warm to room temperature. After stirring for 2 h at room temperature, the solution was cooled to 0° C. and then NaBH$_4$ (1.20 g, 31.7 mmol) was added portionwise over 10 min. The solution was stirred for 24 h, during which time the temperature rose from 0° to 25° C. The solution was diluted with H$_2$O (400 mL), extracted (4×) with ether. The ether extracts were dried over Na$_2$SO$_4$, filtered, and the solvent removed in vacuo to give the product (9.21 g, 98%) as a yellow oil: $^1$H NMR (300 MHz, CDCl$_3$) δ 7.47–7.21 (m, 9H), 4.77(dd, J=10.0,4.0 Hz, 1H), 3.71 (d, J=13.3 Hz, 1H), 3.51 (d, J=13.3 Hz, 1H), 2.61–2.49 (m, 2H), 2.32 (s, 3H).

Step B: Conc. H$_2$SO$_4$ (40.0 mL) was added dropwise over 15 min to a stirred solution of the product from Step A (9.18 g, 28.7 mmol) in CH$_2$Cl$_2$ (300 mL). After stirring 45 min, the mixture was poured onto ice, made strongly alkaline with excess conc. NH$_4$OH, extracted (3×) with Et$_2$O. The ether extracts were dried over NaSO$_4$, filtered, the solvent was removed in vacuo, and the residue (7.29 g) was purified by column chromatography on silica gel (300 g) eluting with 10% EtOAc/hexanes containing 1% Et$_3$N the product (2.05 g, 24%) as an orange oil: $^1$H NMR (300 MHz, CDCl$_3$) δ 7.32–7.27 (m, 4H), 7.25–7.14 (m, 3H), 6.74 (d, J=8.3 Hz, 1H), 4.22–4.17 (m, 1H), 3.71 (d, J=15.1 Hz, 1H), 3.57 (d, J=15.1 Hz, 1H), 3.05–2.99 (m, 1H), 2.54 (dd, J=11.5, 8.7 Hz, 1H), 2.42 (s, 3H).

Step C: A slurry of bromide the product from Step B (1.15 g, 3.81 mmol), zinc cyanide (271 mg, 2.31 mmol), and tetrakis(triphenylphosphine)palladium(0) (266 mg, 0.230 mmol) in dry DMF (5 mL) was heated at 83° C. for 24 h. After allowing the reaction to cool to room temperature, the reaction was diluted with toluene and washed with 2 N NaOH. The toluene extract was dried over Na$_2$SO$_4$, filtered, and concentrated in vacuo. The residue (1.20 g) was purified by column chromatography on silica gel (95 g) eluting with 20% EtOAc/hexanes containing 1% Et$_3$N to give the product (673 mg, 71%) as a yellow solid: mp 103–104° C.; $^1$H NMR (500 MHz, CDCl$_3$) δ 7.38 (s, 1H), 7.34–7.23 (m, 4H), 7.16–7.14 (m, 2H), 6.98 (d, J=8.0 Hz, 1H), 4.27 (t, J=7.0 Hz, 1H), 3.75 (d, J=15.2 Hz, 1H), 3.61 (d, J=15.2Hz, 1H), 3.07–3.03 (m, 1H), 2.59 (dd, J=11.7, 8.4 Hz, 1H), 2.44 (s, 3H); CI MS m/z=249 $[C_{17}H_{16}N_2+H]^+$.

Step D: A solution of the product from Step C (201 mg, 0.809 mmol) in dry THF (4 mL) was added dropwise to an ice-cold slurry of lithium aluminum hydride (61 mg, 1.6 mmol) in dry THF (2 mL). The reaction was stirred for 90 min with cooling and then was allowed to warm to room temperature. The reaction was stirred for 5 h and then was quenched with EtOAc and then a saturated $Na_2SO_4$ solution. The reaction was diluted with ether, dried over solid $Na_2SO_4$, filtered, and concentrated in vacuo. The residue was purified by column chromatography on silica gel (26 g) eluting with 12% methanol/chloroform containing 1% conc. $NH_4OH$ to give the product (134 mg, 66%) as a colorless oil: $^1H$ NMR (300 MHz, $CDCl_3$) δ 7.31–7.18 (m, 5H), 7.04 (s, 1H), 7.00 (d, J=8.0 Hz, 1H), 6.83 (d, J=8.0 Hz, 1H), 4.25 (t, J=7.0 Hz, 1H), 3.81 (s, 2H), 3.75 (d, J=14.9 Hz, 1H), 3.60 (d, J=14.9 Hz, 1H), 3.06–3.00 (m, 1H), 2.56 (dd, J=11.4, 8.7 Hz, 1H), 2.43 (s, 3H).

Step E: A slurry of the product from Step D (53 mg, 0.21 mmol) and maleic acid (25 mg, 0.22 mmol) in absolute EtOH (10 mL) was heated in a 40° C. water bath until all of the solid had dissolved. After 1 h, the reaction was concentrated in vacuo. The residue was recrystallized from ethanol/ether producing the bis maleate salt (43 mg, 42%) as a green solid: mp 176–177° C. (with decomposition); $^1H$ NMR (300 MHz, $CD_3OD$) δ7.40–7.30 (m, 5H), 7.22 (dd, J=8.0, 1.3 Hz, 2H), 6.97 (d, J=8.0 Hz, 1H), 6.24 (s, 4H), 4.58 (dd, J=11.3, 6.1 Hz, 1H), 4.52 (s, 2H), 4.12 (s, 2H), 3.78 (dd, J=12.3, 6.2 Hz, 1H), 3.45 (t, J=11.8 Hz, 1H), 3.02 (s, 3H); HPLC 95.8%, t, =10.81 min; Anal. Calcd. for $C_{17}H_{20}N_2$—$2(C_4H_4O_4)$: C, 61.98; H, 5.82; N, 5.78. Found: C, 61.86; H, 5.82; N, 5.60.

Example 91

Preparation of N-methyl(2-methyl-4-phenyl-7-isoquinolinyl)-N-methylmethanamine

Step A: A 1 M HCl solution in ether (3.0 mL, 3.0 mmol) was added dropwise to a solution of the product from Step C, Example 90 (82 mg, 0.32 mmol) in methanol (6 mL). The solvents and excess HCl were removed in vacuo leaving a green solid. A slurry of this green solid, potassium carbonate (199 mg, 1.44 mmol), and ethyl chloroformate (0.20 mL, 2.1 mmol) in methanol (1 mL) and acetone (6 mL) was heated at 50° C. for 20 h. After allowing the reaction to cool to room temperature, the reaction was diluted with brine and extracted (4x) with EtOAc. The combined organic extracts were dried over solid $Na_2SO_4$, filtered, and concentrated in vacuo leaving the carbamate product (99 mg, 88%) as an orange oil: $^1H$ NMR (300 MHz, $CDCl_3$)δ 7.31–7.14 (m, 5H), 6.98–6.93 (m, 2H), 6.83–6.76 (m, 1H), 4.30–4.10 (m, 5H), 3.77–3.58 (m, 2H), 3.07–3.01 (m, 1H), 2.61–2.54 (m, 1H), 2.43 (s, 3H), 1.24 (t, J=7.1 Hz, 3H); CI MS m/z=325 $[C_{20}H_{24}N_2O_2+H]^+$.

Step B: Lithium aluminum hydride (60 mg, 1.6 mmol) was added in portions to a solution of the product from Step A (99 mg, 0.30 mmol) in dry THF (5 mL). The reaction was heated at reflux for 6 h and then allowed to cool to room temperature. The reaction was quenched with EtOAc and then a saturated $Na_2SO_4$ solution. The reaction was diluted with ether, dried over solid $Na_2SO_4$, filtered, and concentrated in vacuo. The residue (81 mg) was purified by column chromatography on silica gel (8 g) eluting with 12% methanol/chloroform containing 1% conc. $NH_4OH$ to give compound the product (49 mg, 61%) as a colorless oil: $^1H$ NMR (300 MHz, $CDCl_3$) δ 7.32–7.17 (m, 5H), 7.04 (s, 1H), 7.00 (d, J=8.0 Hz, 1H), 6.82 (d, J=8.0 Hz, 1H), 4.26 (t, J=7.1 Hz, 1H), 3.83–3.57 (m, 4H), 3.0.7–3.01 (m, 1H), 2.54 (dd, J=11.4, 8.9 Hz, 1H), 2.45 (s, 3H), 2.43 (s, 3H); CI MS m/z=267 $[C_{18}H_{22}N_2+H]^+$.

Step C: A slurry of the product from Step B (20 mg, 0.075 mmol) and maleic acid (9 mg, 0.08 mmol) in absolute EtOH (5 mL) was heated in a 40° C. water bath until all of the solid had dissolved. After 2 h, the reaction was concentrated in vacuo. The residue was recrystallized from ethanol/ether producing the bis maleate product (13 mg, 35%) as a tan solid: mp 160–163° C. (with decomposition); $^1H$ NMR (300 MHz, $CD_3OD$) δ 7.41–7.31 (m, 5H), 7.24–7.21 (m, 2H), 6.99 (d, J=8.0 Hz, 1H), 6.24 (s, 4H), 4.57 (dd, J=10.9, 5.7 Hz, 1H), 4.50 (s, 2H), 4.18 (s, 2H), 3.76 (dd, J=12.3, 6.2 Hz, 1H), 3.50–3.38 (m, 1H), 3.00 (s, 3H), 2.72 (s, 3H); HPLC 95.8%, t, =11.09 min.

Example 92

Preparation of 8-hydroxy-2-methyl-4-phenyl-1,2,3,4-tetrahydro-7-isoquinolinecarbonitrile Step A: A solution of N-methyl-2-methoxy amine (8.00 g, 52.9 mmol) and triethylamine (5.40 g, 53.0 mmol) in dichloromethane (100 mL) was cooled in an ice water bath. The 2-bromoacetophenone (10.5 g, 53.0 mmol) was added, and the reaction was allowed to warm to room temperature. The reaction mixture was diluted with water (200 mL) and MTBE (200 mL). Layers were separated, and the organic layer was washed with $H_2O$ and brine. The organic layer was dried over $MgSO_4$, filtered, and concentrated to yield a red oil which was chromatographed ($SiO_2$, 20% EtOAc/hexanes) to yield the desired amino ketone as a yellow oil (12.6 g, 89%): $^1H$ NMR (300 MHz, $CDCl_3$) δ 7.97 (d, J=7.4 Hz, 2H), 7.53–7.50 (m, 1H), 7.41 (t, J=7.5 Hz, 2H), 7.32 (d, J=7.4 Hz, 1H), 7.28–7.21 (m, 1H), 6.92 (t, J=7.5 Hz, 1H), 6.85 (d, J=8.1 Hz, 1H), 3.81 (s, 2H), 3.77 (s, 3H), 3.73 (s, 2H), 2.39 (s, 3H).

Step B: The product from Step A (12.6 g, 46.8 mmol) was taken up in methanol (120 mL) and cooled in an ice-water bath. Sodium borohydride (1.76 g, 46.8 mmol) was added portionwise. The reaction was stirred for 1 h at ambient temperature. The reaction mixture was concentrated to half of the original volume. Water (110 mL) was added, and the mixture was extracted (3x) with dichloromethane. The combined organic layers were dried over $MgSO_4$, filtered, and concentrated to provide the desired amino alcohol as a light yellow oil (10.0 g, 79%): $^1H$ NMR (300 MHz, $CDCl_3$) δ 7.39–7.21 (m, 6H), 6.94–6.85 (m, 3H), 4.78 (dd, J=4.3, 9.6 Hz, 1H), 3.85 (s, 3H), 3.82 (d, J=12.8 Hz, 1H), 3.47 (d, J=12.8 Hz, 1H), 2.62–2.57 (m, 2H), 2.28 (s, 3H).

Step C: Methanesulfonic acid (47.7 mL, 735 mmol) was added at ambient temperature to a solution of the product from Step B (4.20 g, 13.7 mmol) in dichloromethane (250 mL). The reaction mixture was stirred at room temperature under nitrogen for 24 h. After the reaction was complete, the reaction was made basic (pH~11) with 2 N NaOH, and extracted (3x) with methylene chloride. The combined organic layers were washed with brine, dried over $MgSO_4$ and concentrated in vacuo. The residue was purified by chromatography ($SiO_2$, EtOAc/hexanes, 2/3) to give the desired product as a yellow oil (5.67 g, 61%): $^1H$ NMR (300 MHz, $CDCl_3$) δ 7.30–7.15 (m, 5H), 7.02 (t, J=8.0 Hz, 1H), 6.65 (d, J=8.1 Hz, 1H), 6.47 (d, J=7.6 Hz, 1H), 4.25 (t, J=6.8 Hz, 1H), 3.82 (s, 3H), 3.81 (d, J=16.2 Hz, 1H), 3.36 (d, J=16.2 Hz, 1H), 2.96 (dd, J=4.1, 15.3 Hz, 1H), 2.58 (dd, J=8.5, 11.4 Hz, 1H), 2.43 (s, 3H).

Step D: A solution of the product from Step C (5.60 g, 22.1 mmol) in 48% hydrobromic acid (60 mL) was refluxed at 100° C. for 3 h. The reaction mixture was concentrated in vacuo and recrystallized from ethanol to yield the desired product (4.74 g, 67): $^1$H NMR (300 MHz, DMSO-$d_6$) δ 9.92 (s, 1H), 7.48–7.25 (m, 3H), 7.21 (d, J=7.8 Hz, 1H), 6.98 (t, J=7.7 Hz, 1H), 6.67 (d, J=7.8 Hz, 1H), 6.24 (d, J=7.7 Hz, 1H), 4.26 (t, J=6.0 Hz, 1H), 3.80 (d, J=15.8 Hz, 1H), 3.32 (d, J=15.8 Hz, 1H), 2.99 (dd, J=5.2, 11.3 Hz, 1H), 2.66 (dd, J=7.1, 11.4 Hz, 1H), 2.39 (s, 3H).

Step E: A mixture of the product from step D (4.70 g, 14.7 mmol) and hexamethylenetetramine (2.06 g, 14.7 mmol) in trifluoroacetic acid (50 mL) was heated to 80° C. for 7 h. The reaction mixture was concentrated in vacuo then diluted with water (100 mL). The solution was made basic with solid $Na_2CO_3$. The resulting solution was extracted with ethyl ether (3×), and the combined organic layers were concentrated in vacuo. The residue was purified by chromatography ($SiO_2$, EtOAc/hexanes, 4/1) to afford the desired product as an off-white solid (2.47 mg, 49%): $^1$H NMR (500 MHz, $CDCl_3$) δ 11.42 (bs, 1H), 9.82 (s, 1H), 7.28 (d, J=8.1 Hz, 1H), 7.12–6.90 (m, 3H), 6.54 (d, J=8.1 Hz, 1H), 4.19 (d, J=6.1 Hz, 1H), 3.72 (d, J=16.1 Hz, 1H), 3.62 (d, J=16.2 Hz, 1H), 2.93 (dd, J=11.9, 6.28 Hz, 1H), 2.60 (dd, J=11.4, 7.0 Hz, 1H), 2.47 (s, 3H).

Step F: The product from Step E (1.00 g, 2.87 mmol) was dissolved in water (20 mL) before treatment with sodium sulfate (100 mg) and hydroxylamine sulfonate (0.32 mg 2.87 mmol). Reaction was stirred for 2 h. Reaction was cooled in an ice-water bath and treated with $CH_2Cl_2$ (20 mL). Sodium bicarbonate (600 mg) was added and the reaction was allowed to warm to ambient temperature. The solids were filtered off and combined with the organic layer. The mixture was concentrated and chromatographed ($SiO_2$, EtOAc/hexanes, 1/1). Two compounds eluted simultaneously. The mixture was treated with ethanol (5 mL) and filtered. The filtrate was concentrated to yield the desired nitrile as an off-white powder (130 mg, 17%): mp 234–238° C. (decomposed); $^1$H NMR (300 MHz, $CD_3OD$) δ 7.31–7.14 (m, 6H), 6.40 (d, J=8.1 Hz, 1H), 4.21 (t, J=6.1 Hz, 1H), 4.12 (bs, 1H), 3.61–3.50 (m, 2H), 2.72 (dd, J=5.4, 11.7 Hz, 1H), 2.58 (dd, J=7.1, 11.5 Hz, 1H), 2.38 (s, 3H). IR (KBr) 3427, 3026, 2940, 2207, 1590, 1454 cm$^{-1}$; ESI MS m/z=265 $[C_{17}H_{16}N_2O+H]^+$; HPLC 96.3%, t,=13.54 min.

Example 93

Preparation of (2-methyl-4-phenyl-1,2,3,4-tetrahydro-7-isoquinolinyl)methanol

Step A: A solution of Step C, Example 90 (127 mg, 0.511 mmol) in dry toluene (13 mL) was cooled to −16° C. and then 1 M DIBAL-H in toluene (1.7 mL, 1.7 mmol) was added dropwise. The reaction was stirred for 45 min with cooling and then EtOAc (1.1 mL) was added. The reaction was allowed to warm to room temperature. The reaction was stirred for 45 min and then 1 N $H_2SO_4$ (12 mL) was added. The reaction was heated at reflux for 30 min. After allowing the reaction to cool to room temperature, the reaction was diluted with water, made basic with 2 N NaOH, and extracted (2×) with $CH_2Cl_2$. The $CH_2Cl_2$ extracts were dried over $Na_2SO_4$, filtered, and concentrated in vacuo to give the desired product (112 mg, 87%) as a yellow oil: $^1$H NMR (300 MHz, $CDCl_3$) δ 9.95 (s, 1H), 7.62 (s, 1H), 7.59–7.56 (m, 1H), 7.34–7.16 (m, 5H), 7.05 (d, J=8.0 Hz, 1H), 4.32 (t, J=7.1 Hz, 1H), 3.84 (d, J=15.1 Hz, 1H), 3.67 (d, J=15.1 Hz, 1H), 3.10–3.04 (m, 1H), 2.60 (dd, J=11.6, 8.6 Hz, 1H), 2.46 (s, 3H).

Step B: To an ice-cold solution of the product from Step A (110 mg, 0.438 mmol) in methanol (20 mL) was added $NaBH_4$ (36 mg, 0.95 mmol). The reaction was slowly allowed to warm to room temperature overnight. The reaction was quenched with water and brine and then was extracted (3×) with $CH_2Cl_2$. The combined organic extracts were dried over $NASO_4$, filtered, and concentrated under reduced pressure. The residue (106 mg) was purified by column chromatography on silica gel (31 g) eluting with EtOAc to give the desired alcohol (44 mg, 40%) as a yellow oil: $^1$H NMR (300 MHz, $CDCl_3$) δ 7.32–7.22 (m, 3H), 7.17 (dd, J=6.6, 1.6 Hz, 2H), 7.03 (d, J=7.6 Hz, 1H), 7.02 (s, 1H), 6.83 (d, J=7.6 Hz, 1H), 4.61 (s, 2H), 4.26 (dd, J=8.6, 6.0 Hz, 1H), 3.69 (d, J=14.9 Hz, 1H), 3.55 (d, J=14.9 Hz, 1H), 3.07–3.01 (m, 1H), 2.53 (dd, J=11.5, 9.1 Hz, 1H), 2.42 (s, 3H).

Step C: A 1 M HCl solution in ether (1.0 mL, 1.0 mmol) was added dropwise to a stirred solution of theproduct from Step B (44 mg, 0.17 mmol) in MeOH (2 mL). The solvents and excess HCl were removed in vacuo, and the residue recrystallized from MeOH-$Et_2O$ to give the salt (32 mg, 62%) as a green solid: mp 237–240° C. (with decomposition); $^1$H NMR (300 MHz, $CD_3OD$) δ 7.42–7.31 (m, 3H), 7.27–7.23 (m, 4H), 6.88 (d, J=7.2 Hz, 1H), 4.60 (bs, 5H) 3.84 (dd, J=12.4, 6.0 Hz, 1H), 3.65–3.45 (m, 1H), 3.08 (s, 3H); IR (KBr) 3356, 2934, 2596, 1495, 1456, 1428, 1049, 758, 703 cm$^{-1}$; ESI MS m/z=254 $[C_{17}H_{19}NO+H]^+$; HPLC 94.9%, t, =12.83 min; Anal. Calcd. for $C_{17}H_{19}NO$—HCl-0.33$H_2O$: C, 69.03; H, 7.04; N, 4.74. Found: C, 68.89; H, 6.87; N, 4.61.

Example 94

Preparation of 2-ethyl-4-phenyl-1,2,3,4-tetrahydroisoquinoline

Step A: Ethylene glycol dimethyl ether (20 mL) and 2 N $Na_2CO_3$ (12.2 mL) were sparged with $N_2$ and charged to a round bottom flask containing 4-bromoisoquinoline (2 g, 9.6 mmol), phenylboronic acid (1.76 g, 14.4 mmol), and $Pd(PPh_3)_4$ (1.11 g, 0.96 mmol). The entire solution was sparged with $N_2$. The resulting reaction mixture was heated to reflux under $N_2$ overnight. The solution was cooled, quenched with saturated $NaHCO_3$ (230 mL), and extracted five times with ethyl ether. The combined organic was dried over $NASO_4$, filtered, and the solvent was removed in vacuo to yield an orange oil. Column chromatography (1:1 ethyl acetate/hexanes) afforded the pure isoquinoline as a yellow oil which crystallized upon refrigeration (2.21 g). $^1$H NMR (300 MHz, $CDCl_3$) δ 9.29 (s, 1H), 8.52 (s, 1H), 8.04 (d, 1H, J=8.4 Hz), 7.91 (d, 1H, J=8.1 Hz), 7.66 (m, 2H), 7.46 (m, 5H).

Step B: Ethyl triflate (383 mg, 2.15 mmol) was added dropwise to a solution of the product mL from Step A (400 mg, 1.95 mmol) in $CH_2Cl_2$ (24 mL) at 0° C. under $N_2$. The solution was stirred for 15 min. at room temperature. The solvent was removed in vacuo to yield the triflate salt of the isoquinoline as a white solid (420 mg, 56% yield). The iriflate salt (420 mg, 1.09 mmol) was dissolved in MeOH (16 mL), and $NaCNBH_3$ (159 mg, 2.53 mmol) was added to the solution. The resulting reaction mixture was stirred for 5 min., and a few drops of bromocresol green in MeOH were added. Methanolic HCl was added to the solution until a yellow color was observed. The reaction mixture was stirred at room temperature for 30 min, while adding methanolic HCl as needed to maintain a yellow color. The reaction mixture was quenched with $H_2O$ (100 mL) and basified with 5% NaOH until a blue color was observed. The resulting solution was extracted four times with ethyl ether. The combined organic was washed with brine, dried over $MgSO_4$, filtered, and solvent was removed in vacuo to yield the tetrahydroisoquinoline product as a clear oil (140 mg, 30% yield).

Step C: The maleate salt was prepared by adding maleic acid (68 mg, 0.59 mmol) and EtOH (2 mL) to the product from Step B. After refrigeration and removal of EtOH, a white solid was obtained (130 mg), mp=172–174° C. Free base: $^1$H NMR $CDCl_3$ δ7.17 (m, 8H), 6.85 (d, 1H, J=7.7 Hz), 4.28 (t, 1H, J=7.5 Hz), 3.89 (d, 1H, J=14.65 Hz), 3.62 (d, 1H, J=14.65 Hz), 3.15 (dd, 1H, J=5.7, 11.7 Hz), 2.57 (m, 2H), 1.16 (t, 3H, J=7.2 Hz).

Binding Assays

Primary Binding Assays:

In order to evaluate the relative affinity of the various compounds at the NE, DA and 5HT transporters, HEK293E cell lines were developed to express each of the three human transporters. cDNAs containing the complete coding regions of each transporter were amplified by PCR from human brain libraries. The cDNAs contained in pCRII vectors were sequenced to verify their identity and then subcloned into an Epstein-Barr virus based expression plasmid (E. Shen, GM Cooke, RA Horlick, Gene 156:235–239, 1995). This plasmid containing the coding sequence for one of the human transporters was transfected into HEK293E cells. Successful transfection was verified by the ability of known reuptake blockers to inhibit the uptake of tritiated NE, DA or 5HT.

For binding, cells were homogenized, centrifuged and then resuspended in incubation buffer (50 mM Tris, 120 mM NaCl, 5 mM KCl, pH 7.4). Then the appropriate radioligand was added. For NET binding, [$^3$H] Nisoxetine (86.0 Ci/mmol, NEN/DuPont) was added to a final concentration of approximately 5 nM. For DAT binding, [$^3$H] WIN 35,428 (84.5 Ci/mmol) at 15 nM was added. For 5HTT binding, [$^3$H] Citolapram (85.0 Ci/mmol) at 1 nM was added. Then various concentrations (10○-5 to 10○-11M) of the compound of interest were added to displace the radioligand. Incubation was carried out at room temperature for 1 hour in a 96 well plate. Following incubation, the plates were placed on a harvester and washed quickly 4 times with (50 mM tris, 0.9% NaCl, pH 7.4) where the cell membranes containing the bound radioactive label were trapped on Whatman GF/B filters. Scintillation cocktail was added to the filters which were then counted in a Packard TopCount. Binding affinities of the compounds of interest were determined by non-linear curve regression using GraphPad Prism 2.01 software. Non-specific binding was determined by displacement with 10 micromolar mazindol.

TBZ Assay:

In order to assess in vivo activity of the compounds at the NE and DA transporters, their ability to prevent the sedative effects of tetrabenazine (TBZ) was determined (G. Stille, Arzn. Forsch 14:534537, 1964). Male CFI mice (Charles River Breeding Laboratories) weighing 18–25 gm at the time of testing, are housed a minimum of O6 days under carefully controlled environmental conditions (22.2+1.1 C; 50% average humidity; 12 hr lighting cycle/24 hr). Mice are fasted overnight (16–22 hr) prior to testing. Mice are placed into clear polycarbonated "shoe" boxes (17 cm×28.5 cm×12 cm). Randomized and coded doses of test compounds are administered p.o. A 45 mg/kg dose of tetrabenazine is administered i.p. 30 minutes prior to score time. All compounds are administered in a volume of 0.1 ml/10 gm body weight. Animals are evaluated for antagonism of tetrabenazine induced exploratory loss and ptosis at specified time intervals after drug administration. At the designated time interval, mice are examined for signs of exploratory activity and ptosis. Exploratory activity is evaluated by placing the animal in the center of a 5 inch circle. Fifteen seconds are allowed for the animal to move and intersect the perimeter. This is considered antagonism of tetrabenazine and given a score of 0. Failure to leave the circle is regarded as exploratory loss and given a score of 4. An animal is considered to have ptosis if its eyelids are at least 50% closed and given a score of 4 if completely closed. No closure is given a score of 0. Greater than 95% of the control (vehicle-treated) mice are expected to exhibit exploratory loss and ptosis. Drug activity is calculated as the percentage of mice failing to respond to the tetrabenazine challenge dose.

Statistical Evaluation:

Median effective doses ($ED_{50}$s) and 95% confidence limits are determined numerically by the methods of Thompson (1947) and Litchfield and Wilcoxon (1949).

What is claimed is:

1. A compound of the formula 1(A–F) having the following structure:

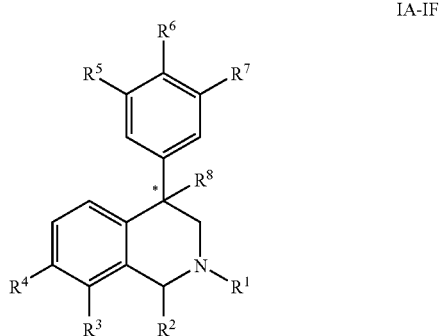

IA-IF wherein: the carbon atom designated * is in the R or S configuration;

$R^1$ is $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, each of which is optionally substituted with 1 to 3 substituents independently selected at each occurrence thereof from $C_1$–$C_3$ alkyl, halogen, aryl, —CN, $OR^9$ and —$NR^9R^{10}$;

$R^2$ is H, $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl or $C_1$–$C_6$ haloalkyl;

$R^3$ is H, —$OR^{11}$, —$S(O)_nR^{12}$, —$S(O)_nNR^{11}R^{12}$, —C(O)$R^{12}$, —C(O)$NR^{11}R^2$, $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl, —O(phenyl), or —O(benzyl), wherein each of —O(phenyl) and —O(benzyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy, or wherein when $R^3$ is a $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl group, then said group is optionally substituted with from 1 to 3 substituents selected independently at each occurrence thereof from $C_1$–$C_3$ alkyl, halogen, aryl, —CN, —OR$^9$ and —NR$^9$R$^{10}$; provided that for compounds of formula IA, R$^3$ is C$_1$–C$_6$ alkyl, C$_2$–C$_6$ alkenyl, C$_2$–C$_6$ alkynyl, C$_3$–C$_6$ cycloalkyl or C$_4$–C$_7$ cycloalkylalkyl, each of which is optionally substituted with from 1 to 3 substituents selected independently at each occurrence thereof from C$_1$–C$_3$ alkyl, halogen, aryl, —CN, —OR$^9$ and —NR$^9$R$^{10}$;

provided that for compounds of formula IB, R$^3$ is —O(phenyl), —O(benzyl), or S(O)$_n$R$^{12}$, each of —O(phenyl) and —O(benzyl) is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy;

R$^4$ is H, halogen, —S(O)$_n$R$^{12}$, —S(O)NR$^{11}$R$^{12}$, —CN, —C(O)R$^2$, —C(O)NR$^{11}$R$^{12}$, —NR$^{11}$R$^{12}$, C$_1$–C$_6$ alkyl, C$_2$–C$_6$ alkenyl, C$_2$–C$_6$ alkynyl, C$_3$–C$_6$ cycloalkyl, C$_4$–C$_7$ cycloalkylalkyl, —O(phenyl), —OC(O)R$^{13}$, or —O(benzyl), wherein each of —O(phenyl) and —O(benzyl) is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy and wherein when R$^4$ is a C$_1$–C$_6$ alkyl, C$_2$–C$_6$ alkenyl, C$_2$–C$_6$ alkynyl, C$_3$–C$_6$ cycloalkyl or C$_4$–C$_7$ cycloalkylalkyl group, then said group is optionally substituted with at from 1 to 3 substituents selected independently at each occurrence thereof from C$_1$–C$_3$ alkyl, halogen, aryl, —CN, —OR$^9$ and —NR$^9$R$^{10}$; provided that for compounds of formula IC, R$^4$ is C$_1$–C$_6$ alkyl, C$_2$–C$_6$ alkenyl, C$_2$–C$_6$ alkynyl, C$_3$–C$_6$ cycloalkyl or C$_4$–C$_7$ cycloalkylalkyl, each of which is optionally substituted; provided that for compounds of formula ID, R$^4$ is —O(phenyl), —O(benzyl), —OC(O)R$^{13}$, —NR$^{11}$R$^{12}$ or —S(O)$_n$R$^{12}$, each of —O(phenyl) and —O(benzyl) being optionally substituted, wherein R$^3$ and R$^4$ are not both H;

R$^5$, R$^6$ and R$^7$ in compounds of each of the formulae IA, IB, IC, ID, IE and IF are each independently H, halogen, —OR$^{11}$, —S(O)$_n$R$^{12}$, —CN, —C(O)R, —NR$^{11}$R$^{12}$, —C(O)NR$^{11}$R$^{12}$, —NR$^{11}$C(O)R$^{12}$, —NR$^{11}$C(O)$_2$R$^{12}$, —NR$^{11}$C(O)NR$^{12}$R$^{13}$, —C—C$_6$ alkyl, C$_2$–C$_6$ alkenyl, C$_2$–C$_6$ alkynyl, C$_3$–C$_6$ cycloalkyl or C$_4$–C$_7$ cycloalkylalkyl, wherein when each of R$^5$, R$^6$ and R$^7$ is a C$_1$–C$_6$ alkyl, C$_2$–C$_6$ alkenyl, C$_2$–C$_6$ alkynyl, C$_3$–C$_6$ cycloalkyl or C$_4$–C$_7$ cycloalkylalkyl group, then said group is optionally substituted with from 1 to 3 substituents selected independently at each occurrence thereof from C$_1$–C$_3$ alkyl, halogen, aryl, —CN, —OR$^9$ and —NR$^9$R$^{10}$, or R$^5$ and R$^6$ or R$^6$ and R$^7$ may together be —O—C(R$^{12}$)$_2$—O—; provided that for compounds of formula IE at least one of R$^5$ or R$^7$ is fluoro, chloro, or methyl; or R$^5$ and R$^6$ are together —O—C(R$^{12}$)$_2$—O— in compounds of the formulae IE, but only where R$^7$ is fluoro, chloro or methyl; or R$^7$ and R$^6$ are together —O—C(R$^{12}$)$_2$—O— in compounds of the formulae IE, but only where R$^5$ is fluoro, chloro or methyl;

R$^8$ is H or halogen, provided that for compounds of formula IF, R$^8$ is halogen;

R$^9$ and R$^{10}$ are each independently H, C$_1$–C$_4$ alkyl, C$_1$–C$_4$ haloalkyl, C$_1$–C$_4$ alkoxyalkyl, C$_3$–C$_6$ cycloalkyl, C$_4$–C$_7$ cycloalkylalkyl, —C(O)R$^{13}$, phenyl or benzyl, where phenyl or benzyl is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy; or R$^9$ and R$^{10}$ are taken together with the nitrogen to which they are attached to form piperidine, pyrrolidine, piperazine, N-methylpiperazine, morpholine, or thiomorpholine;

R$^{11}$ is H, C$_1$–C$_4$ alkyl, C$_1$–C$_4$ haloalkyl, C$_1$–C$_4$ alkoxyalkyl, C$_3$–C$_6$ cycloalkyl, C$_4$–C$_7$ cycloalkylalkyl, —C(O)R$^{13}$, phenyl or benzyl, where R$^{11}$ is a C$_1$–C$_4$ alkyl, phenyl or benzyl group, then said group is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy;

R$^{12}$ is H, amino, C$_1$–C$_4$ alkyl, (C$_1$–C$_4$ alkyl)amino, C$_1$–C$_4$ haloalkyl, C$_1$–C$_4$ alkoxyalkyl, C$_3$–C$_6$ cycloalkyl, C$_4$–C$_7$ cycloalkylalkyl, phenyl or benzyl, where phenyl or benzyl is optionally substituted from 1 to 3 times with a substituent selected independently from halogen, cyano, C$_1$–C$_4$ alkyl, C$_1$–C$_4$ haloalkyl and C$_1$–C$_4$ alkoxy; or R$^{11}$ and R$^{12}$ are taken together with the nitrogen to which they are attached to form piperidine, pyrrolidine, piperazine, N-methylpiperazine, morpholine, or thiomorpholine;

provided that only one of R$^9$ and R$^{10}$ are taken together with the nitrogen to which they are attached to form piperidine, pyrrolidine, piperazine, N-methylpiperazine, morpholine, or thiomorpholine;

R$^{13}$ is C$_1$–C$_4$ alkyl, C$_1$–C$_4$ haloalkyl or phenyl;

n is 0, 1, or 2, and;

aryl is phenyl which is optionally substituted 1–3 times with halogen, cyano, C$_1$–C$_4$ alkyl, C$_1$–C$_4$ haloalkyl and C$_1$–C$_4$ alkoxy, or an oxide thereof, or a pharmaceutically acceptable salt thereof and, wherein if R$^3$ is —S(O)$_n$R$^{12}$, n cannot be 0, and wherein if R$^3$ is —OR$^{11}$, R$^{11}$ cannot be hydrogen.

2. The compound of claim 1, wherein R$^1$ is C$_1$–C$_3$ alkyl.

3. The compound of claim 2, wherein R$^1$ is CH$_3$.

4. The compound of claim 1, wherein R$^2$ is H, C$_1$–C$_4$ alkyl or C$_1$–C$_6$ haloalkyl.

5. The compound of claim 4, wherein R$^2$ is H or CH$_3$.

6. The compound of claim 1, wherein R$^3$ is H or R$^3$ is C$_1$–C$_4$ alkyl, C$_3$–C$_6$ cycloalkyl or C$_4$–C$_7$ cycloalkylalkyl, each of which is optionally substituted with from 1 to 3 substituents selected independently at each occurrence thereof from C$_1$–C$_3$ alkyl, halogen, aryl, —CN, —OR$^9$ and —NR$^9$R$^{10}$ or R$^3$ is —O(phenyl) or —O(benzyl) optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy.

7. The compound of claim 6, wherein R$^3$ is methyl, ethyl, propyl, or isopropyl.

8. The compound of claim 6, wherein R$^3$ is —O(phenyl) or —O—CH$_2$— (phenyl), each of which is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy.

9. The compound of claim 6, wherein R$^3$ is H.

10. The compound of claim 1, wherein R$^4$ is H, or R$^4$ is —NR$^{11}$R$^{12}$ or R$^4$ is C$_1$–C$_4$ alkyl, C$_3$–C$_6$ cycloalkyl or C$_4$–C$_7$ cycloalkylalkyl, each of which is optionally substituted, or wherein R$^4$ is —O(phenyl) or —O(benzyl), each of which is optionally substituted from 1 to 3 times with a substituent selected independently at each occurrence thereof from halogen, cyano, C$_1$–C$_4$ alkyl, C$_1$–C$_4$ haloalkyl, or C$_1$–C$_4$ alkoxy.

11. The compound of claim 10, wherein R$^4$ is methyl, ethyl, propyl, or isopropyl.

12. The compound of claim 10, wherein R$^4$ is —O(phenyl) or —O(CH$_2$)(phenyl), each of which is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy.

13. The compound of claim 10, wherein $R^4$ is H.

14. The compound of claim 1, wherein $R^4$ is halogen.

15. The compound of claim 1, wherein one of $R^3$ and $R^4$ is H and the other is $CH_3$.

16. The compound of claim 1, wherein $R^5$, $R^6$ and $R^7$ are each H, halogen, —$OR^{11}$, —$NR^{11}R^{12}$, $C_1$–$C_6$ alkyl and substituted $C_1$–$C_6$ alkyl.

17. The compound of claim 16, wherein $R^5$, $R^6$ and $R^7$ are each H.

18. The compound of claim 16, wherein one of $R^5$ or $R^7$ is F, Cl, or Me and the other of $R^5$ or $R^7$ and $R^6$ are H, halogen, —$OR^{11}$, —$NR^{11}R^{12}$, or optionally substituted $C_1$–$C_6$ alkyl.

19. The compound of claim 18, wherein $R^5$ is F, Cl or Me; and $R^7$ is H.

20. The compound of claim 18, wherein $R^5$ is F, Cl or Me; and $R^6$ is H.

21. The compound of claim 1, wherein $R^8$ is halogen.

22. The compound of claim 21, wherein $R^8$ is fluoro.

23. The compound of claim 1, wherein:
$R^1$ is $C_1$–$C_3$ alkyl;
$R^2$ is H, $C_1$–$C_4$ alkyl or $C_1$–$C_6$ haloalkyl;
$R^3$ is $C_1$–$C_4$ alkyl, $C_3$–$C_6$ cycloalkyl or $C_4$–$C_7$ cycloalkylalkyl, each of which is optionally substituted, or $R^3$ is —O(phenyl) or —O(benzyl), each of which is optionally substituted, or $R^3$ is H;
$R^4$ is H, $C_1$–$C_4$ alkyl, $C_3$–$C_6$ cycloalkyl or $C_4$–$C_7$ cycloalkylalkyl, each of which, other than H, is optionally substituted with from 1 to 3 substituents selected independently at each occurrence thereof from $C_1$–$C_3$ alkyl, halogen, aryl, —CN, —$OR^9$ and —$NR^9R^{10}$, or $R^4$ is —$NR^{11}R^{12}$, —O(phenyl) or —O(benzyl), wherein said —O(phenyl) or —O(benzyl), is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy; or $R^4$ is halogen;
$R^5$, $R^6$ and $R^7$ are each halogen, —$OR^{11}$, —$NR^{11}R^{12}$, or $C_1$–$C_6$ alkyl or one of $R^5$ and $R^7$ is Cl, F or Me and the other of $R^5$ and $R^7$ and $R^6$ is H, halogen, —$NR^{11}R^{12}$, $C_1$–$C_6$ alkyl or substituted $C_1$–$C_6$ alkyl.

24. The compound of claim 1, wherein:
$R^1$ is $CH_3$;
$R^2$ is H or $CH_3$;
$R^3$ is H, methyl, ethyl, propyl, isopropyl, —O(phenyl) or —O—$CH_2$— (phenyl), wherein said —O(phenyl) or —O—$CH_2$— (phenyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;
$R^4$ is H, F, methyl, ethyl, propyl, isopropyl, —O(phenyl) or —O—$CH_2$— (phenyl), wherein said —O(phenyl) or —O—$CH_2$— (phenyl) is optionally substituted from 1 to 3 times with a substituent selected independently at each occurrence thereof from halogen, cyano, $C_1$–$C_4$ alkyl, $C_1$–$C_4$ haloalkyl, or $C_1$–$C_4$ alkoxy;
$R^5$, $R^6$ and $R^7$ are each H or $R^5$ is F, Cl or Me, or one of $R^6$ or $R^7$ is H and the other of $R^6$ and $R^7$ is halogen, —$OR^{11}$, —$NR^{11}R^{12}$, or optionally substituted $C_1$–$C_6$ alkyl.

25. The compound of claim 24, wherein $R^8$ is halogen.

26. The compound according to claim 1, wherein the carbon atom designated * is in the R configuration.

27. The compound according to claim 1, wherein the carbon atom designated * is in the S configuration.

28. A composition comprising a mixture of stereoisomeric compounds of claim 1 wherein the carbon atom designated * is in the S or R configuration.

29. The compound according to claim 1, selected from the group consisting of the following compounds:
4-(4-methoxy)phenyl-2,7-dimethyl-1,2,3,4-tetrahydroisoquinoline;
2,7-dimethyl-4-(4-fluoro)phenyl-1,2,3,4-tetrahydroisoquinoline;
2,7-dimethyl-4-(3-fluoro)phenyl-1,2,3,4-tetrahydroisoquinoline;
4-(3,4-difluoro)phenyl-2,7-dimethyl-1,2,3,4-tetrahydroisoquinoline;
2,7-dimethyl-4-(4-fluoro-3-methyl)phenyl-1,2,3,4-tetrahydroisoquinoline;
4-(3-chloro-4-fluoro)phenyl-2,7-dimethyl-1,2,3,4-tetrahydroisoquinoline;
4-(3-chloro)phenyl-2,7-dimethyl-1,2,3,4-tetrahydroisoquinoline;
2,7-dimethyl-4-(4-methyl)phenyl-1,2,3,4-tetrahydroisoquinoline;
2,7-dimethyl-4-(3-fluoro-4-methyl)phenyl-1,2,3,4-tetrahydroisoquinoline;
4-(4-chloro)phenyl-2,7-dimethyl-1,2,3,4-tetrahydroisoquinoline;
4-(4-chloro-3-fluoro)phenyl-2,7-dimethyl-1,2,3,4-tetrahydroisoquinoline;
4-(3,4-dichloro)phenyl-2,7-dimethyl-1,2,3,4-tetrahydroisoquinoline;
7-ethyl-2-methyl-4-phenyl-1,2,3,4-tetrahydroisoquinoline;
4-(3,4-difluoro)phenyl-7-ethyl-2-methyl-1,2,3,4-tetrahydroisoquinoline;
7-fluoro-4-(3-fluoro-4-methoxy)phenyl-2-methyl-1,2,3,4-tetrahydroisoquinoline;
7-fluoro-4-(3-fluoro-4-methyl)phenyl-2-methyl-1,2,3,4-tetrahydroisoquinoline;
7-fluoro-4-(4-chloro-3-fluoro)phenyl-2-methyl-1,2,3,4-tetrahydroisoquinoline;
4-(3,4-difluoro)phenyl-7-fluoro-2-methyl-1,2,3,4-tetrahydroisoquinoline;
4-(3-chloro)phenyl-7-fluoro-2-methyl-1,2,3,4-tetrahydroisoquinoline;
2-methyl-4-phenyl-7-trifluoromethyl-1,2,3,4-tetrahydroisoquinoline;
4-phenyl-1,2,7-trimethyl-1,2,3,4-tetrahydroisoquinoline;
2,8-dimethyl-7-fluoro-4-phenyl-1,2,3,4-tetrahydroisoquinoline;
2-methyl-7-phenoxy-4-phenyl-1,2,3,4-tetrahydroisoquinoline;
7-(4-methoxy)phenoxy-2-methyl-4-phenyl-1,2,3,4-tetrahydroisoquinoline;
7-benzyloxy-2-methyl-4-phenyl-1,2,3,4-tetrahydroisoquinoline;
2,8-dimethyl-4-(4-fluoro)phenyl-1,2,3,4-tetrahydroisoquinoline;
4-(3,4-difluoro)phenyl-2,8-dimethyl-1,2,3,4-tetrahydroisoquinoline;
4-(3,5-difluoro)phenyl-2,8-dimethyl-1,2,3,4-tetrahydroisoquinoline;
2,8-dimethyl-4-(3-fluoro)phenyl-1,2,3,4-tetrahydroisoquinoline;
2,8-dimethyl-4-(4-fluoro-3-methyl)phenyl-1,2,3,4-tetrahydroisoquinoline;
4-(3-chloro-4-fluoro)phenyl-2,8-dimethyl-1,2,3,4-tetrahydroisoquinoline;

4-(3,4-dichloro)phenyl-2,8-dimethyl-1,2,3,4-tetrahydroisoquinoline;
4-(3-chloro)phenyl-2,8-dimethyl-1,2,3,4-tetrahydroisoquinoline;
4-(4-chloro)phenyl-2,8-dimethyl-1,2,3,4-tetrahydroisoquinoline;
4-(4-chloro-3-fluoro)phenyl-2,8-dimethyl-1,2,3,4-tetrahydroisoquinoline;
2,8-dimethyl-4-(4-methoxy)phenyl-1,2,3,4-tetrahydroisoquinoline;
4-(4-cyano)phenyl-2,8-dimethyl-1,2,3,4-tetrahydroisoquinoline;
2,8-dimethyl-4-(4-trifluoromethyl)phenyl-1,2,3,4-tetrahydroisoquinoline;
2,8-dimethyl-4-(4-methyl)phenyl-1,2,3,4-tetrahydroisoquinoline;
2-methyl-8-(N-methylamino)methyl-4-phenyl-1,2,3,4-tetrahydroisoquinoline;
8-(hydroxy)methyl-2-methyl-4-phenyl-1,2,3,4-tetrahydroisoquinoline;
2-methyl-4-phenyl-8-sulfonamide-1,2,3,4-tetrahydroisoquinoline;
2-methyl-8-(N-methyl)sulfonamide-4-phenyl-1,2,3,4-tetrahydroisoquinoline;
4-(3,5-difluoro)phenyl-2,7-dimethyl-1,2,3,4-tetrahydroisoquinoline;
4-(3-chloro-5-fluoro)phenyl-2,7-dimethyl-1,2,3,4-tetrahydroisoquinoline;
4-(3,5-difluoro)phenyl-1,2,7-trimethyl-1,2,3,4-tetrahydroisoquinoline;
2-methyl-4-phenyl-1,2,3,4-tetrahydro-7-isoquinolinyl)-N-methylmethanamine;
N-methyl(2-methyl-4-phenyl-1,2,3,4-tetrahydro-7-isoquinolinyl)-N-methylmethanamine;
(2-methyl-4-phenyl-1,2,3,4-tetrahydro-7-isoquinolinyl)methanol; and
an oxide thereof, or a pharmaceutically acceptable salt thereof.

30. The compound according to claim 1, selected from the group consisting of the following compounds:

| $R^1$ | $R^2$ | $R^3$ | $R^4$ | $R^5$ | $R^6$ | $R^7$ | $R^8$ |
|---|---|---|---|---|---|---|---|
| Me | H | H | Me | H | OMe | H | H |
| Me | H | H | Me | H | F | H | H |
| Me | H | H | Me | F | H | H | H |
| Me | H | H | Me | F | F | H | H |
| Me | H | H | Me | Me | F | H | H |
| Me | H | H | Me | Cl | F | H | H |
| Me | H | H | Me | Cl | H | H | H |
| Me | H | H | Me | H | Me | H | H |
| Me | H | H | Me | F | Me | H | H |
| Me | H | H | Me | H | Cl | H | H |
| Me | H | H | Me | F | Cl | H | H |
| Me | H | H | Me | Cl | Cl | H | H |
| Me | H | H | Et | H | H | H | H |
| Me | H | H | Et | F | F | H | H |
| Me | H | H | F | F | OMe | H | H |
| Me | H | H | F | F | Me | H | H |
| Me | H | H | F | F | Cl | H | H |
| Me | H | H | F | F | F | H | H |
| Me | H | H | F | Cl | H | H | H |
| Me | H | H | CF$_3$ | H | H | H | H |
| Me | Me | H | Me | H | H | H | H |
| Me | H | Me | Me | H | H | H | H |
| Me | H | Me | F | H | H | H | H |
| Me | H | H | O(Ph) | H | H | H | H |
| Me | H | H | O(4-OMePh) | H | H | H | H |
| Me | H | H | O(CH$_2$Ph) | H | H | H | H |
| Me | H | Me | H | H | F | H | H |

-continued

| $R^1$ | $R^2$ | $R^3$ | $R^4$ | $R^5$ | $R^6$ | $R^7$ | $R^8$ |
|---|---|---|---|---|---|---|---|
| Me | H | Me | H | F | F | H | H |
| Me | H | Me | H | F | H | F | H |
| Me | H | Me | H | F | H | H | H |
| Me | H | Me | H | Me | F | H | H |
| Me | H | Me | H | Cl | F | H | H |
| Me | H | Me | H | Cl | Cl | H | H |
| Me | H | Me | H | Cl | H | H | H |
| Me | H | Me | H | H | Cl | H | H |
| Me | H | Me | H | F | Cl | H | H |
| Me | H | Me | H | H | OMe | H | H |
| Me | H | Me | H | H | CN | H | H |
| Me | H | Me | H | H | CF3 | H | H |
| Me | H | Me | H | H | Me | H | H |
| Me | H | CH$_2$NHMe | H | H | H | H | H |
| Me | H | CH$_2$OH | H | H | H | H | H |
| Me | H | SO$_2$NH$_2$ | H | H | H | H | H |
| Me | H | SO$_2$NHMe | H | H | H | H | H |
| Me | H | H | Me | F | H | F | H |
| Me | H | H | Me | F | H | Cl | H |
| Me | Me | H | Me | F | H | F | H |
| Me | H | H | Me | F | F | F | H |
| Et | H | H | Me | H | F | H | H |
| Me | H | H | CH$_2$NH$_2$ | H | H | H | H |
| Me | H | H | CH$_2$NHMe | H | H | H | H |
| Me | H | H | CH$_2$OH | H | H | H | H. |

31. The compound according to claim 1, wherein, the compound has the formula:

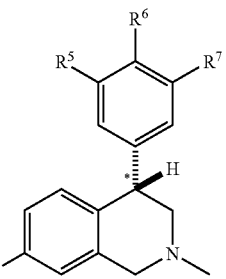

where:

| $R^4$ | $R^5$ | $R^6$ | $R^7$ |
|---|---|---|---|
| Me | H | F | F |
| Me | F | H | F |
| Me | H | F | H |
| Me | H | H | F |

32. The compound according to claim 29, which is the (+) stereoisomer.

33. The compound according to claim 29, which is the (−) stereoisomer.

34. A pharmaceutical composition comprising a pharmaceutically acceptable carrier and a therapeutically effective amount of the compound of claim 1.

35. A method of treating a disorder selected from the group consisting of attention deficit disorder, hyperactivity disorder, anxiety, depression, post-traumatic stress disorder, supranuclear palsy, eating disorders, obsessive compulsive disorder, analgesia, nicotine addiction, panic attacks, Parkinsonism and phobia, obesity, late luteal phase syndrome or narcolepsy, cocaine addiction, amphetamine addiction, rejection sensitivity, and lack of mental or physical energy, wherein said method comprises:
  administering to a patient in need of such treatment a therapeutically effective amount of a compound according to claim 1, or a pharmaceutically acceptable salt thereof.

36. The method of claim 35 wherein the (+)-stereoisomer of the compound is employed.

37. The method of claim 35, wherein the (−)-stereoisomer of the compound is employed.

38. The method of claim 35, wherein the disorder is attention deficit disorder or hyperactivity disorder.

* * * * *

UNITED STATES PATENT AND TRADEMARK OFFICE
CERTIFICATE OF CORRECTION

PATENT NO. : 7,163,949 B1
APPLICATION NO. : 09/704306
DATED : January 16, 2007
INVENTOR(S) : Beck et al.

It is certified that error appears in the above-identified patent and that said Letters Patent is hereby corrected as shown below:

At claim 1, column 58, line 27, "formula 1(A-F)" should read --formula I(A-F)--.

At claim 1, column 59, line 15, "-C(O)R$^2$" should read --C(O)R$^{12}$-- ; line 38, "-C(O)R" should read --C(O)R$^{12}$-- ; line 40, "-C-C$_6$" should read --C$_1$-C$_6$-- ;and lines 51 to 52, "-0-C(R$^{12}$)$_2$-O-" should read --O-C(R$^{12}$)$_2$-O--.

At claim 25, column 61, line 63, the claim reference numeral "24" should read --23--.

Signed and Sealed this

Twelfth Day of June, 2007

JON W. DUDAS
*Director of the United States Patent and Trademark Office*